US012723071B2

(12) United States Patent
Chain

(10) Patent No.: US 12,723,071 B2
(45) Date of Patent: Sep. 1, 2026

(54) FUSION CONSTRUCTS AND USES THEREOF

(71) Applicant: B-Portal Biologics, Inc., New York, NY (US)

(72) Inventor: Daniel Chain, New York, NY (US)

(73) Assignee: B-Portal Biologics, Inc., New York, NY (US)

( * ) Notice: Subject to any disclaimer, the term of this patent is extended or adjusted under 35 U.S.C. 154(b) by 1717 days.

(21) Appl. No.: 16/838,467

(22) Filed: Apr. 2, 2020

(65) Prior Publication Data

US 2020/0385461 A1 Dec. 10, 2020

Related U.S. Application Data

(60) Provisional application No. 62/829,776, filed on Apr. 5, 2019.

(51) Int. Cl.

| | |
|---|---|
| ***C07K 16/18*** | (2006.01) |
| ***A61K 39/00*** | (2006.01) |
| ***A61P 25/28*** | (2006.01) |

(52) U.S. Cl.

CPC .............. *C07K 16/18* (2013.01); *A61P 25/28* (2018.01); *A61K 2039/505* (2013.01); *C07K 2317/565* (2013.01); *C07K 2317/92* (2013.01); *C07K 2319/033* (2013.01)

(58) Field of Classification Search

CPC combination set(s) only.
See application file for complete search history.

(56) References Cited

U.S. PATENT DOCUMENTS

| | | | |
|---|---|---|---|
| 3,955,137 | A | 5/1976 | Harrington et al. |
| 3,978,797 | A | 9/1976 | Harrington et al. |
| 4,092,603 | A | 5/1978 | Harrington |
| 4,166,817 | A | 9/1979 | Ferres et al. |
| 5,492,812 | A | 2/1996 | Voohies |
| 5,846,546 | A | 12/1998 | Hurwitz et al. |
| 6,232,437 | B1 | 5/2001 | Vandermeeren et al. |

(Continued)

FOREIGN PATENT DOCUMENTS

| | | | | |
|---|---|---|---|---|
| EP | 3556399 | A1 * | 10/2019 | ............. A61K 47/10 |
| JP | 2010533170 | A | 10/2010 | |
| WO | WO 2005/035550 | A2 | 4/2005 | |
| WO | WO 2009/008725 | A2 | 1/2009 | |

(Continued)

OTHER PUBLICATIONS

AntibodySystem, "Antibody Structure, classes, and functions." Published Aug. 23, 2021 https://www.antibodysystem.com/archive/48.html (Year: 2021).*

(Continued)

*Primary Examiner* — Jeffrey Stucker
*Assistant Examiner* — Laura Ann Essex
(74) *Attorney, Agent, or Firm* — Davidson Kappel LLC

(57) ABSTRACT

Fusion constructs are described. A fusion construct contains a peptide of SEQ ID NO: 2, SEQ ID NO: 3, SEQ ID NO: 4, SEQ ID NO: 5, or SEQ ID NO: 28, fused to a peptide or protein (e.g., an antibody). As compared to the peptide or protein, fusion constructs exhibits improved penetration through the BBB, and are released on the abluminal surface of the BBB, after the post-luminal surface uptake. Fusion constructs could be used in drug discovery, diagnosis, prevention and treatment of diseases.

17 Claims, 32 Drawing Sheets

Specification includes a Sequence Listing.

(56) References Cited

U.S. PATENT DOCUMENTS

| | | | | |
|---|---|---|---|---|
| 6,376,205 | B1 | 4/2002 | Wischik et al. | |
| 6,762,179 | B2 | 7/2004 | Cochran et al. | |
| 6,953,794 | B2 | 10/2005 | Wischik et al. | |
| 7,238,788 | B2 | 7/2007 | Lee | |
| 7,256,190 | B2 | 8/2007 | Cochran et al. | |
| 7,335,505 | B2 | 2/2008 | Wischik et al. | |
| 7,335,652 | B2 | 2/2008 | Wischik et al. | |
| 7,488,727 | B2 | 2/2009 | Cochran et al. | |
| 7,534,786 | B2 | 5/2009 | Wischik et al. | |
| 7,605,179 | B2 | 10/2009 | Wischik et al. | |
| 7,713,962 | B2 | 5/2010 | Wischik et al. | |
| 7,737,138 | B2 | 6/2010 | Wischik et al. | |
| 7,741,446 | B2 | 6/2010 | Pardridge et al. | |
| 7,790,881 | B2 | 9/2010 | Storey et al. | |
| 7,834,237 | B2 | 11/2010 | Wischik et al. | |
| 7,901,689 | B2 | 3/2011 | Chain | |
| 8,012,936 | B2 | 9/2011 | Sigurdsson et al. | |
| 8,173,127 | B2 | 5/2012 | Chain | |
| 8,609,065 | B2 | 12/2013 | Kuik-Romeijn et al. | |
| 8,703,137 | B2 | 4/2014 | Chain | |
| 2002/0086847 | A1 | 7/2002 | Chain | |
| 2002/0168687 | A1 | 11/2002 | Wischik et al. | |
| 2003/0194742 | A1 | 10/2003 | Vanmechelen | |
| 2004/0078835 | A1 | 4/2004 | Wischik et al. | |
| 2004/0082763 | A1 | 4/2004 | Novak | |
| 2004/0268425 | A1 | 12/2004 | Bookbinder | |
| 2005/0075308 | A1 | 4/2005 | Wilson | |
| 2006/0088548 | A1 | 4/2006 | Chain | |
| 2006/0167227 | A1 | 7/2006 | Kontsekova | |
| 2007/0166311 | A1 | 7/2007 | Greferath | |
| 2008/0050383 | A1 | 2/2008 | Sigurdsson et al. | |
| 2008/0125347 | A1 | 5/2008 | Grabstein | |
| 2008/0207603 | A1 | 8/2008 | Storey et al. | |
| 2008/0207604 | A1 | 8/2008 | Wischik et al. | |
| 2008/0219929 | A1 | 9/2008 | Wischik et al. | |
| 2008/0220449 | A1 | 9/2008 | Vasan | |
| 2009/0054419 | A1 | 2/2009 | Wischik et al. | |
| 2009/0075984 | A1 | 3/2009 | Wischik et al. | |
| 2009/0093002 | A1 | 4/2009 | Pfeifer | |
| 2009/0123936 | A1 | 5/2009 | Novak | |
| 2009/0155249 | A1 | 6/2009 | Pfeifer | |
| 2009/0209526 | A1 | 8/2009 | Wischik et al. | |
| 2009/0258031 | A1 | 10/2009 | Karrer | |
| 2010/0015095 | A1 | 1/2010 | Pan | |
| 2010/0184947 | A1* | 7/2010 | Kuik-Romeijn ........ | A61P 25/00<br>530/323 |
| 2010/0280975 | A1 | 11/2010 | Wischik et al. | |
| 2010/0285605 | A1 | 11/2010 | Wischik et al. | |
| 2010/0290986 | A1 | 11/2010 | Wischik et al. | |
| 2010/0316564 | A1 | 12/2010 | Sigurdsson | |
| 2011/0142824 | A1 | 6/2011 | Burbridge et al. | |
| 2011/0177109 | A1 | 7/2011 | Smith, III et al. | |
| 2011/0256587 | A1* | 10/2011 | Macdonald ............. | A61P 35/00<br>435/69.6 |
| 2012/0087861 | A1 | 4/2012 | Nitsch et al. | |
| 2012/0244159 | A1 | 9/2012 | Chain | |
| 2016/0347840 | A1* | 12/2016 | Glenn ..................... | A61P 11/00 |
| 2020/0079825 | A1 | 3/2020 | Takeda et al. | |

FOREIGN PATENT DOCUMENTS

| | | | |
|---|---|---|---|
| WO | WO 2012/045882 | | 4/2012 |
| WO | WO 2012/149365 | | 11/2012 |
| WO | WO 2015/031673 | A2 | 3/2015 |
| WO | WO 2015/155694 | A1 | 10/2015 |
| WO | WO 2017/027685 | A2 | 2/2017 |
| WO | WO 2018/007950 | A1 | 1/2018 |
| WO | WO 2020/20182 | A1 | 10/2020 |

OTHER PUBLICATIONS

Excellerate Bioscience, Kinetics fact sheet, Accessed on Jan. 15, 2025 https://excelleratebio.com/wp-content/uploads/2021/02/kinetics-fact-sheet-1.pdf (Year: 2025).*

Kussie PH, Parhami-Seren B, Wysocki LJ, Margolies MN. J Immunol. Jan. 1, 1994;152(1):146-52. PMID: 8254187. (Year: 1994).*

Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*

International Search Report issued on Aug. 17, 2012, in connection with International Application PCT/US2012/023375.

Written Opinion of the International Searching Authority issued on Aug. 17, 2012, in connection with International Application PCT/US2012/023375.

Sengupta et al., "Degradation of Tau Protein by Puromycin-Sensitive Aminopeptidase in Vitro", Biochemistry, Nov. 24, 2006, vol. 45, pp. 15111-15119.

Gamblin et al., "Caspase cleavage of tau: Linking amyloid and neurofibrillary tangles in Alzheimer's disease", Proceedings of the National Academy of Sciences, Aug. 19, 2003, vol. 100, No. 17, pp. 10032-10037.

Yamamoto et al., "Phosphorylation of tau at serine 416 by Ca2+/calmodulin-dependent protein kinase II in neuronal soma in brain", Journal of Neurochemistry, Jul. 5, 2005, vol. 94, pp. 1438-1447.

Vestergaard et al., "Detection of Alzheimer's tau protein using localised surface plasmon resonance-based immunochip", Talanta, Jun. 17, 2007 ,vol. 74, pp. 1039-1042.

Lars M. Ittner et al., "Amlyiod-B and tau-a toxic pas de deux in Alzheimer's disease", Nature Reviews, NeuroScience, Feb. 2011, vol. 12.

Alix de Calignon et al., "Caspase activation precedes and leads to tangles", vol. 464: 12, Apr. 2, 2010.

B. Kovacech et al., Tau Truncation in a productive Pottranslational Modification of Neurofibrillary Degeneration in Alzheimer's Disease, Current Alzheimer's Research, 2010, pp. 708-716.

Robert A. Rissman et al., "Caspase-cleavage of tau is an early event in Alzheimer disease tangle pathology", The Journal of Clinical Investigation, Jul. 2001, vol. 114, pp. 115-130.

Khurana V, Elson-Schwab I, Fulga TA, Sharp KA, Loewen CA, et al.. Lysosomal Dysfunction Promotes Cleavage and Neurotoxicity of Tau In Vivo. PLoS Genet 6(7): e1001026. doi: 10.1371/journal.pgen.1001026, (2010).

Peleg M. Horowitz et al., Early Changes and Capase-6 Cleavage of Tau in Alzheimers Disease, The Journal of Neuroscience, Sep. 8, 2004, vol. 24(36) pp. 7895-7902.

Patrice Delobel et al, "Analysis of Tau Phosphorylation and Truncation in a Mouse Model of Human Tauopathy", Molecular Pathogenesis of Genetic and Inherited Diseases; The American Journal of Pathology, vol. 172, Jan. 2008. pp. 123-131.

Ayodeji A. Asuni et al., "Immunotherapy Targeting Pathological Tau Conformers in a Tangle Mouse Model Reduces Brain Pathology with Associated Functional Improvements", Neurobiology of Disease, The Journal of Neuroscience, Aug. 22, 2007, vol. 27(34), pp. 9115-9129.

Einar M. Sigurdsson, "Tau-Focused Immunotherapy for Alzheimer's Disease and Related Tauopathies", Current Alzheimer Research, 2009-6, pp. 446-450.

Einar M.Sigurdsson, "Immunotherapy Tageting Pathological Tau Protein in Alzheimer's Disease and Related Tauopathies", journal of Alzheimer's Disease 15, 2008, pp. 157-168.

F. Incardona et al. 1995 "How much are homologous peptides homologous?" J theor bioi 175:437-455.

Qipeng Zhang et al., Truncated tau at D421 is associated with neurodegeneration and tangle formation in the brain of Alzheimer transgenic models, Acta Neuropathol , 2009. vol. 117, pp. 687-697.

Invitrogen, "Mouse (monoclonal) Anti-tau (421/422) Cleavage Site Specific Antibody, Unconjugated", Product Analysis Sheet. Catalog No. AHB0061, (2010).

Millipore, Anti-cleaved-Tau (Asp421), clone C3, Uniprot No. P10636, Jan. 16, 2011, http://www.millipore.com/catalogue/item/36-017.

Allal Boutajangout et al., Immunotherapy targeting pathological tau prevents cognitive decline in a new tangle mouse model, Journal Section: Neurobiology of Disease, (2010).

(56) References Cited

OTHER PUBLICATIONS

Saido 1992 "Autolytic transition of .mu.-calpain upon activation as resolved by antibodies distinguishing between the pre- and post-autolysis forms" J biochem 111 :81-86.
Saido 1993 "Spatial resolution of fodrin proteolysis in postischemic brain" J bio chem 268(33):25239-25243.
Saido 1994 "Spatial resolution of the primary .beta.-amyloidogenic process induced in postischemic hippocampus" J bio chem 269(21 ):15253-15257.
Castillo-Carranza et al. 2013 "Tau aggregates as immunotherapeutic targets" Frontiers in Bioscience 5:426-438.
Delrieu et al. 2012 "Clinical trials in Alzheimer's disease: immunotherapy approaches" J Neurochem 120(Supp 1):186-193.
Rosenmann et al. 2006 "Tauopathy-like Abnormalities and neurologic deficits in mice immunized with neuronal tau protein" Arch Neurol 63:1459-1467.
Harlow and Lane 1988 "Antibodies: A Labratory Manual" Cold Spring Harbor Labratory, Chapter 5, p. 76.
Basurto-Islas et al. 2008 "Accumulation of Aspartic Acid 421 and glutamic acid 391 cleaved tau in neurofibrillary tangles correlates with progression in alzheimer's disease" J neuropathol exp neural 67(5):470-483.
Rafii and Aisen 2009 "recent developments in alzheimer's disease therapeutics" BMC medicine 7(7):1-4.
Nicholls "characterization of tauc3 antibody and demonstration of its potential to block tau propagation" PLOS one 12(5):e0177914 (Year: 2017).
Guillozet-Bongaarts 2005 "tau truncation during neurofibrillary tangle evolution in alzheimer's disease" Neurobiol aging 26:1015-1022.
Declaration of Daniel Chain, dated Mar. 29, 2018.
Chen et al. "Enhancement and destruction of antibody function by somatic mutation: unequal occurrence is controlled by V gene combinatorial associations" the EMBO Journal; vol. 14; No. 12; pp. 2784-2794 (year: 1995).
Kussie et al. "A Single Engineered Amino Acid Substitution Changes Antibody Fine Specificity" J immunol 152(1); pp. 146-152 (year: 1994).
Panza et al. "Beyond the neurotransmitter-focused approach in treating Alzheimer's disease: drugs targeting beta-amyloid and tau protein." Aging Clin Exp Res 21(6): abstract.
International Search Report issued on Jul. 9, 2020, in connection with International Application PCT/IB2020/000243.
Written Opinion of the International Searching Authority issued on Jul. 9, 2020, in connection with International Application PCT/IB2020/000243.
International Search Report issued on Sep. 14, 2020, in connection with International Application PCT/US2020/026349.
Written Opinion of the International Searching Authority issued on Sep. 14, 2020, in connection with International Application PCT/US/2020/026349.
Pacific "What is an epitope" accessed from pacificimmunology.com (Year: 2018).
Mu et al. "Lipid vesicles containing transferrin receptor binding peptide TfR-$T_{12}$ and octa-arginine conjugate stearyl-$R_8$ efficiently treat brain glioma along with glioma stem cells" Scientific Reports 7:3487; DOI: 10.1038/s41598-017-03805-7; www.nature.com/scientificreports; Published Jun. 14, 2017.
Jens Niewoehner, et al., "Increased Brain Penetration and Potency of a Therapeutic Antibody Using a Monovalent Molecular Shuttle", Neuron 81, Jan. 8, 2014.
Nga Bien-Ly, et al., "Transferrin receptor (TfR) trafficking determines brain uptake of TfR antibody affinity variants", The Journal of Experimental Medicine, Jan. 27, 2014.
Jae H. Lee, et al., "Receptor mediated uptake of peptides that bind the human transferrin receptor", European Journal of Biochemistry, vol. 268, No. 7, Apr. 1, 2001.
International Preliminary Report on Patentability mailed on Sep. 28, 2021 in connection with International Application No. PCT/US2020/026349.

* cited by examiner

HBMVEC TBL-100/110 Internalization and Retention

TBL-100 24 Hour Incubation

HBMVEC TBL-100/110 Internalization and Retention
TBL-110 24 Hour Incubation

HBMVEC TBL-100/110 Internalization and Retention

TBL-110 24 Hour Incubation

HBMVEC TBL-100/110 Internalization and Retention

TBL-110 24 Hour Incubation

HBMVEC TBL-100/110 Internalization and Retention

24 Hour Test Article Incubation

HBMVEC TBL-100/110 Internalization and Retention

24 Hour Test Article Incubation

HBMVEC TBL-100 Internalization and Retention
Full Time Course

HBMVEC TBL-100/110 Internalization and Retention
24 Hour Test Article Incubation

HBMVEC TBL-100/110 Internalization and Retention
24 Hour Test Article Incubation

HBMVEC TBL-100/110 Internalization and Retention
24 Hour Test Article Incubation

HBMVEC TBL-100/110 Internalization and Retention

Early Time Points

HBMVEC TBL-100/110 Internalization and Retention

24 Hour Test Article Incubation

HBMVEC TBL-100/110 Internalization and Retention

3 Hour Test Article Incubation

HBMVEC TBL-100/110 Internalization and Retention

6 Hour Test Article Incubation

HBMVEC TBL-100/110 Internalization and Retention

24 Hour Test Article Incubation

```
                              SEQUENCE LISTING


<160> NUMBER OF SEQ ID NOS: 28

<210> SEQ ID NO 1
<211> LENGTH: 441
<212> TYPE: PRT
<213> ORGANISM: Artificial Sequence
<220> FEATURE:
<223> OTHER INFORMATION: HTAU40

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
```

```
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440


<210> SEQ ID NO 2
<211> LENGTH: 12
<212> TYPE: PRT
<213> ORGANISM: Artificial Sequence
<220> FEATURE:
<223> OTHER INFORMATION: transport peptide

<400> SEQUENCE: 2

Thr His Arg Pro Pro Met Trp Ser Pro Val Trp Pro
1               5                   10


<210> SEQ ID NO 3
<211> LENGTH: 11
<212> TYPE: PRT
<213> ORGANISM: Artificial Sequence
<220> FEATURE:
<223> OTHER INFORMATION: transport peptide

<400> SEQUENCE: 3

His Arg Pro Pro Met Trp Ser Pro Val Trp Pro
1               5                   10


<210> SEQ ID NO 4
<211> LENGTH: 11
<212> TYPE: PRT
<213> ORGANISM: Artificial Sequence
<220> FEATURE:
<223> OTHER INFORMATION: transport peptide

<400> SEQUENCE: 4

Thr His Arg Pro Pro Met Trp Ser Pro Val Trp
1               5                   10


<210> SEQ ID NO 5
<211> LENGTH: 10
<212> TYPE: PRT
<213> ORGANISM: Artificial Sequence
<220> FEATURE:
<223> OTHER INFORMATION: transport peptide

<400> SEQUENCE: 5

His Arg Pro Pro Met Trp Ser Pro Val Trp
1               5                   10


<210> SEQ ID NO 6
<211> LENGTH: 4
<212> TYPE: PRT
<213> ORGANISM: Artificial Sequence
<220> FEATURE:
<223> OTHER INFORMATION: linker
```

<400> SEQUENCE: 6

Gly Gly Gly Ser
1

<210> SEQ ID NO 7
<211> LENGTH: 8
<212> TYPE: PRT
<213> ORGANISM: Artificial Sequence
<220> FEATURE:
<223> OTHER INFORMATION: Heavy Chain CDR1 (IMGT definition)

<400> SEQUENCE: 7

Gly Phe Thr Phe Asn Thr Tyr Ala
1               5

<210> SEQ ID NO 8
<211> LENGTH: 10
<212> TYPE: PRT
<213> ORGANISM: Artificial Sequence
<220> FEATURE:
<223> OTHER INFORMATION: Heavy Chain CDR2 (IMGT definition)

<400> SEQUENCE: 8

Ile Arg Ser Lys Ser Asn Asn Tyr Ala Thr
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Heavy Chain CDR3 (IMGT definition)

<400> SEQUENCE: 9

Val Gly Gly Gly Asp Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Light Chain CDR1 (IMGT definition)

<400> SEQUENCE: 10

Gln Glu Ile Ser Val Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Light Chain CDR2 (IMGT definition)

<400> SEQUENCE: 11

Gly Ala Phe
1

<210> SEQ ID NO 12
<211> LENGTH: 9
<212> TYPE: PRT
<213> ORGANISM: Artificial Sequence
<220> FEATURE:
<223> OTHER INFORMATION: Light Chain CDR3 (IMGT definition)

<400> SEQUENCE: 12

Leu Gln Tyr Val Arg Tyr Pro Trp Thr
1               5

<210> SEQ ID NO 13
<211> LENGTH: 115
<212> TYPE: PRT
<213> ORGANISM: Artificial Sequence
<220> FEATURE:
<223> OTHER INFORMATION: Heavy Chain HM

<400> SEQUENCE: 13

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Ala Arg Ile Arg Ser Lys Ser Asn Asn Tyr Ala Thr Tyr Tyr Ala Ala
    50                  55                  60

Ser Val Lys Gly Arg Phe Thr Ile Ser Arg Asp Asp Ser Lys Ser Met
65                  70                  75                  80

Ala Tyr Leu Gln Met Asp Ser Leu Lys Thr Glu Asp Thr Ala Val Tyr
                85                  90                  95

Tyr Cys Val Gly Gly Gly Asp Phe Trp Gly Gln Gly Thr Leu Val Thr
            100                 105                 110

Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: light Chain KE

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Phe Gln Gln Lys Pro Gly Lys Ala Pro Lys Arg Leu Ile
        35                  40                  45

Tyr Gly Ala Phe Lys Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: light Chain KN

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Pro Lys Arg Leu Ile
        35                  40                  45

Tyr Gly Ala Phe Thr Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105


<210> SEQ ID NO 16
<211> LENGTH: 107
<212> TYPE: PRT
<213> ORGANISM: Artificial Sequence
<220> FEATURE:
<223> OTHER INFORMATION: light Chain KO

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Tyr Gln Gln Lys Pro Gly Lys Ala Pro Lys Arg Leu Ile
        35                  40                  45

Tyr Gly Ala Phe Ser Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105


<210> SEQ ID NO 17
<211> LENGTH: 107
<212> TYPE: PRT
<213> ORGANISM: Artificial Sequence
<220> FEATURE:
<223> OTHER INFORMATION: light chain KP

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Gly Trp Phe Gln Gln Lys Pro Gly Lys Ala Pro Lys Arg Leu Ile
        35                  40                  45

Tyr Gly Ala Phe Lys Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
```

```
                85                  90                  95

Thr Phe Gly Gly Gly Thr Lys Val Glu Ile Lys
            100                 105


<210> SEQ ID NO 18
<211> LENGTH: 107
<212> TYPE: PRT
<213> ORGANISM: Artificial Sequence
<220> FEATURE:
<223> OTHER INFORMATION: light chain KM

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Val Tyr
            20                  25                  30

Leu Ser Trp Phe Gln Gln Lys Pro Gly Lys Ala Ile Lys Arg Leu Ile
        35                  40                  45

Tyr Gly Ala Phe Ser Leu Gln Ser Gly Val Pro Ser Arg Phe Ser Gly
    50                  55                  60

Ser Arg Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Val Arg Tyr Pro Trp
                85                  90                  95

Thr Phe Gly Gly Gly Thr Lys Val Glu Ile Lys
            100                 105


<210> SEQ ID NO 19
<211> LENGTH: 480
<212> TYPE: PRT
<213> ORGANISM: Artificial Sequence
<220> FEATURE:
<223> OTHER INFORMATION: TBL-110 heavy chain variable region

<400> SEQUENCE: 19

Met Gly Trp Ser Cys Ile Ile Leu Phe Leu Val Ala Thr Ala Thr Gly
1               5                   10                  15

Val His Ser Glu Val Gln Val Val Glu Ser Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Tyr Ala Met Asn Trp Val Arg Gln Ala Pro Gly Lys Gly Leu
    50                  55                  60

Glu Trp Val Ala Arg Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Val Tyr Leu Gln Met Asn Asn Leu Lys Thr Glu Asp Thr
            100                 105                 110

Ala Met Tyr Tyr Cys Val Gly Gly Gly Asp Phe Trp Gly Gln Gly Thr
        115                 120                 125

Ala Leu Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175
```

-continued

```
Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

Gly Gly Gly Ser Thr His Arg Pro Pro Met Trp Ser Pro Val Trp Pro
465                 470                 475                 480


<210> SEQ ID NO 20
<211> LENGTH: 1467
<212> TYPE: DNA
<213> ORGANISM: Artificial Sequence
<220> FEATURE:
<223> OTHER INFORMATION: TBL-110 heavy chain variable region

<400> SEQUENCE: 20

gaattcccgc cgccaccatg ggctggtcct gcatcatcct gtttctggtg gccacagcca      60

caggcgtgca ctctgaagtg caggtcgtgg aatctggcgg aggactggtt cagcctaagg     120

gcagcctgaa gctgtcttgt gccgccagcg gcttcacctt caacacctac gccatgaact     180

gggtccgaca ggcccctggc aaaggccttg aatgggtcgc cagaatcaga agcaagagca     240

acaattacgc cacctactac gccgacagcg tgaaggacag attcaccatc agccgggacg     300

acagccagag catggtgtac ctgcagatga acaacctgaa aaccgaggac accgccatgt     360
```

-continued

```
actactgtgt cggcggaggc gatttttggg gccagggaac agctctgaca gtgtccagcg    420
cctctacaaa gggccctagc gttttcccac tggctcccag cagcaagtct acaagcggag    480
gaacagccgc tctgggctgc ctggtcaagg attactttcc cgagcctgtg accgtgtcct    540
ggaatagcgg agcactgaca agcggcgtgc acacctttcc agctgtgctg caaagcagcg    600
gcctgtactc tctgagcagc gtggtcacag tgcctagctc tagcctgggc acccagacct    660
acatctgcaa tgtgaaccac aagcctagca acaccaaggt ggacaagaag gtggaaccca    720
agagctgcga caagacccac acctgtcctc catgtcctgc tccagaactg ctcggcggac    780
cttccgtgtt cctgtttcct ccaaagccta aggataccct gatgatcagc agaacccctg    840
aagtgacctg cgtggtggtg gatgtgtccc acgaggatcc cgaagtgaag ttcaattggt    900
acgtggacgg cgtggaagtg cacaacgcca agaccaagcc tagagaggaa cagtacaaca    960
gcacctacag agtggtgtcc gtgctgaccg tgctgcacca ggattggctg aacggcaaag   1020
agtacaagtg caaggtgtcc aacaaggccc tgcctgctcc tatcgagaaa accatcagca   1080
aggccaaggg ccagcctagg gaaccccagg tttacacact gcctccaagc agggacgagc   1140
tgaccaagaa tcaggtgtcc ctgacctgcc tcgtgaaggg cttctaccct tccgatatcg   1200
ccgtggaatg ggagagcaat ggccagcctg agaacaacta caagacaacc cctcctgtgc   1260
tggacagcga cggctcattc ttcctgtaca gcaagctgac agtggacaag tccagatggc   1320
agcagggcaa cgtgttcagc tgcagcgtga tgcacgaggc cctgcacaac cactacaccc   1380
agaagtccct gagcctgtct ccaggcaaag gcggcggatc tacacacaga cctccaatgt   1440
ggtccccagt gtggccttga taagctt                                       1467
```

<210> SEQ ID NO 21
<211> LENGTH: 233
<212> TYPE: PRT
<213> ORGANISM: Artificial Sequence
<220> FEATURE:
<223> OTHER INFORMATION: TBL-110 light chain variable region

<400> SEQUENCE: 21

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Leu Gly Glu Arg Val Ser Leu Thr Cys Arg Ala Ser Gln Glu Ile
        35                  40                  45

Ser Val Tyr Leu Ser Trp Phe Gln Gln Lys Pro Asp Gly Thr Ile Lys
    50                  55                  60

Arg Leu Ile Tyr Gly Ala Phe Thr Leu Asp Ser Gly Val Pro Lys Arg
65                  70                  75                  80

Phe Ser Gly Ser Arg Ser Gly Ser Asp Tyr Ser Leu Thr Ile Ser Ser
                85                  90                  95

Leu Glu Ser Glu Asp Phe Ala Asp Tyr Tyr Cys Leu Gln Tyr Val Arg
            100                 105                 110

Tyr Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
```

```
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 22
<211> LENGTH: 726
<212> TYPE: DNA
<213> ORGANISM: Artificial Sequence
<220> FEATURE:
<223> OTHER INFORMATION: TBL-110 light chain variable region

<400> SEQUENCE: 22

gaattcccgc cgccaccatg ggctggtcct gcatcatcct gtttctggtg gccacagcca     60

caggcgtgca cagcgatatc cagatgacac agagccccag cagcctgtct gcctctctgg    120

gagaaagagt gtccctgacc tgcagagcca gccaagagat cagcgtgtac ctgagctggt    180

tccagcagaa gcctgacggc accatcaagc ggctgatcta cggcgccttc acactggata    240

gcggcgtgcc caagagattc tccggcagca gatctggcag cgactacagc ctgacaatca    300

gctccctgga aagcgaggac ttcgccgact actactgcct gcagtacgtg cgctacccct    360

ggacatttgg cggcggaaca aagctggaaa tcaagcggac agtggccgct cctagcgtgt    420

tcatctttcc acctagcgac gagcagctga agtctggcac agcctctgtc gtgtgcctgc    480

tgaacaactt ctaccccaga gaagccaagg tgcagtggaa ggtggacaac gccctgcagt    540

ccggcaatag ccaagagtct gtgaccgagc aggacagcaa ggactccacc tatagcctga    600

gcagcaccct gacactgagc aaggccgact acgagaagca caaagtgtac gcctgcgaag    660

tgacccacca gggcctttct agccctgtga ccaagagctt caaccggggc gaatgttgat    720

aagctt                                                               726


<210> SEQ ID NO 23
<211> LENGTH: 87
<212> TYPE: PRT
<213> ORGANISM: Artificial Sequence
<220> FEATURE:
<223> OTHER INFORMATION: TBL-110 heavy chain variable region

<400> SEQUENCE: 23

Glu Val Gln Val Val Glu Ser Gly Gly Gly Leu Val Gln Pro Lys Gly
1               5                   10                  15

Ser Leu Lys Leu Ser Cys Ala Ala Ser Gly Phe Thr Phe Asn Trp Val
            20                  25                  30

Arg Gln Ala Pro Gly Lys Gly Leu Glu Trp Val Ala Arg Phe Thr Ile
        35                  40                  45

Ser Arg Asp Asp Ser Gln Ser Met Val Tyr Leu Gln Met Asn Asn Leu
    50                  55                  60

Lys Thr Glu Asp Thr Ala Met Tyr Tyr Cys Val Gly Trp Gly Gln Gly
65                  70                  75                  80

Thr Ala Leu Thr Val Ser Ser
                85
```

```
<210> SEQ ID NO 24
<211> LENGTH: 345
<212> TYPE: DNA
<213> ORGANISM: Artificial Sequence
<220> FEATURE:
<223> OTHER INFORMATION: TBL-100 high chain variable region

<400> SEQUENCE: 24

gaggtgcagg ttgttgagtc tggtggagga ttggtgcagc ctaaagggtc attgaaactc      60

tcatgtgcag cctctggatt caccttcaat acctacgcca tgaactgggt ccgccaggct     120

ccaggaaagg gtttggaatg ggttgctcgc ataagaagta aaagtaataa ttatgcgaca     180

tattatgccg attcagtgaa agacaggttc accatctcca gagatgattc acaaagcatg     240

gtatatctgc aaatgaacaa cttgaaaact gaggacacag ccatgtatta ttgtgtggga     300

gggggtgact tctggggcca aggcaccgct ctcacagtct cctca                     345


<210> SEQ ID NO 25
<211> LENGTH: 387
<212> TYPE: DNA
<213> ORGANISM: Artificial Sequence
<220> FEATURE:
<223> OTHER INFORMATION: TBL-100 light chain variable region

<400> SEQUENCE: 25

atggacatga gggttcctgc tcacgttttt ggcttcttgt tgctctggtt tccaggtacc      60

agatgtgaca tccagatgac ccagtctcca tcctccttat ctgcctctct gggagaaaga     120

gtcagtctca cttgtcgggc aagtcaggaa attagtgttt acttaagctg gtttcagcag     180

aaaccagatg gaactattaa acgcctgatc tacggcgcat tcactttaga ttctggtgtc     240

ccaaaaaggt tcagtggcag taggtctggg tcagattatt ctctcaccat cagcagcctt     300

gagtctgaag attttgcaga ctattactgt ctacaatatg ttaggtatcc gtggacgttc     360

ggtggaggca ccaagttgga aatcaaa                                          387


<210> SEQ ID NO 26
<211> LENGTH: 461
<212> TYPE: PRT
<213> ORGANISM: Artificial Sequence
<220> FEATURE:
<223> OTHER INFORMATION: TBL-110 heavy chain variable region

<400> SEQUENCE: 26

Glu Val Gln Val Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Val Tyr Leu Gln Met Asn Asn Leu Lys Thr Glu Asp Thr Ala Met Tyr
                85                  90                  95

Tyr Cys Val Gly Gly Gly Asp Phe Trp Gly Gln Gly Thr Ala Leu Thr
            100                 105                 110

Val Ser Ser Ala Ser Thr Lys Gly Pro Ser Val Phe Pro Leu Ala Pro
        115                 120                 125
```

-continued

```
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Ser Thr His Arg Pro Pro Met Trp Ser Pro Val Trp Pro
    450                 455                 460
```

<210> SEQ ID NO 27
<211> LENGTH: 214
<212> TYPE: PRT
<213> ORGANISM: Artificial Sequence
<220> FEATURE:
<223> OTHER INFORMATION: TBL-110 light chain variable region

<400> SEQUENCE: 27

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Val Tyr
            20                  25                  30
```

-continued

```
Leu Ser Trp Phe Gln Gln Lys Pro Asp Gly Thr Ile Lys Arg Leu Ile
        35                  40                  45

Tyr Gly Ala Phe Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Val Arg Tyr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 28
<211> LENGTH: 7
<212> TYPE: PRT
<213> ORGANISM: Artificial Sequence
<220> FEATURE:
<223> OTHER INFORMATION: transport peptide

<400> SEQUENCE: 28

His Ala Ile Tyr Pro Arg His
1               5
```

FUSION CONSTRUCTS AND USES THEREOF

This application claims the benefit of U.S. Provisional Application No. 62/829,776, filed on Apr. 5, 2019, hereby incorporated by reference.

BACKGROUND OF THE INVENTION

Many antibodies have been developed to treat central nervous system (CNS) disorders. However, to date there are no US Food and Drug Administration-approved monoclonal antibodies that show efficacy in the brain following systemic administration. A major reason is likely due to the fact that the biological activity of therapeutic monoclonal antibodies and other recombinant protein therapeutics is limited by their ability to cross the blood-brain barrier ("BBB").

The "blood-brain barrier" is a term used to describe the unique properties of the microvasculature of brain. Brain blood vessels are continuous non-fenestrated vessels, but also contain a series of additional properties that allow them to tightly regulate the movement of molecules, ions, and cells between the blood and the brain. This heavily restricting barrier capacity allows BBB endothelial cells to tightly regulate CNS homeostasis, which is critical to allow for proper neuronal function, as well as protect the CNS from toxins, pathogens, inflammation, injury, and disease. However, the restrictive nature of the BBB, also provides an obstacle for drug delivery to the CNS, especially for large proteins such as antibodies. Typically, less than 0.1% of the injected dose of IgG reaches the brain after peripheral administration, and it is difficult to achieve sufficient concentrations of antibodies in the brain to produce a therapeutic response. The development of antibodies that are able to penetrate the brain at pharmacologically relevant levels is a key therapeutic goal for the treatment of many CNS disorders.

Various methods have been investigated to improve brain exposure to various types of biologics, including antibodies, and avoid the need for direct injection into the cerebrospinal fluid which requires hospitalization of the patient, is highly invasive and can easily cause infection. The most direct approach is to disrupt the tight junctions to allow for paracellular passage. However, this is an unselective procedure for the entry of large molecules as it allows entrance not only for the therapeutic agent but also for other blood components that could be harmful to the brain environment. A similar approach is to use mannitol, an osmotic agent that causes shrinkage of the brain endothelial cells. However, this agent induces rapid, widespread BBB opening and exposes the brain tissue to potentially toxic components of the circulatory system. Another similar approach is the use of focused ultrasound. This is a method of transiently increasing permeability of the BBB at specific brain regions, but again allows non-selective crossing of the BBB and therefore exposure to potentially harmful blood-borne substances.

Macromolecules such as monoclonal antibodies ("mAbs") can utilize three types of vesicle to traverse brain endothelial cells: (i) clathrin-coated vesicles, (ii) caveolae domains generated from lipid rafts, and (iii) macropinocytotic vesicle. For transcytosis of large molecules, which primarily uses clathrin-coated vesicles, a receptor is required for uptake and trafficking across the brain endothelial cells. This process has been termed "receptor-mediated transcytosis" ("RMT"). This is the only known vesicular system that is selective in cargo delivery as it is coordinated by a specific receptor upon binding. This inherent selectivity is highly advantageous and therefore most attempts to transport large molecules across the BBB have used RMT-based approaches, for example by using transferrin-containing nanoparticles or bispecific antibodies comprised of an arm against the receptor and a second against the therapeutic target.

As multimeric proteins, comprised of more than one polypeptide chain linked together by disulphide bonds, antibodies present special challenges with respect to RMT and transport through the BBB.

Bispecific antibodies using RMT have only resulted in relatively modest increase in the amount of mAb reaching the brain parenchyma, in most cased to the level of about 1% of the injected amount. Moreover, monovalent antibodies may reduce efficacy against the therapeutic target. Additionally, bispecific antibodies add significantly to the complexity of development and to the cost of manufacture. It would be desirable to have a method that does not require an antibody ligand to the receptor (i.e., the arm against the receptor of the bispecific antibody) and that does not interfere with the binding of the natural ligand, for example, binding of transferrin to the transferrin receptor since this could interfere with the physiological transport function of the receptor, which in the case of transferrin is to transport iron.

Importantly, papers based on cellular and in vivo data describe the importance of the mode of BBB receptor engagement where avidity (Wiley et al., 2013), affinity (Bien-Ly et al., 2014) and valency (Niewoehner et al., 2014) of the antibody have a profound effect on the transport efficiency across the brain endothelial cells. Data also indicate that endogenous ligand binding might influence the receptor differently compared with an engineered mAb, which may bind to a different epitope. These papers provide strong evidence that engagement with transcytosis receptors, directly influences the intracellular sorting, which in certain formats, leads to unproductive transport and entrapment within the endosomal system of the brain endothelial cells. This unproductive crossing of the BBB has been described using traditional mAbs (Moos and Morgan, 2001; Manich et al., 2013). Thus, the initial interaction between the ligand and the receptor at the BBB lumen determines the fate of the internalized complex. These findings highlight the need to understand the intracellular trafficking of the ligand-cargo receptor complex in order to generate constructs that will successfully be sorted through the brain endothelial cells to the parenchyma space of the brain.

When studying macromolecule transcytosis, the BBB has been regarded as a "black box", with very little attention in trying to understand the intracellular trafficking across brain endothelial cells. Thus, the regulation of intracellular transport through the transcytosis pathway in brain endothelial cells remains largely unexplored.

SUMMARY OF THE INVENTION

It is an object of the invention to provide methods of delivering proteins across the BBB.

It is a further object of the invention to provide methods of delivering peptides across the BBB.

It is an additional object of the invention to provide methods of delivering antibodies across the BBB.

It is an additional object of the invention to provide methods of delivering non-antibody proteins across the BBB.

It is an additional object of the invention to provide fusion constructs for use in drug discovery, diagnosis, prevention and treatment of diseases.

It is yet an additional object of the invention to provide a synthetic fusion peptide that does not compete with transferrin (so should not interfere with iron transport) and avoids the complexity and cost associated with the development and manufacture of bispecific antibodies.

It is a further object of the invention to provide a peptide or protein (e.g., an antibody) fused to an amino acid sequence THRPPMWSPVWP (SEQ ID NO: 2), amino acid sequence HRPPMWSPVWP (SEQ ID NO: 3), amino acid sequence THRPPMWSPVW (SEQ ID NO: 4), amino acid sequence HRPPMWSPVW (SEQ ID NO: 5), or amino acid sequence HAIYPRH (SEQ ID NO: 28) at their carboxyl-termini or amino-termini.

In furtherance of the above objects and others, the present invention is directed in part to fusion constructs comprising a peptide or protein (e.g., an antibody) fused, directly or through a linker, to a peptide containing or consisting of amino acid sequence THRPPMWSPVWP (SEQ ID NO: 2), amino acid sequence HRPPMWSPVWP (SEQ ID NO: 3), amino acid sequence THRPPMWSPVW (SEQ ID NO: 4), amino acid sequence HRPPMWSPVW (SEQ ID NO: 5), or amino acid sequence HAIYPRH (SEQ ID NO: 28) at their carboxyl-termini or amino-termini. Amino acid sequence THRPPMWSPVWP (SEQ ID NO: 2), amino acid sequence HRPPMWSPVWP (SEQ ID NO: 3), amino acid sequence THRPPMWSPVW (SEQ ID NO: 4), amino acid sequence HRPPMWSPVW (SEQ ID NO: 5), and amino acid sequence HAIYPRH (SEQ ID NO: 28) modulates transport of the peptide or protein through the BBB and/or release of the peptide or protein at the abluminal side of the BBB. As compared to the unmodified peptide or protein, the fusion construct may (i) evade entrapment by or degrade at a slower rate in the endothelial endosomal-lysosomal system and/or (ii) have an improved BBB permeability, and/or (iii) have an improved brain retention. The fusion constructs may be used in drug discovery, diagnosis, prevention and treatment of diseases. The fusion construct may also be used in diagnostic assays and/or included as part of kits.

As compared to the unmodified peptide or protein, which is poorly taken up and then rapidly cleared by the lysosomal system, the fusion construct evades entrapment and/or degradation in the lysosomal system, and is released on the abluminal surface after the post-luminal surface uptake. The fusion construct may therefore provide a higher concentration of the peptide or protein, including diagnostic and therapeutic antibodies, in the brain (e.g., at about 3 hours, 6 hours, about 7 hours, about 8 hours, about 9 hours, about 10 hours, about 12 hours, about 16 hours, about 18 hours, about 20 hours, about 22 hours, about 24 hours, etc.) from the time of exposure of the fusion construct to the BBB and/or a longer exposure to the fusion construct (e.g., at least about 10% longer), due to a reduced clearance or entrapment of the fusion construct by, e.g., lysosomes, as compared to an equal dose of the unmodified peptide or protein. Thus, the fusion construct may have a lower effective therapeutic dose than the unmodified peptide or protein.

In addition, as compared to the unmodified peptide or protein, the fusion construct of the invention are not substantially entrapped in the endosomal-lysosomal system and are released on the abluminal surface of the BBB.

The invention is specifically directed to a fusion construct of Formula I:

M-L-C (Formula I), wherein M is a peptide or protein,

L is an optional linker, and

C is a peptide containing or consisting of SEQ ID NO: 2, SEQ ID NO: 3, SEQ ID NO: 4, SEQ ID NO: 5, or SEQ ID NO: 28. M may be fused, directly or through L, to C at its carboxyl-termini or amino-termini, or both, and either bivalently or monovalently. M may have, e.g., a molecular weight of from about 2 kDa to about 30 kDa, 40 kDa to about 900 kDa, from about 50 kDa to about 800 kDa, from about 60 kDa to about 700 KDa, from about 70 kDa to about 600 kDa, from about 80 kDa to about 500 kDa, from about 90 kDa to about 400 kDa, from about 100 kDa to about 350 kDA, from about 100 kDa to about 300 kDa, from about 100 kDa to about 250 kDa, or from about 100 kDa to about 200 kDa. L may, e.g., be a peptide of sequence GGGS (SEQ ID NO: 6), or may be absent. The fusion construct preferably (i) avoids entrapment and degrades at a slower rate in the endothelial endosomal-lysosomal system than M that is not linked to the peptide containing or consisting of SEQ ID NO: 2, SEQ ID NO: 3, SEQ ID NO: 4, SEQ ID NO: 5, or SEQ ID NO: 28, and/or (ii) has an improved blood-brain barrier permeability than M that is not linked to the peptide containing or consisting of SEQ ID NO: 2, SEQ ID NO: 3, SEQ ID NO: 4, SEQ ID NO: 5, or SEQ ID NO: 28, and/or (iii) has an improved brain retention than M that is not linked to the peptide containing or consisting of SEQ ID NO: 2, SEQ ID NO: 3, SEQ ID NO: 4, SEQ ID NO: 5, or SEQ ID NO: 28. In certain embodiments, M may, e.g., be an antibody or a non-antibody protein targeting full length or post-translationally modified tau protein; the antibody and the non-antibody protein may be therapeutic and used, e.g., for treatment of a tauopathy (e.g., Alzheimer's disease (AD), Pick's disease (PiD), progressive supranuclear palsy (PSP), corticobasal degeneration (CBD), frontotemporal lobar degeneration (FTLD), frontotemporal dementia (FTD), Parkinson's disease, traumatic brain injury (TBI), and the like), another neurodegenerative diseases in which tau pathology is implicated (e.g., Parkinson's disease, multiple sclerosis and amyotrophic lateral sclerosis), and age related cognitive impairment; or diagnostic and used in in vivo and/or in vitro assays and kits.

In an additional aspect, the invention is directed to a fusion construct of Formula I:

M-L-C (Formula I), wherein M is selected from the group consisting of antibodies, adnectins, pronectins, affibodies, affilins, anticalins, atrimers, avimers, DARPins, fynomers, knottins, Kunitz domains, β-Hairpin mimetics, bicyclic peptides, and other non-antibody proteins; L is absent or an optional linker (e.g., a peptide of sequence GGGS (SEQ ID NO: 6)), and C is a peptide containing or consisting of SEQ ID NO: 2, SEQ ID NO: 3, SEQ ID NO: 4, SEQ ID NO: 5, or SEQ ID NO: 28. The fusion construct preferably (i) avoids entrapment and degrades at a slower rate in the endothelial endosomal-lysosomal system than M that is not linked to the peptide containing or consisting of SEQ ID NO: 2, SEQ ID NO: 3, SEQ ID NO: 4, SEQ ID NO: 5, or SEQ ID NO: 28, and/or (ii) has an improved blood-brain barrier permeability than M that is not linked to the peptide containing or consisting of SEQ ID NO: 2, SEQ ID NO: 3, SEQ ID NO: 4, SEQ ID NO: 5, or SEQ ID NO: 28, and/or (iii) has increased brain retention than M that is not linked to the peptide containing or consisting of SEQ ID NO: 2, SEQ ID NO: 3, SEQ ID NO: 4, SEQ ID NO: 5, or SEQ ID NO: 28. M may, e.g., be an antibody, and the amino-terminus of the peptide SEQ ID NO: 2, SEQ ID NO: 3, SEQ ID NO: 4, SEQ ID NO: 5, or SEQ ID NO: 39 is fused directly to either the carboxyl-terminus or the amino-terminus of light and/or heavy chain of the antibody, either bivalently or monovalently. In other words, the amino-terminus of the peptide SEQ ID NO: 2, SEQ ID NO: 3, SEQ ID NO: 4, SEQ ID NO: 5, or SEQ ID NO: 28 be fused to the carboxyl-terminus of the heavy chain of the antibody, or the amino-terminus of the peptide SEQ ID NO: 2, SEQ ID NO: 3, SEQ ID NO: 4, SEQ ID NO: 5, or SEQ ID NO:39 may be fused to both the carboxyl-terminus and the amino-terminus of light or heavy chain of the antibody, either bivalently or monovalently. The antibody may comprise (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9); and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12). Thus, the antibody may comprise (a) a heavy chain variable region comprising CDR1 identical to sequence GFTFNTYA (SEQ ID NO: 7), CDR2 identical to IRSKSNNYAT (SEQ ID NO: 8), and CDR3 identical to VGGGDF (SEQ ID NO: 9); and (b) a light chain variable region comprising CDR1 identical to sequence QEISVY (SEQ ID NO: 10), CDR2 identical to sequence GAF (SEQ ID NO: 11), and CDR3 identical to sequence LQYVRYPWT (SEQ ID NO: 12). The antibody may also comprise (a) a heavy chain variable region comprising CDR1 homologous to sequence GFTFNTYA (SEQ ID NO: 7), CDR2 homologous to IRSKSNNYAT (SEQ ID NO: 8), and CDR3 homologous to VGGGDF (SEQ ID NO: 9); and (b) a light chain variable region comprising CDR1 homologous to sequence QEISVY (SEQ ID NO: 10), CDR2 homologous to sequence GAF (SEQ ID NO: 11), and CDR3 homologous to sequence LQYVRYPWT (SEQ ID NO: 12). The antibody may have a binding affinity (KD) for TauC3 of from $1\times10^{-9}$ to $1\times10^{-12}$ and an off-rate (Kd) of $1\times10^{-3}$ or less (e.g., from $1\times10^{-4}$ to $1\times10^{-2}$ s-1), and a binding affinity (KD) for SEQ ID NO:1 of from $1\times10^{-4}$ to $1\times10^{-8}$ M, or no detectable binding with SEQ ID NO:1. In certain embodiments, the antibody shows no detectable binding with SEQ ID NO: 1. The fusion constructs may be used in drug discovery, diagnosis, prevention and treatment of diseases. In certain embodiments, C has cross species reactivity and promotes transcytosis of the fusion construct in different species, including, e.g., humans, monkeys and mouse. In these embodiments, fusion constructs' cross reactivity in different species allows, e.g., for uses of the fusion constructs in pharmacokinetic (PK) and pharmacodynamic (PD) studies in animal models and subsequent extrapolation of the results of studies in animal models to humans.

The invention is specifically directed to a fusion construct of Formula II:

A-L-C (Formula II), wherein A is an antibody,

L is an optional linker, and

C is a peptide containing or consisting of SEQ ID NO: 2, SEQ ID NO: 3, SEQ ID NO: 4, SEQ ID NO: 5, or SEQ ID NO: 28. A may be fused to C at its carboxyl-termini or amino-termini of a light chain, a heavy chain, or both, directly or through L, and either monovalently or bivalently. L may, e.g., be a peptide of SEQ ID NO: 6. The antibody may have, e.g., a molecular weight of from about 40 kDa to about 900 kDa, from about 50 kDa to about 800 kDa, from about 60 kDa to about 700 KDa, from about 70 kDa to about 600 kDa, from about 80 kDa to about 500 kDa, from about 90 kDa to about 400 kDa, from about 100 kDa to about 350 kDA, from about 100 kDa to about 300 kDa, from about 100 kDa to about 250 kDa, or from about 100 kDa to about 200 kDa. The fusion construct preferably (i) avoids entrapment and degrades at a slower rate in the endothelial endosomal-lysosomal system than M that is not linked to the peptide containing or consisting of SEQ ID NO: 2, SEQ ID NO: 3, SEQ ID NO: 4, SEQ ID NO: 5, or SEQ ID NO: 28, and/or (ii) has an increased blood-brain barrier permeability than M that is not linked to the peptide containing or consisting of SEQ ID NO: 2, SEQ ID NO: 3, SEQ ID NO: 4, SEQ ID NO: 5, or SEQ ID NO: 28, and/or (iii) has an improved brain retention than M that is not linked to the peptide containing or consisting of SEQ ID NO: 2, SEQ ID NO: 3, SEQ ID NO: 4, SEQ ID NO: 5, or SEQ ID NO: 28. As compared to the unmodified antibody, which may be poorly taken up and then entrapped by the lysosomal system, the fusion construct evades entrapment and/or degradation in the lysosomal system, and is released on the abluminal surface after the post-luminal surface uptake. The fusion construct may therefore provide a higher concentration of the antibody in the brain (e.g., at about 3 hours, 6 hours, about 7 hours, about 8 hours, about 9 hours, about 10 hours, about 12 hours, about 16 hours, about 18 hours, about 20 hours, about 22 hours, about 24 hours, etc.) from the time of exposure of the fusion construct to the BBB and/or a longer exposure to the fusion construct (e.g., at least about 10% longer), due to a reduced clearance or entrapment of the fusion construct by, e.g., lysosomes, as compared to an equal dose of the unmodified peptide or protein. Thus, the fusion construct may have a lower effective therapeutic dose than the unmodified antibody.

The invention is further directed to a fusion construct of Formula III:

T-L-C (Formula III), wherein T is an anti-TauC3 antibody,

L is an optional linker, and

C is a peptide containing or consisting of SEQ ID NO: 2, SEQ ID NO: 3, SEQ ID NO: 4, SEQ ID NO: 5, or SEQ ID NO: 28. L may, e.g., be a peptide of SEQ ID NO: 6. The amino-terminus of the peptide SEQ ID NO: 2, SEQ ID NO: 3, SEQ ID NO: 4, or SEQ ID NO: 5 may be fused, directly or through L, to the carboxyl-terminus or the amino-terminus of heavy or light, or both of T. In some embodiments, the amino terminus of a peptide containing sequence SEQ ID NO: 2, SEQ ID NO: 3, SEQ ID NO: 4, SEQ ID NO: 5, or SEQ ID NO: 28 is fused to the carboxyl-terminus of heavy chain of the anti-TauC3 antibody. The fusion construct preferably retains binding specificity of the anti-tauC3 antibody (i.e., have an equilibrium constant KD to tauC3 of ≥$10^{-9}$M and is from about 2 to about 3 orders of magnitude higher than the antibody's equilibrium constant KD to FLT (SEQ ID NO:1), preferably, about 1000 times higher than FLT (SEQ ID NO:1)). As compared to the anti-TauC3 antibody, the fusion construct may have an improved penetration through the BBB and provide a higher concentration and duration of effect in the brain than an equal dose of anti-TauC3 antibody, due, e.g., to a reduced clearance of the fusion construct by lysosomes. The fusion construct preferably (i) degrades at a slower rate in the endothelial endosomal-lysosomal system than M that is not linked to the peptide containing or consisting of SEQ ID NO: 2, SEQ ID NO: 3, SEQ ID NO: 4, SEQ ID NO: 5, or SEQ ID NO: 28, and/or (ii) has an improved blood-brain barrier permeability than M that is not linked to the peptide containing or consisting of SEQ ID NO: 2, SEQ ID NO: 3, SEQ ID NO: 4, SEQ ID NO: 5, or SEQ ID NO: 28, and/or (iii) has an improved brain retention than M that is not linked to the peptide containing or consisting of SEQ ID NO: 2, SEQ ID NO: 3, SEQ ID NO: 4, SEQ ID NO: 5, or SEQ ID NO: 28. In the preferred embodiments, the antibody retains its binding capability after being subjected to a temperature from about 40° C. to about 67° C. for 10 minutes and also retains its binding capability after incubation in serum (e.g., mouse) at 37° C. for 21 days. The anti-TauC3 antibody may have an aqueous solubility of 50 mg/ml or more (e.g., from about 50 mg/ml to about 200 mg/ml, from about 55 mg/ml to about 180 mg/ml, from about 55 mg/ml to about 170 mg/ml, from about 55 mg/ml to about 150 mg/ml, from about 55 mg/ml to about 140 mg/ml, from about 55 mg/ml to about 130 mg/ml; or from about 100 mg/ml to about 200 mg/ml, from about 100 mg/ml to about 180 mg/ml, from about 100 mg/ml to about 170 mg/ml, from about 100 mg/ml to about 150 mg/ml, from about 100 mg/ml to about 140 mg/ml, or from about 100 mg/ml to about 130 mg/ml).

In certain embodiments, T is an antibody described in U.S. application Ser. No. 16/838,235, filed on Apr. 2, 2020, herein incorporated by reference. In some of these embodiments, the antibody is an extremely potent humanized mAb that targets TauC3, a particularly noxious, nucleating, pretangle, intracellular and preferentially secreted, C-terminally truncated tau fragment ending at aspartate 421 which is highly correlated with cognitive decline in patients with early Alzheimer's disease and present throughout the evolution of neurofibrillary tangles. TauC3 exists in low abundance compared to full-length Tau (FLT) (2N4R) (SEQ ID NO:1) but was shown to exert a disproportionately large pathological effect contributing the majority of tau seeding activity in extracts of Alzheimer's brains. The murine precursor of TBL-100 (i.e., the antibody characterized in Nicholls, S. B., S. L. DeVos, C. Commins, C. Nobuhara, R. E. Bennett, D. L. Corjuc, E. Maury, et al. 2017. "Characterization of TauC3 antibody and demonstration of its potential to block tau propagation." PLoS ONE 12 (5): e0177914. doi:10.1371/journal.pone.0177914, herein incorporated by reference, was shown to block this activity indicating its potential to prevent tau propagation in the brains of patients with Alzheimer's disease.

In some embodiments, the anti-tauC3 antibody, or an antigen-binding fragment thereof, fused to the peptide containing or consisting of SEQ ID NO: 2, SEQ ID NO: 3, SEQ ID NO: 4, SEQ ID NO: 5, or SEQ ID NO: 28 comprises (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9); and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12). In some of these embodiments, the antibody has a binding affinity (KD) for TauC3 of from $1\times10^{-9}$ to $1\times10^{-12}$ and an off-rate ($K_d$) of $1\times10^{-3}$ or less (e.g., from $1\times10^{-4}$ to $1\times10^{-2}$ $s^{-1}$), and a binding affinity (KD) for FLT (SEQ ID NO:1) of from $1\times10^{-4}$ to $1\times10^{-8}$ M, or no detectable binding with (SEQ ID NO:1).

In some embodiments, the anti-TauC3 antibody, or an antigen-binding fragment thereof, fused to the peptide containing or consisting of SEQ ID NO: 2, SEQ ID NO: 3, SEQ ID NO: 4, SEQ ID NO: 5, or SEQ ID NO: 28 comprises:

(a) a variable heavy chain comprising sequence LVQLVESGGGLVQPGGSLKLSCAASGFTFNTYAMNWVRQASGKGLEWVARIRSKSNNYATYYAASVKGRFTISRDDSKSMAYLQMDSLKTEDTAVYYCVGGGDFWGQGTL VTVSS (SEQ ID NO: 13) or a sequence homologous to SEQ ID NO: 13; and (b) the variable light chain comprising a sequence selected from the group consisting of DIQMTQSPSSLSASVGDRVTITCRASQEISVYLGWFQQKPGKAPKRLIYGAFKLQSGV PSRFSGSRSGTEFTLTISSLQPEDFATYYCLQYVRYPWTFGGGTKVEIK (SEQ ID NO: 14) or a sequence homologous to SEQ ID NO: 14, DIQMTQSPSSLSASVGDRVTITCRASQEISVYLGWYQQKPGKAPKRLIYGAFT LQSGVPSRFSGSRSGTEYTLTISSLQPEDFATYYCLQYVRYPWTFGGGTKVEIK (SEQ ID NO: 15) or a sequence homologous to SEQ ID NO: 15, DIQMTQSPSSLSASVGDRVTITCRASQEISVYLGWYQQKPGKAPKRLIYGAFSL QSGVPSRFSGSRSGTEYTLTISSLQPEDFATYYCLQYVRYPWTFGGGTKVEIK (SEQ ID NO: 16) or a sequence homologous to SEQ ID NO: 16, DIQMTQSPSSLSASVGDRVTITCRASQEISVYLGWFQQKPGKAPKRLIYGAFKL QSGVPSRFSGSRSGTEYTLTISSLQPEDFATYYCLQYVRYPWTFGGGTKVEIK (SEQ ID NO: 17) or a sequence homologous to SEQ ID NO: 17, and DIQMTQSPSSLSASVGDRVTITCRASQEISVYLSWFQQKPGKAIKRLIYGAFSL QSGVPSRFSGSRSGTEYTLTISSLQPEDFATYYCLQYVRYPWTFGGGTKVEIK (SEQ ID NO: 18) or a sequence homologous to SEQ ID NO: 18.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 comprises a variable heavy chain ($V_H$) polypeptide of SEQ ID NO: 13 and the variable light chain ($V_L$) polypeptide of SEQ ID NO: 14, SEQ ID NO: 15, SEQ ID NO: 17, or SEQ ID NO: 18.

In some embodiments, the anti-TauC3 antibody, or an antigen-binding fragment thereof, fused to the peptide containing or consisting of SEQ ID NO: 2, SEQ ID NO: 3, SEQ ID NO: 4, SEQ ID NO: 5, or SEQ ID NO: 28 comprises (a) a variable heavy chain ($V_H$) polypeptide comprising CDR1 represented by SEQ ID NO: 7, CDR2 represented by SEQ ID NO: 8, and CDR3 represented by SEQ ID NO: 9, the variable heavy chain ($V_H$) polypeptide possessing at least 70% sequence identity to SEQ ID NO: 13; and (b) a variable light chain ($V_L$) polypeptide comprising CDR1 represented by SEQ ID NO: 10, CDR2 represented by SEQ ID NO: 11, and CDR3 represented by SEQ ID NO: 12, the variable light chain ($V_L$) polypeptide possessing at least 70% sequence identity to SEQ ID NO: 14, SEQ ID NO: 15, SEQ ID NO: 17, or SEQ ID NO: 18.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 is a humanized antibody comprising a $V_L$ chain polypeptide possessing at least 75% sequence identity to SEQ ID NO: 13, and a $V_H$ chain polypeptide possessing at least 75% sequence identity to SEQ ID NO: 14, SEQ ID NO: 15, SEQ ID NO: 17, or SEQ ID NO: 18.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 comprises a $V_L$ chain polypeptide possessing at least 80% sequence identity to SEQ ID NO: 13, and a $V_H$ chain polypeptide possessing at least 80% sequence identity to SEQ ID NO: 14, SEQ ID NO: 15, SEQ ID NO: 17, or SEQ ID NO: 18.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 comprises a $V_L$ chain polypeptide possessing at least 85% sequence identity to SEQ ID NO: 13, and a $V_H$ chain polypeptide possessing at least 85% sequence identity to SEQ ID NO: 14, SEQ ID NO: 15, SEQ ID NO: 17, or SEQ ID NO: 18.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 comprises a $V_L$ chain polypeptide possessing at least 90% sequence identity to SEQ ID NO: 13, and a $V_H$ chain polypeptide possessing at least 90% sequence identity to SEQ ID NO: 14, SEQ ID NO: 15, SEQ ID NO: 17, or SEQ ID NO: 18.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 comprises a $V_L$ chain polypeptide possessing at least 95% sequence identity to SEQ ID NO: 13, and a $V_H$ chain polypeptide possessing at least 95% sequence identity to SEQ ID NO: 14, SEQ ID NO: 15, SEQ ID NO: 17, or SEQ ID NO: 18.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 is a humanized antibody comprising (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9; and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12); and has a binding affinity (KD) for TauC3 of from $1\times10^{-10}$ $1\times10^{-12}$ and an off-rate ($K_d$) of $1\times10^{-3}$ or less (e.g., from $1\times10^{-4}$ to $5.4\times10^{-4}$ or from $5.5\times10^{-4}$ to $1\times10^{-3}$ $s^{-1}$), and a binding affinity (KD) for SEQ ID NO:1 of from $1\times10^{-4}$ to $1\times10^{-8}$M, or no detectable binding with SEQ ID NO:1.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 is a humanized antibody comprising (a) a heavy chain variable region comprising CDR1 homologous to sequence GFTFNTYA (SEQ ID NO: 7), CDR2 homologous to IRSKSNNYAT (SEQ ID NO: 8), and CDR3 represented by VGGGDF (SEQ ID NO: 9; and (b) a light chain variable region comprising CDR1 homologous to sequence QEISVY (SEQ ID NO: 10), CDR2 homologous to sequence GAF (SEQ ID NO: 11), and CDR3 homologous to sequence LQYVRYPWT (SEQ ID NO: 12); and has a binding affinity (KD) for TauC3 of from $1\times10^{-10}$ to $1\times10^{-12}$ and an off-rate ($K_d$) of $1\times10^{-3}$ or less (e.g., from $1\times10^{-4}$ to $5.4\times10^{-4}$ or from $5.5\times10^{-4}$ to $1\times10^{-3}$ $s^{-1}$), and a binding affinity (KD) for SEQ ID NO:1 of from $1\times10^{-4}$ to $1\times10^{-8}$M, or no detectable binding with SEQ ID NO:1.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 is a humanized antibody comprising (a) a heavy chain variable region comprising CDR1 identical to sequence GFTFNTYA (SEQ ID NO: 7), CDR2 identical to IRSKSNNYAT (SEQ ID NO: 8), and CDR3 identical to VGGGDF (SEQ ID NO: 9; and (b) a light chain variable region comprising CDR1 identical to sequence QEISVY (SEQ ID NO: 10), CDR2 identical to sequence GAF (SEQ ID NO: 11), and CDR3 identical to sequence LQYVRYPWT (SEQ ID NO: 12); and has a binding affinity (KD) for TauC3 of from $1\times10^{-10}$ to $1\times10^{-12}$ and an off-rate ($K_d$) of $1\times10^{-3}$ or less (e.g., from $1\times10^{-4}$ to $5.4\times10^{-4}$ or from $5.5\times10^{-4}$ to $1\times10^{-3}$ $s^{-1}$), and a binding affinity (KD) for SEQ ID NO:1 of from $1\times10^{-4}$ to $1\times10^{-8}$M, or no detectable binding with SEQ ID NO:1.

In some embodiments, the anti-TauC3 antibody fused to the peptide containing or consisting of SEQ ID NO: 2, SEQ ID NO: 3, SEQ ID NO: 4, SEQ ID NO: 5, or SEQ ID NO: 28 is a chimeric antibody comprising (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9; and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12); and has a binding affinity (KD) for TauC3 of from $1\times10^{-10}$ to $1\times10^{-12}$ and an off-rate ($K_d$) of $1\times10^{-3}$ or less (e.g., from $1\times10^{-4}$ to $5.4\times10^{-4}$ or from $5.5\times10^{-4}$ to $1\times10^{-3}$ $s^{-1}$), and a binding affinity (KD) for SEQ ID NO:1 of from $1\times10^{-4}$ to $1\times10^{-8}$ M, or no detectable binding with SEQ ID NO:1.

As compared to anti-tauC3 antibody, the fusion construct has an increased penetration across the BBB and/or reduced clearance and/or degradation by the lysosomal and/or endosomal system(s).

In certain embodiments, the antiTauC3 antibody fused to the peptide containing or consisting of SEQ ID NO: 2, SEQ ID NO: 3, SEQ ID NO: 4, SEQ ID NO: 5, or SEQ ID NO: 28 comprises high chain variable region:

```
                                                  (SEQ ID NO: 23)
EVQVVESGGGLVQPKGSLKLSCAASGFTFNWVRQAPGKGLEWVARFTIS
RDDSQSMVYLQMNNLKTEDTAMYYCVGWGQGTALTVSS,
```

and light chain variable region:

(SEQ ID NO: 29)
DIQMTQSPSSLSASLGERVSLTCWFQQKPDGTIKRLIYGVPKRFSGSRS
GSDYSLTISSLESEDFADYYCFGGGTKLEIK.

As compared to anti-tauC3 antibody, the fusion construct has an increased penetration across the BBB and/or reduced clearance and/or degradation by the lysosomal and/or endosomal system(s).

In certain embodiments, the antiTauC3 antibody fused to the peptide containing or consisting of SEQ ID NO: 2, SEQ ID NO: 3, SEQ ID NO: 4, SEQ ID NO: 5, or SEQ ID NO: 28 comprises high chain variable region encoded by:

(SEQ ID NO: 24)
GAGGTGCAGGTTGTTGAGTCTGGTGGAGGATTGGTGCAGCCTAAAGGGT
CATTGAAACTCTCATGTGCAGCCTCTGGATTCACCTTCAATACCTACGC
CATGAACTGGGTCCGCCAGGCTCCAGGAAAGGGTTTGGAATGGGTTGCT
CGCATAAGAAGTAAAAGTAATAATTATGCGACATATTATGCCGATTCAG
TGAAAGACAGGTTCACCATCTCCAGAGATGATTCACAAAGCATGGTATA
TCTGCAAATGAACAACTTGAAAACTGAGGACACAGCCATGTATTATTGT
GTGGGAGGGGGTGACTTCTGGGGCCAAGGCACCGCTCTCACAGTCTCCT
CA, and light chain variable region encoded by:

(SEQ ID NO: 25)
ATGGACATGAGGGTTCCTGCTCACGTTTTTGGCTTCTTGTTGCTCTGGT
TTCCAGGTACCAGATGTGACATCCAGATGACCCAGTCTCCATCCTCCTT
ATCTGCCTCTCTGGGAGAAAGAGTCAGTCTCACTTGTCGGGCAAGTCAG
GAAATTAGTGTTTACTTAAGCTGGTTTCAGCAGAAACCAGATGGAACTA
TTAAACGCCTGATCTACGGCGCATTCACTTTAGATTCTGGTGTCCCAAA
AAGGTTCAGTGGCAGTAGGTCTGGGTCAGATTATTCTCTCACCATCAGC
AGCCTTGAGTCTGAAGATTTTGCAGACTATTACTGTCTACAATATGTTA
GGTATCCGTGGACGTTCGGTGGAGGCACCAAGTTGGAAATCAAA.

As compared to the anti-tauC3 antibody, the fusion construct has an increased penetration across the BBB and/or reduced clearance and degradation by the lysosomal and/or endosomal system(s).

In certain embodiments, the fusion construct comprises SEQ ID NO: 2 fused to either the N- or C-terminus of the anti-tauC3 antibody heavy chain. For example, the fusion construct may comprise heavy chain:

(SEQ ID NO: 26)
EVQVVESGGGLVQPKGSLKLSCAASGFTFNTYAMNWVRQAPGKGLEWVA
RIRSKSNNYATYYADSVKDRFTISRDDSQSMVYLQMNNLKTEDTAMYYC
VGGGDFWGQGTALTVSSASTKGPSVFPLAPSSKSTSGGTAALGCLVKDY
FPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQY

-continued

NSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSL
SPGKGGGSTHRPPMWSPVWP, and light chain:

(SEQ ID NO: 27)
DIQMTQSPSSLSASLGERVSLTCRASQEISVYLSWFQQKPDGTIKRLIY
GAFTLDSGVPKRFSGSRSGSDYSLTISSLESEDFADYYCLQYVRYPWTF
GGGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC.

In certain embodiments, the fusion construct may comprise Fc region that has been modified not to bind Fc-γ receptor, e.g., by introducing the D265A and N297G (DANG) mutations. It was reported that the D265A and N297G (DANG) mutations are efficacious in attenuating effector function in primates.

The fusion constructs of Formulas II and III may be used, e.g., in diagnosis and treatment of various tauopathies, including, e.g., Alzheimer's disease (AD), Pick's disease (PiD), progressive supranuclear palsy (PSP), corticobasal degeneration (CBD), frontotemporal lobar degeneration (FTLD), frontotemporal dementia (FTD), Parkinson's disease, amyotrophic lateral sclerosis (ALS), multiple sclerosis (MS), traumatic brain injury (TBI), and the like. Additionally, the anti-tauC3 fusion constructs of the invention may have utility in other neurodegenerative diseases in which tau pathology is implicated such as Parkinson's disease, multiple sclerosis and amyotrophic lateral sclerosis. Additionally, the anti-tauC3 fusion constructs of the invention may have utility in age related cognitive impairment.

The invention is further directed to a method of improving penetration of a peptide or protein through the BBB comprising fusing the peptide or protein to the a peptide containing SEQ ID NO: 2, SEQ ID NO: 3, SEQ ID NO: 4, SEQ ID NO: 5, or SEQ ID NO: 28, directly or through a linker. The fusion may be at the carboxyl terminus of the peptide or protein, the amino-terminus of the peptide or protein, or an internal sequence of the peptide or protein (provided that it does not interfere with the peptide's or protein's activity and binding.

The invention is further directed to a method of improving blood brain barrier penetration of an antibody comprising fusing carboxyl-terminus of light chain, heavy chain, or both, of the antibody to the amino-terminus of a peptide containing sequence SEQ ID NO: 2, SEQ ID NO: 3, SEQ ID NO: 4, SEQ ID NO: 5, or SEQ ID NO: 28, directly or through a linker.

The invention is further directed to a method of delivering peptides and proteins across the BBB comprising fusing carboxyl-terminus of a peptide or protein to the amino-terminus of a peptide containing SEQ ID NO: 2, SEQ ID NO: 3, SEQ ID NO: 4, SEQ ID NO: 5, or SEQ ID NO:39, directly or through a linker, and placing the resulting fusion construct in contact with the BBB.

The invention is further directed to a method of delivering antibodies across BBB comprising fusing carboxyl-terminus and/or amino-terminus of the light chain, heavy chain (or both) of the antibody to the amino-terminus of a peptide containing SEQ ID NO: 2, SEQ ID NO: 3, SEQ ID NO: 4, SEQ ID NO: 5, or SEQ ID NO: 28, directly or through a linker, and placing the resulting fusion construct in contact with the BBB.

The invention is further directed to a method for improving the efficiency of transcytosis. The method uses a synthetic fusion peptide of Formula I, II, and III that does not compete with transferrin (so should not interfere with iron transport) and avoids the complexity and cost associated with the development and manufacture of bispecific antibodies and avoids use of transferrin.

Definitions

"Antibody" as used herein is meant to include intact molecules (i.e., a full length antibody (IgM, IgG, IgA, IgE)) and fragments thereof, as well as synthetic and biological derivatives thereof, such as for example Fab, (Fab'2), and Fv fragments-free or expressed, e.g., on the surface of filamentous phage on pIII or pVIII or other surface proteins, or on the surface of bacteria, which are capable of binding an antigen. Fab, (Fab'$_2$) and Fv fragments lack the $F_C$ fragments of intact antibody, clear more rapidly from the circulation and may have less non-specific tissue binding of antibody. The antibody may be a monoclonal antibody or a polyclonal antibody. Recombinant antibodies are encompassed by the term "antibody." The term "antibody" further encompasses chimeric and humanized antibodies. The antibody may also be a fully human antibody (e.g., from a transgenic mice or phage).

The term "humanized antibody" as used herein refers to an antibody in which the complementary-determining regions (CDRs) of a mouse or other non-human antibody are grafted onto a human antibody framework. By human antibody framework is meant the entire human antibody excluding the CDRs.

The term "human antibody" as used herein refers to an antibody in which the entire sequence derived from human genetic repertoire (e.g., from a transgenic mice or phage).

The term "TBL-110" means the fusion construct of Example 1.

The terms "TBL-100" and "murine anti-TauC3 antibody" in the present application means "murine anti-Tau3" characterized in Nicholls, S. B., S. L. DeVos, C. Commins, C. Nobuhara, R. E. Bennett, D. L. Corjuc, E. Maury, et al. 2017. "Characterization of TauC3 antibody and demonstration of its potential to block tau propagation." PLoS ONE 12 (5): e0177914. doi:10.1371/journal.pone.0177914.

The term "homologous" as used herein means that that the sequence is at least 80% identical to the sequence it is homologous to, and the polymeric peptide (e.g., an antibody) comprising the homologous sequence(s) has substantially same biological activity as the polymeric peptide comprising the sequence(s) it is homologous to. For example, a humanized antibody comprising (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9); and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12); and an antibody in which one more of CDR sequences are replaced by a homologous sequence(s) both have a binding affinity (KD) for TauC3 of from $1\times10^{-10}$ to $1\times10^{-12}$ and a binding affinity (KD) for SEQ ID NO:1 of from $1\times10^{-4}$ to $1\times10^{-8}$ M, or no detectable binding with SEQ ID NO:1. By definition, homologous antibodies have substantially similar three dimensional shape.

As used herein, "CDR" means "complementary determining region." CDRs may also be referred to as hypervariable regions. Unless otherwise specified, the CDR sequences disclosed herein are defined by IMGT numbering system.

As used herein, "represented by SEQ ID NO:" with reference to the CDR sequence means that the sequence of the CDR is identical or homologous to the recited SEQ ID NO.

The term "chimeric antibody" as used herein refers to an antibody in which the whole of the variable regions of a mouse or rat antibody are expressed along with human constant regions.

As used herein, "light chain" is the small polypeptide subunit of the antibody. A typical antibody comprises two light chains and two heavy chains.

As herein, "an equal dose" means a dose equal in units of weight. For example, "an equal dose" of a 1 mg dose of a protein is a 1 mg dose of the fusion construct.

As used herein, the "heavy chain" is the large polypeptide subunit of the antibody. The heavy chain of an antibody contains a series of immunoglobulin domains, with at least one variable domain and at least one constant domain.

The term "affinity" as used herein refers to the strength with which an antibody molecule binds its epitope, or the strength a non-antibody protein (e.g., affibody) binds its scaffold. The affinity is determined by surface plasmon resonance (SPR).

The term "KD" as used herein refers to the equilibrium dissociation constant (KD=Kd/Ka, wherein Kd is a dissociation rate constant, and Ka is an association rate constant).

The term "pathological tau" encompasses tauC3, fibrils comprising tauC3, and aggregates comprising tauC3 (e.g., a heterogeneous population comprising full-length tau, tau oligomers and/or post-translational modified tau (truncated or phosphorylated). In addition to tauC3, pathological tau may comprise heterogeneous population of full-length tau (e.g., 2N4R), tau oligomers and/or post-translationally modified tau (truncated or hyperphosphorylated).

The term "seeding" refers to the activities that take place intracellularly after tauC3 and/or fibrils comprising tauC3 and/or aggregates comprising tauC3 are taken up by the cell.

The term "adnectin" means a 94-amino-acid thermostable (Tm>80° C.) binding protein fragment derived from the tenth domain of fibronectin type III (10Fn3).

The term "affilin" or "anticalin" means a protein fragment derived from lipocalins.

The term "avimer" means a class of binding protein fragments derived from the A-domain of various cell surface receptors (i.e., the low density-related protein (LRP) and very low density lipoprotein receptor (VLDLR)).

The term "fynomers" mean a protein derived from amino acids 83-156 of the Srchomology 3 (SH3) domain of FYN tyrosine kinase and composed of a pair of anti-parallel beta sheets joined by two flexible loops which are the sites of ligand binding.

The term "knottin" means stable 30-amino-acid protein fold (<4 kDa) composed of three anti-parallel β-strands connected by loops of variable length and multiple disulfide bonds. A subclass of knottin is the cyclotides in which the N- and C-terminus of the protein is joined post-translationally to form a circular molecule.

The term "Affibody" means a protein fragment derived from the Z-domain of the Ig-binding region of *Staphylococcus aureus* protein A which adopt a three-helix bundle motif and contain no cysteines.

The term "β-Hairpin mimetic" means a single β-hairpin motif designed to reproduce the conformational and electronic properties of functional native protein epitopes. (Simeon et al., Protein Cell 2018, 9(1):3-14).

The abbreviations "DARPins" means Designed ankyrin repeat proteins. DARPins are artificial protein scaffolds based on ankyrin repeat (AR) proteins.

The term "TauC3" means C-terminally truncated tau fragment ending at aspartate 421 of htau40 (SEQ ID NO: 1).

As used herein, "FLT" is an abbreviation for full length Tau (i.e., htau40 (SEQ ID NO: 1)).

As used herein, the terms "therapeutically effective amount" and "effective amount" means an amount of a therapeutic agent (e.g., an anti-tauC3 antibody analogue) or composition that leads to a measurable clinical effect in a patient. The effective amount of the therapeutic agent is determined by the circumstances surrounding the case, including the compound administered, the route of administration, the status of the symptoms being treated and similar patient and administration situation considerations among other considerations. An "effective amount" generally comprises from about 0.01 mg/kg to about 100 mg/kg, preferably from 0.5 mg/kg to 20 mg/kg of the antitauC3 antibody analogue described herein. In certain embodiments, an "effective amount" is 1 mg/kg, 3 mg/kg, 4 mg/kg, 6 mg/kg, 8 mg/kg or 10 mg/kg is used. In certain embodiments, greater than about 0.2%, 0.5%, 1%, 2%, 3%, 4%, 5%, 6%, 7%, 8%, 9%, or 10% of the administered dose reaches CSF.

DETAILED DESCRIPTION

Figure 1A:
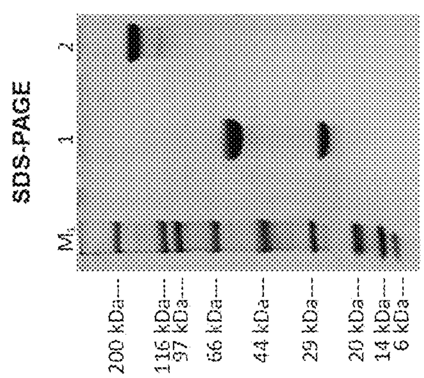
FIG. 1A depicts SDS-Page of the fusion construct of Example 1. Lane M1: Protein Marker, TaKaRa, Cat. No. 3452. Lane 1: Reducing condition. Lane 2: Non-reducing condition.

Short peptides can be fused to the N-terminus or C-terminus of antibody light or heavy chains (or both) without affecting antibody conformation or potency.

"M" of Fusion Constructs of Formula I

In certain embodiments, M of Fusion constructs of Formula I is selected from the group containing or consisting of pronectins (e.g., angiocept), affibodies (e.g., ABY-025, SOBI002, ABY-035), affilins (e.g., PRS-010, PRS-050), anticalins (e.g., PRS-080, PRS-060, PRS-110, PRS-343), atrimers (e.g., ATX 3105), avimers (e.g., AMG220), DARPins (e.g., MP0112, MP0260, MP0250, MP0274), fynomers (e.g., COVA322, COVA208, Knottin, Kuntizt domain), bicyclic peptides, and other non-antibody proteins.

"A" of Fusion Constructs of Formula II

In certain embodiments, A of the fusion construct of Formula II may be selected from the group consisting of U.S. Pat. No. 2,398,852 (Dezamizumab), AAB-001 (Bapineuzumab), ABBV-066 (Risankizumab), ABBV-323, ABBV-323, ABBV-8E12 (C2N 8E12), ABL-001 (Asciminib), ABL301, ABP-710 (Infliximab), ABT-165, ABT-414 (Depatuxizumab), ACZ885 (Canakinumab), ADC-1013, ADCT-402, ALD403 (Eptinezumab), ALX0061 (Vobarilizumab), AMG301 (Aimovig), AMG330, ANB020, ARGX-110, ARGX-111, ASKP1240 (Bleselumab), ATN-103 (Ozoralizumab), BAN0805 (ABBV-0805), BAN2401 (mab158), BAY 1351 (Nerelimomab), B-E8 (Elsilimomab), Bertilimumab, BI 655064, BI 655066, BI 695500, BI 695501, BIM 037 (Aducanumab), BIIB033 (Opicinumab), BIIB054 (Cinpanemab), BIIB074 (Vixotrigine), BIIB076, BMS-936561, Brolucizumab, BT-061 (Tregalizumab), C225 (cetuximab), CAT-192 (Metelimumab), CC-90002 (INBRX-103), CLNH11 (Pritumumab), cmt 412 (Priliximab), DB00028 (Gamunex), DB00073 (Rituximab), DB00095 (Efalizumab), DB00108 (Natalizumab), DB05459 (Briakinumab), DB05656 (Veltuzumab), DB06162 (Lumiliximab), DB06241 (Clenoliximab), DB06606 (Teplizumab), DB06650 (Ofatumumab), DB08935 (Obinutuzumab), DB09052 (Blinatumomab), DB11767 (Sarilumab), DB11803 (Sirukumab), DB11988 (Ocrelizumab), DB12053 (Visilizumab), DB12169 (Tralokinumab), DB12294 (Anrukinzumab), DB12636 (Samalizumab), DB12849 (Clazakizumab), DB13127 (Olokizumab), DB14004 (Tildrakizumab), DB14039 (Erenumab), DB14041 (Fremanezumab), DI-Leu16-IL2), Fazinumab, GC-1008 (Fresolimumab), GSE64382 (Itolizumab), GSK2862277, GSK3050002, GSK3174998, GSK3772847, GZ402668, HLX01, HLX03 (Adalimumab), Herceptin, Humax®-TAC-ADC, Humax-TAC-PBD, Inebilizumab, Inolimomab, IPH33, IPH52, JNJ-63709178, JNJ-63733657, JNJ-64007957, KHK4083, KHK6640, LY2062430 (Solanezumab), LY2599666, LY2951742 (Galcanezumab), LY3303560, MCLA-117, MEDI1341, MEDI1814, MEDI2070 (Brazikumab), MEN112, Mogamulizumab, NEOD001, Nesvacumab, Odulimomab, PF-04360365 (Ponezumab), PMN310, PRX002/R07046015, QAX576, REGN1979, REGN3500, RG1450 (Gantenerumab), RG6026, RG6100, RG6168, RG7412 (Crenzumab), RG7716, RG7828, RG7876, RG7935, RN624 (Tanezumab), RO 7105705, Rontalizumab, RYI 008 (Gerilimzumab), SAR228810, SAR3419 (Coltuximab ravtansine), SAR650984 (Isatuximab), SGN-CD19B, SGN-CD70A, Sym004 (Modotuximab), TAB-107 (Cedelizumab), TAB-262 (Teneliximab), TAB-H16 (Dapirolizumab pegol), TAK-573, TG-110 (Ublituximab), UCB4144, VX15/2503 (Pepinemab), xmab5574 (CD19), Xmab5871, Xoma 052, and (Gevokizumab), and Zanolimumab.

In certain embodiments, A of the fusion construct of Formula II is a monoclonal antibody for treatment of Alzheimer's disease (AD). AD is a chronic neurodegenerative progressive disease that starts with an early onset in a small population with familial genetic causes and later in life for the larger population with no clear genetic basis. The most common symptom associated with this disease is episodic memory loss, progressing to severe cognitive decline. The underlying cause of AD is yet unknown. AD is characterized by the loss of neurons and synapses in the cerebral cortex and certain sub-cortical regions. There is strong genetic evidence that AD is a protein misfolding disorder that results in plaque and tangle deposition of abnormally folded amyloid beta (Aβ) peptide and tau protein in the brain, the two classical hall-marks of the disease (Coate et al., 1991; Hardy and Mullan, 1992). Currently, there is no approved treatment for slowing or arresting disease progression. A seminal study, showed that active immunization against full-length Aβ in combination with an adjuvant reduced amyloid plaque burden in an AD transgenic mouse model (Schenk et al., 1999). Subsequently, numerous studies have demonstrated the efficiency of active and passive Aβ immunotherapy in preclinical AD mouse models. However, despite early optimism derived from these successful preclinical studies, this approach has not yet been developed into disease-modifying therapies in humans. For example, in 2012 two Phase III clinical trials of the anti Aβ Mabs, bapineuzumab and solanezumab, failed to meet their primary clinical end points of improved cognition (Doody et al., 2014; Salloway et al., 2014). Importantly, bapineuzumab caused vascular side effects designated as amyloid-related imaging abnormalities. This resulted in discontinuation of the high-dose group, which may explain the lack of clinical efficacy due to suboptimal brain exposure. In spite of these disappointing clinical results, other mAbs are currently being tested in AD prevention trials, where recent clinical trials have demonstrated that mAbs against the aggregated form of the Aβ peptide produced a dose and time-dependent reduction of amyloid plaque in the brain and potentially also led to clinical benefit. The most promising clinical data have been observed in patients with early (prodromal) or mild AD, suggesting that early intervention is important although in practice it is extremely difficult to find patients at this stage of the disease.

There are several mAbs in human clinical trials with the aim of reaching therapeutic concentrations within the brain parenchyma space to establish clinical benefit with the greatest number being tested in AD.

In certain embodiments, A of the fusion construct of Formula II is selected from the group consisting of solanezumab, aducanumab, gantenerumab, BAN2401, LY3372993, SAR255952, Donanemab (aka N3pG) LY3202626, R07105705, BIIB076, C2N 8E12, LY3303560.

"T" of the Fusion Construct of Formula III

T of the invention encompasses chimeric, humanized and human antibodies that are specific for the C-terminus of TauC3 ("anti-TauC3 antibodies"). The anti-TauC3 antibodies have a binding affinity (KD) for TauC3 of from $1\times10^{-10}$ to $1\times10^{-12}$ and a binding affinity (KD) for full length tau ("FLT") (SEQ ID NO:1) of from $1\times10^{-4}$ to $1\times10^{-8}$ M. For example, the anti-TauC3 antibodies may have a binding affinity (KD) for TauC3 of about $5\times10^{-12}$ M to about $1.2\times10^{-10}$ from about $1\times10^{-11}$ M to about $1\times10^{-10}$ M, from about $1\times10^{-11}$ M to about $9\times10^{-11}$ M, from about $1\times10^{-11}$ M to about $8\times10^{-11}$ M, from about $1\times10^{-11}$ M to about $7\times10^{-11}$ M, from about $1\times10^{-11}$ M to about $6\times10^{-11}$ M, from about $1\times10^{-11}$ M to about $5\times10^{-11}$ M, or from about $1\times10^{-11}$ M to about $4\times10^{-11}$ M; and a binding affinity (KD) for FLT of from $1\times10^{-4}$ to $1\times10^{-8}$ M. In the preferred embodiments, the antibody retains its binding capability after being subjected to a temperature from about 40° C. to about 67° C. for 10 minutes and also retains its binding capability after incubation in serum (e.g., mouse) at 37° C. for 21 days. The high binding capability of the anti-TauC3 antibodies allows the antibodies to target TauC3 without compromising normal physiological functions of FLT. In some embodiments, the specificity of the antibody allows to target only the most noxious species of tau, one may potentially reduce the effective therapeutic dose, as compared to an antibody which is not specific and does not discriminate between different species of tau. The anti-TauC3 antibodies, and their antigen binding fragments, could be used, e.g., in the diagnosis and treatment of neurodegenerative disorders associated with pathological activities of TauC3 in the brain, including, e.g., Alzheimer disease (AD), progressive supranuclear palsy (PSP), frontotemporal dementia (FTD), traumatic brain injury (TBI), Pick's disease (PiD), corticobasal degeneration (CBD), frontotemporal lobar degeneration (FTLD), etc. The anti-TauC3 antibody may have an aqueous solubility of 50 mg/ml or more (e.g., from about 50 mg/ml to about 200 mg/ml, from about 55 mg/ml to about 180 mg/ml, from about 55 mg/ml to about 170 mg/ml, from about 55 mg/ml to about 150 mg/ml, from about 55 mg/ml to about 140 mg/ml, from about 55 mg/ml to about 130 mg/ml; or from about 60 mg/ml to about 130 mg/ml.

In certain embodiments, T of the fusion construct of Formula III is TBL-100 or TauC3 antibody.

Tauopathies

Tau protein (2N4R) (SEQ ID NO: 1), often referred to as full-length tau (FLT), is a microtubule associated protein that distributes mainly to axons. Tau protein takes part in modulating the assembly, spatial organization and behavior of microtubules (MT) in neurons. FLT is preferentially cleaved by caspase-3, at residue 421 near the C-terminus of the protein, forming a truncated form of the protein known as TauC3.

TauC3 exists in low abundance compared to FLT (believed less than 1%) but was shown to exert a disproportionately large pathological effect, accounting, e.g., for the majority of tau propagation in AD brain, presumably by driving tau filament formation by nucleation. TauC3 is an extremely noxious protein. TauC3 is implicated in various tauopathies and neurodegenerative disorders, including, e.g., Alzheimer's disease (AD), Pick's disease (PiD), progressive supranuclear palsy (PSP), corticobasal degeneration (CBD), frontotemporal lobar degeneration (FTLD), frontotemporal dementia (FTD), traumatic brain injury (TBI), and the like. TauC3 may also be implicated, e.g., Parkinson's disease, multiple sclerosis and amyotrophic lateral sclerosis. An SNP (rs1768208 C/T) has been identified as a strong risk factor for PSP and shown to result in increased levels of the pro-apoptotic protein appoptosin in PSP patients. Elevations in appoptosin correlate with activated caspase-3 and tauC3 levels.

Fusion constructs which selectively bind TauC3 and exhibit no substantial binding to FLT (SEQ ID NO:1) may be used to treat various tauopathies, without compromising the physiological function of FLT.

Administration of a fusion construct of Formula III can be used, e.g., as a therapy to treat or immunize from tauopathies.

The fusion construct of Formula III may be administered to a human in a therapeutically effective amount to treat a tauopathy. Administration is performed using standard effective techniques, include peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes, but is not limited to, via a lumbar, intraventricular or intraparenchymal catheter or using a surgically implanted controlled release formulation.

Humans amenable to treatment include individuals at risk of disease but not showing symptoms, as well as patients presently showing symptoms. In the case of Alzheimer's disease, virtually anyone is at risk of suffering from Alzheimer's disease. Therefore, the present methods can be administered prophylactically to the general population. Such prophylactic administration can begin at, e.g., age 50 or greater. The present methods are especially useful for individuals who do have a known genetic risk of a tauopathy (e.g., Alzheimer's disease). Such individuals include those having relatives who have experienced this disease and those whose risk is determined by analysis of genetic or biochemical markers. For example, genetic markers of risk toward Alzheimer's disease include mutations in the APP gene, particularly mutations, at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia by the presence of risk factors described above. In addition, a number of diagnostic tests are available for identifying individuals who have AD. These include imaging, and/or measurement of CSF tau and Aβ42 levels. Elevated tau and decreased Aβ42 levels signify the presence of AD. Individuals suffering from Alzheimer's disease can also be diagnosed by Alzheimer's disease and Related Disorders Association criteria.

In asymptomatic patients, treatment can begin at any age (e.g., 10, 20, 30, 40, 50, or 60). Usually, however, it is not necessary to begin treatment until a patient reaches 40, 50, 60, 70, 75 or 80. Treatment typically entails multiple dosages over a period of time. Treatment can be monitored by assaying antibody, or activated T-cell or B-cell responses to the therapeutic agent over time. If the response falls, a booster dosage is indicated. In the case of potential Down's syndrome patients, treatment can begin antenatally by administering therapeutic agent to the mother or shortly after birth.

In prophylactic applications, pharmaceutical compositions comprising an anti-tau antibody analogue according to the invention are administered to a patient susceptible to, or otherwise at risk of a tauopathy in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions comprising a fusion construct of Formula III are administered to a patient suspected of, or already suffering from, such a disease in an amount sufficient to cure, or at least partially arrest, the symptoms of the disease biochemical, histologic and/or behavioral), including its complications and intermediate pathological phenotypes in development of the disease. In some methods, administration of agent reduces or eliminates mild cognitive impairment. An amount adequate to accomplish therapeutic or prophylactic treatment is defined as a therapeutically- or prophylactically-effective dose or amount. In both prophylactic and therapeutic regimes, agents are usually administered in several dosages until a sufficient immune response has been achieved. Typically, the immune response is monitored and repeated dosages are given if the immune response starts to wane.

Effective doses of the fusion construct of Formula III, for the treatment of the above described conditions vary depending upon many different factors, including means of administration, target site, physiological state of the patient, other medications administered, and whether treatment is prophylactic or therapeutic. Treatment dosages need be tested on a case by case basis in clinical trials and often titrated to optimize safety and efficacy. An additional advantage of the fusion construct of Formula III of the present invention in certain embodiments may be that, for equal mass dosages, dosages of the fusion construct of Formula III contain a higher molar dosage of the antibodies effective in clearing and/or "inactivating," than a composition comprising antibodies that are less specific for tauC3 than the fusion construct of Formula III. Typically, fusion construct of Formula III would be administered by intravenous infusion or subcutaneous injection. The amount of the fusion construct of Formula III for administration by intravenous infusion may vary from 0.5 to 10 mg per patient. Subcutaneous injections generally require higher doses to reach the brain in sufficient quantity. The antibodies (e.g., whole IgG molecules) may be administered once a month.

Dosage and frequency vary depending on the half-life of the fusion construct of Formula III in the patient. In general, fusion constructs comprising humanized antibodies show the longest half-life, followed by fusion constructs comprising chimeric antibodies, and fusion constructs comprising nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In some methods, dosage of the fusion construct is adjusted to achieve a plasma antibody concentration of 1-1000 μg/ml and in some methods 25-300 μg/ml. Alternatively, antibody can be administered as a sustained release formulation, in which case less frequent administration is required.

The dose of the fusion construct of Formula III to block tauC3 seeding is not necessarily the same as the dose of the fusion construct of Formula III to inhibit tauC3 aggregation. In view of the information provided in the present specification, one of ordinary skill in the art can determine the specific doses by routine experimentation.

The efficacy of the administration/treatment may be accessed by measuring levels of pathogenic tau or phospho tau in plasma and/or CSF. Based on this assessment, the dose and/or frequency of administration may be adjusted accordingly.

In certain embodiments, effect on cognition may also be accessed.

The efficacy may also be accessed by a degree of brain atrophy, as determined by MRI.

The safety of the administration/treatment may be accessed by number of participants experiencing adverse events (AEs), serious AEs, and abnormalities in clinical laboratory tests, vital signs, ECGs, MRI, and physical and neurological exams as well as worsening of cognition. Based on this assessment, the dose and/or frequency of administration may be adjusted accordingly.

The fusion construct of Formula III may be administered intranasally, by a subcutaneous injection, intramuscular injection, IV infusion, transcutaneously, buccally, etc., or as described in more detail below.

Methods of Blocking Propagation of Pathological Tau Aggregation

In an additional aspect, the invention is directed to a method of blocking spreading of pathological tau from one neuron to another or from one part of the brain to another.

In an additional aspect, the invention is directed to a method of blocking tauC3 seeding activity in the brain of a patient.

The invention is also directed to a method of reducing the spread of pathological tau aggregation in the brain of a patient.

The invention is further directed to a method of reducing the spread of aggregates comprising tauC3 in the brain of a patient.

The invention is further directed to a method of reducing the spread of fibrils comprising tauC3 in the brain of a patient.

In a further aspect the invention, the invention is directed to a method of reducing intracellular aggregation of tau induced by intracellular uptake of tauC3 and tauC3 fibrils.

In each aspect, the method comprises administering a therapeutically effective amount of a fusion construct of Formula III to a human. The fusion construct of Formula III is capable of uniquely recognizing an aggregated form of pathological tau without significantly affecting normal physiological functions of FLT. In an embodiment, an essential part of the epitope of the fusion construct of Formula III is the carboxy group forming a neoepitope at the C-terminus residue in a peptide corresponding to the last ten C-terminal residues of tauC3 (SEQ ID NO: 18 SSTGSIDMVD). The fusion construct of Formula III preferably has an equilibrium constant KD to tauC3 that is from about 2 to about 3 orders of magnitude higher than the antibodies equilibrium constant KD to FLT (SEQ ID NO:1). The fusion construct of Formula III binds tauC3 with equilibrium constant KD of from $1\times10^{-10}$ M to $1\times10^{-11}$ M, but have an equilibrium constant KD with FLT (SEQ ID NO:1) which is from $1\times10^{-4}$ M to $1\times10^{-8}$ M or show no detectible binding with FLT (SEQ ID NO:1). In the preferred embodiments, the fusion construct of Formula III binds tauC3 with an equilibrium constant KD of from $1\times10^{-11}$ M to $9\times10^{-11}$ M, and bind FLT (i.e., 2N4R) (SEQ ID NO:1) with an equilibrium constant KD of from $1\times10^{-8}$ M to $9\times10^{-8}$M or show no detectable binding with FLT (i.e., 2N4R) (SEQ ID NO:1). The fusion construct of Formula III preferably has a very slow off rate from tauC3 (i.e., an association constant (ka) of from 9,000,000 l/Ms to 14,000,000 l/MS) and substantially no affinity to 2N4R (i.e., ka of less than 100,000 l/MS). The antibodies may, e.g., be a humanized antibody, a chimeric antibody or an immunological fragment of any of the foregoing.

A human may or may not be having a symptom associated with tau aggregation prior to administration of a therapeutically effective amount of the fusion construct of Formula III. In other words, a human may or may not be experiencing a symptom associated with tau seeding and/or aggregation. One of the ordinary skill in the art would appreciate that pathological tau seeding and aggregation likely commences prior to diagnosis or the onset of symptoms associated with tau aggregation. In some embodiments, a human is having a symptom associated with tau seeding and/or aggregation. In other embodiments, a human is not having a symptom associated with tau seeding and/or aggregation. In still other embodiments, a human has detectable tau pathology but is not having any other symptom associated with tau symptoms and/or aggregation. Reducing the spread of tau aggregation in the brain of a human by administering the therapeutic agents and pharmaceutical compositions according to the invention may reduce the development and/or progression of symptoms associated with the pathological seeding and/or aggregation of tau.

Preventing, inhibiting or slowing down spreading of pathological tau aggregation may therefore be used in the treatment of pathologies associated with generation and spread of tau aggregates. Exemplary disorders that have symptoms associated with tau aggregation include, but are not limited to, progressive supranuclear palsy, dementia pugilistica (chronic traumatic encephalopathy), frontotemporal dementia and parkinsonism linked to chromosome 17, Lytico-Bodig disease (Parkinson-dementia complex of Guam), tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, argyrophilic grain disease (AGD), Frontotemporal lobar degeneration, Alzheimer's Disease, and frontotemporal dementia. Methods for diagnosing these disorders are known in the art.

Exemplary symptoms associated with tau seeding or aggregation may include, e.g., impaired cognitive function, altered behavior, emotional dysregulation, seizures, and impaired nervous system structure or function. Impaired cognitive function includes but is not limited to difficulties with memory, attention, concentration, language, abstract thought, creativity, executive function, planning, and organization. Altered behavior includes but is not limited to physical or verbal aggression, impulsivity, decreased inhibition, apathy, decreased initiation, changes in personality, abuse of alcohol, tobacco or drugs, and other addiction-related behaviors. Emotional dysregulation includes but is not limited to depression, anxiety, mania, irritability, and emotional incontinence. Seizures include but are not limited to generalized tonic-clonic seizures, complex partial seizures, and non-epileptic, psychogenic seizures. Impaired nervous system structure or function includes but is not limited to hydrocephalus, Parkinsonism, sleep disorders, psychosis, impairment of balance and coordination. This includes motor impairments such as monoparesis, hemiparesis, tetraparesis, ataxia, ballismus and tremor. This also includes sensory loss or dysfunction including olfactory, tactile, gustatory, visual and auditory sensation. Furthermore, this includes autonomic nervous system impairments such as bowel and bladder dysfunction, sexual dysfunction, blood pressure and temperature dysregulation. Finally, this includes hormonal impairments attributable to dysfunction of the hypothalamus and pituitary gland such as deficiencies and dysregulation of growth hormone, thyroid stimulating hormone, lutenizing hormone, follicle stimulating hormone, gonadotropin releasing hormone, prolactin, and numerous other hormones and modulators. Methods for detecting and evaluating symptoms associated with tau aggregation are known in the art.

In some embodiments, a symptom associated with tau aggregation refers to dementia. Dementia is not itself a specific disease, but is an overall term that describes a wide range of symptoms associated with a decline in memory or other thinking skills severe enough to reduce a person's ability to perform everyday activities. Dementia is also a shared clinical feature of many diseases associated with tau aggregation. A skilled practitioner will be familiar with the numerous methods available to diagnose the severity of dementia. For example, several cognitive tests and screening questionnaires for dementia are known in the art, all with varying degrees of sensitivity and specificity. Non-limiting examples include the mini mental state examination (MMSE), the abbreviated mental test may score (AMTS), the modified mini mental state exam (3MS), the cognitive abilities screening instrument (CASI), the Trail-making test, the clock drawing test, the Informant Questionnaire on cognitive decline in the elderly, the General practitioner assessment of cognition, the Clinical Dementia Rating (CDR), Eight-item informant interview to differentiate aging and dementia (AD8).

In some embodiments, the severity of the symptoms of dementia is quantified using the Clinical Dementia Rating. Using the Clinical Dementia Rating, a score of 0 indicates no symptoms, a score of 0.5 indicates very mild symptoms, a score of 1 indicates mild symptoms, a score of 2 indicates moderate symptoms and a score of 3 indicates severe symptoms. Thus, any increase in a Clinical Dementia Rating score for a human indicates a worsening in cognition and an increase in dementia. Moreover, change in Clinical Dementia Rating from 0 to greater than 0, indicates the development or onset of dementia.

In some embodiments, a symptom associated with tau seeding or aggregation refers to tau pathology or a tauopathy. The term "tau pathology" or "tauopathy" refers to the pathological seeding or aggregation of tau. In some embodiments, tau pathology refers to neurofibrially tangles. In other embodiments, tau pathology refers to hyperphosphorylated tau. In still other embodiments, tau pathology refers to a high level of tau aggregates detectable in blood, plasma, serum, CSF, or ISF, anywhere from 2 to approximately 40-fold higher than that detected in individuals without disease.

Pharmaceutical Compositions

Pharmaceutical compositions in accordance with the invention comprise the fusion construct of Formula I, II or III, and one or more pharmaceutically acceptable excipients.

The fusion construct of Formula III binds tauC3 with equilibrium constant KD of from $1\times10^{-10}$ M to $1\times10^{-11}$ M, but have an equilibrium constant KD with FLT (SEQ ID NO:1) which is from $1\times10^{-4}$ M to $1\times10^{-8}$ M or show no detectible binding with FLT (SEQ ID NO:1). In the preferred embodiments, the fusion construct of Formula III binds tauC3 with an equilibrium constant KD of from $1\times10^{-11}$ M to $9\times10^{-11}$ M, and binds FLT (SEQ ID NO:1) with an equilibrium constant KD of from $1\times10^{-8}$ M to $9\times10^{-8}$ M or show no detectable binding with FLT (SEQ ID NO:1). The fusion construct of Formula III preferably has a very slow off rate from tauC3 (i.e., an association constant (ka) of from 9,000,000 1/Ms to 14,000,000 1/MS) and substantially no affinity to FLT (SEQ ID NO:1) (i.e., ka of less than 100,000 1/MS). A of the fusion construct of Formula III may, e.g., comprise a humanized antibody, a chimeric antibody or a human antibody (e.g., from tg mice).

The pharmaceutical compositions are designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate.

Effective peripheral systemic delivery by intravenous or subcutaneous injection is a preferred method of administration to a living patient. Suitable vehicles for such injections are straightforward.

The concentration of the fusion construct of Formula I, II or III in formulations to be administered is an effective amount and ranges from as low as about 0.1% by weight to as much as about 95% or about 99.9% by weight and will be selected primarily based on fluid volumes, viscosities, and so forth, in accordance with the particular mode of administration selected if desired. In certain embodiments, the fusion construct of Formula I, II or III may comprise from about 15 or about 20% by weight of the composition.

A composition for injection to a patient could be made up to contain from 1-250 ml sterile buffered water of phosphate buffered saline and about 1-5000 mg of any one of or a combination of the fusion construct of Formula I, II or III. The formulation could be sterile filtered after making the formulation, or otherwise made microbiologically acceptable. A typical composition for intravenous infusion could have volumes between 1-250 ml of fluid, such as sterile Ringer's solution, and 1-100 mg per ml, or more in anti-tau antibody analogue concentration. Therapeutic agents of the discovery can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies).

Dosages administered are effective amounts for the purposes indicated and may have to be adjusted to compensate. The pH of the formulations that are generally of pharmaceutical grade quality will be selected to balance antibody stability (chemical and physical) and comfort to the patient when administered. Generally, a pH between 4 and 8 is tolerated. Doses will vary from individual to individual based on size, weight, and other physiobiological characteristics of the individual receiving the successful administration.

In an aspect, a typical dose contains from about 0.1 mg to about 10 mg fusion construct of Formula I, II or III. In certain embodiments, the dose is from about 0.5 mg to about 10 mg. Doses can range from about 0.55 mg/kg to about 10 mg/kg. The frequency of dosing with whole IgG antibodies is usually per month whereas antibody fragments need to be dosed more often in view of their shorter half-life, as needed as to effectively treat the symptoms.

The timing of administration of the treatment relative to the disease itself and duration of treatment will be determined by the circumstances surrounding the case. Treatment could begin after diagnosis of a disease associated with tau aggregation. Alternatively, treatment could begin after clinical confirmation of a symptom associated with tau aggregation. Further still, treatment could begin after detection of tau pathology. Treatment could begin immediately in a hospital or clinic, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of proteins such as humanized antibodies, by suitable adaptation, other effective techniques for administration, such as intraventricular administration, transdermal administration and oral administration may be employed provided proper formulation is utilized herein.

Typical effective amounts or doses can be determined and optimized using standard clinical techniques and will be dependent on the mode of administration in view of the information provided herein and knowledge available in the art.

Example 1 (TBL-110)

A fusion construct was prepared. The heavy and light chain sequences of the fusion construct were as follows:

```
Full length heavy chain:
EcoRI-Kozak sequence-Artificial signal peptide-TAUC3 Heavy chain variable
region-Human IgG1 Constant region (P01857)-linker-peptide-Stop codon-HindIII
Heavy chain sequence: 480aa
                                                          (SEQ ID NO: 19)
MGWSCIILFLVATATGVHS-EVQVVESGGGLVQPKGSLKLSCAASGFTFN-
TYAMN-WVRQAPGKGLEWVA-RIRSKSNNYATYYADSVKD-
RFTISRDDSQSMVYLQMNNLKTEDTAMYYCVG-GGDF-WGQGTALTVSS-
```

-continued

ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK-

GGGS-THRPPMWSPVWP.

DNA sequence: 1467bp (SEQ ID NO: 20)

GAATTC-CC-GCCGCCACC-

ATGGGCTGGTCCTGCATCATCCTGTTTCTGGTGGCCACAGCCACAGGCGTGCA

CTCT-

GAAGTGCAGGTCGTGGAATCTGGCGGAGGACTGGTTCAGCCTAAGGGCAGCC

TGAAGCTGTCTTGTGCCGCCAGCGGCTTCACCTTCAACACCTACGCCATGAAC

TGGGTCCGACAGGCCCCTGGCAAAGGCCTTGAATGGGTCGCCAGAATCAGAA

GCAAGAGCAACAATTACGCCACCTACTACGCCGACAGCGTGAAGGACAGATT

CACCATCAGCCGGGACGACAGCCAGAGCATGGTGTACCTGCAGATGAACAAC

CTGAAAACCGAGGACACCGCCATGTACTACTGTGTCGGCGGAGGCGATTTTTG

GGGCCAGGGAACAGCTCTGACAGTGTCCAGC-

GCCTCTACAAAGGGCCCTAGCGTTTTCCCACTGGCTCCCAGCAGCAAGTCTAC

AAGCGGAGGAACAGCCGCTCTGGGCTGCCTGGTCAAGGATTACTTTCCCGAG

CCTGTGACCGTGTCCTGGAATAGCGGAGCACTGACAAGCGGCGTGCACACCTT

TCCAGCTGTGCTGCAAAGCAGCGGCCTGTACTCTCTGAGCAGCGTGGTCACAG

TGCCTAGCTCTAGCCTGGGCACCCAGACCTACATCTGCAATGTGAACCACAAG

CCTAGCAACACCAAGGTGGACAAGAAGGTGGAACCCAAGAGCTGCGACAAG

ACCCACACCTGTCCTCCATGTCCTGCTCCAGAACTGCTCGGCGGACCTTCCGT

GTTCCTGTTTCCTCCAAAGCCTAAGGATACCCTGATGATCAGCAGAACCCCTG

AAGTGACCTGCGTGGTGGTGGATGTGTCCCACGAGGATCCCGAAGTGAAGTT

CAATTGGTACGTGGACGGCGTGGAAGTGCACAACGCCAAGACCAAGCCTAGA

GAGGAACAGTACAACAGCACCTACAGAGTGGTGTCCGTGCTGACCGTGCTGC

ACCAGGATTGGCTGAACGGCAAAGAGTACAAGTGCAAGGTGTCCAACAAGGC

CCTGCCTGCTCCTATCGAGAAAACCATCAGCAAGGCCAAGGGCCAGCCTAGG

GAACCCAGGTTTACACACTGCCTCCAAGCAGGGACGAGCTGACCAAGAATC

AGGTGTCCCTGACCTGCCTCGTGAAGGGCTTCTACCCTTCCGATATCGCCGTG

GAATGGGAGAGCAATGGCCAGCCTGAGAACAACTACAAGACAACCCCTCCTG

TGCTGGACAGCGACGGCTCATTCTTCCTGTACAGCAAGCTGACAGTGGACAAG

TCCAGATGGCAGCAGGGCAACGTGTTCAGCTGCAGCGTGATGCACGAGGCCC

-continued

TGCACAACCACTACACCCAGAAGTCCCTGAGCCTGTCTCCAGGCAAAGGCGG

CGGATCT-ACACACAGACCTCCAATGTGGTCCCCAGTGTGGCCT-TGA-

TAAGCTT.

Full Length light chain:
EcoRI-Kozak sequence-Artificial signal peptide-TAUC3 Light chain variable region-Human Ig kappa constant region (P01834)-Stop codon-HindIII Light chain sequence: 233aa (SEQ ID NO: 21)

MGWSCIILFLVATATGVHS-DIQMTQSPSSLSASLGERVSLTC-RASQEISVYLS-

WFQQKPDGTIKRLIY-GAFTLDS-GVPKRFSGSRSGSDYSLTISSLESEDFADYYC-

LQYVRYPWT-FGGGTKLEIK-

RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC.

DNA sequence: 726bp (SEQ ID NO: 22)

GAATTC-CC-GCCGCCACC-

ATGGGCTGGTCCTGCATCATCCTGTTTCTGGTGGCCACAGCCACAGGCGTGCACAGC-

GATATCCAGATGACACAGAGCCCCAGCAGCCTGTCTGCCTCTCTGGGAGAAAGAGTGTCCCTGACC

TGCAGAGCCAGCCAAGAGATCAGCGTGTACCTGAGCTGGTTCCAGCAGAAGCCTGACGGCACCAT

CAAGCGGCTGATCTACGGCGCCTTCACACTGGATAGCGGCGTGCCCAAGAGATTCTCCGGCAGCAG

ATCTGGCAGCGACTACAGCCTGACAATCAGCTCCCTGGAAAGCGAGGACTTCGCCGACTACTACTG

CCTGCAGTACGTGCGCTACCCCTGGACATTTGGCGGCGGAACAAAGCTGGAAATCAAG-

CGGACAGTGGCCGCTCCTAGCGTGTTCATCTTTCCACCTAGCGACGAGCAGCTGAAGTCTGGCACA

GCCTCTGTCGTGTGCCTGCTGAACAACTTCTACCCCAGAGAAGCCAAGGTGCAGTGGAAGGTGGAC

AACGCCCTGCAGTCCGGCAATAGCCAAGAGTCTGTGACCGAGCAGGACAGCAAGGACTCCACCTA

TAGCCTGAGCAGCACCCTGACACTGAGCAAGGCCGACTACGAGAAGCACAAAGTGTACGCCTGCG

AAGTGACCCACCAGGGCCTTTCTAGCCCTGTGACCAAGAGCTTCAACCGGGGCGAATGT-TGA-T-

AAGCTT.

Figure 1B:
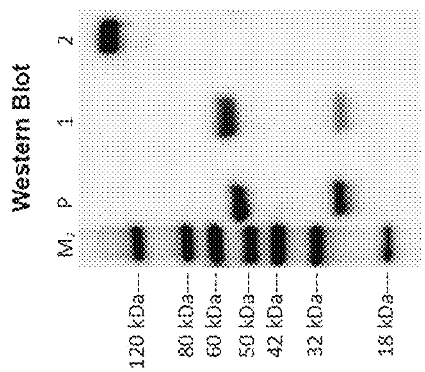
FIG. 1B depicts Western blot analysis of the fusion construct of Example 1. Lane M2: Protein Marker, GenScript, Cat. No. M00521. Lane 1: Reducing condition. Lane 2: Non-reducing condition. Lane P: Human IgG1, Kappa (Sigma, Cat. No. I5154) as a positive control.
Figure 2:
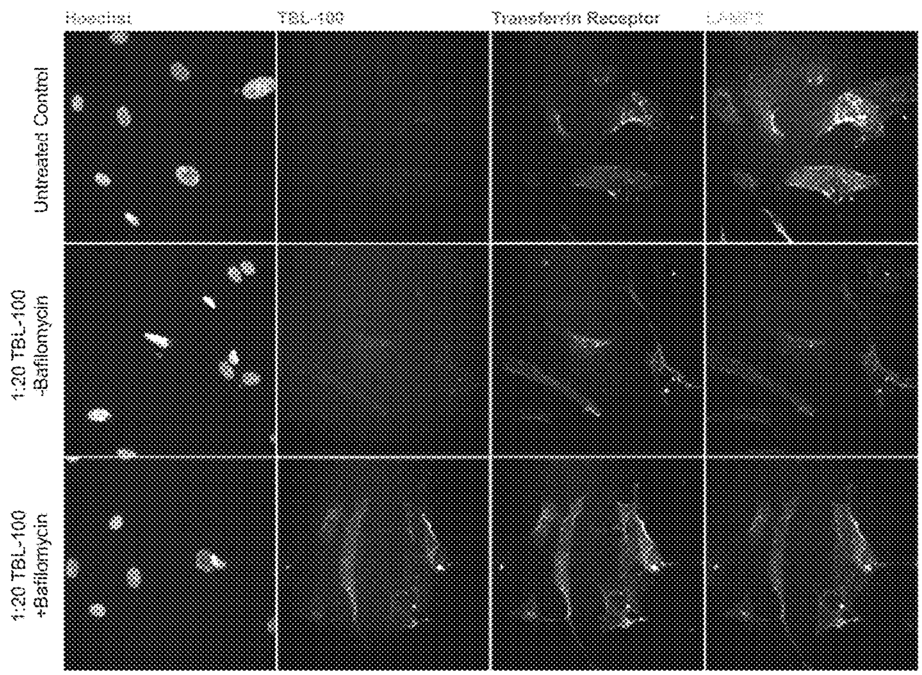
FIG. 2 contains images of TBL-100 at 24 hour of incubation.
Figure 3:
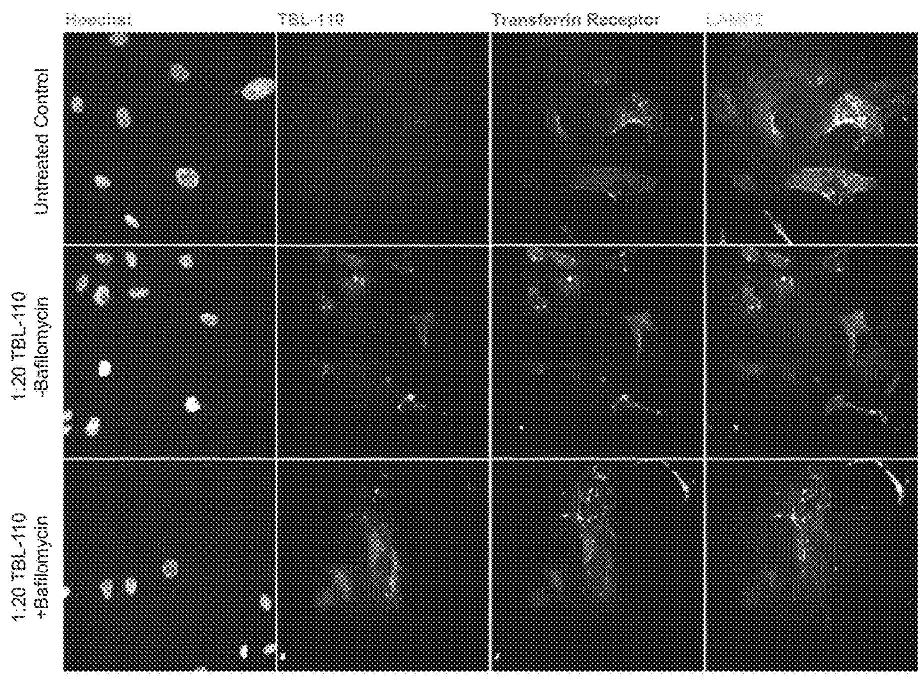
FIG. 3 contains images of TBL-110 at 24 hour of incubation.
Figure 4:
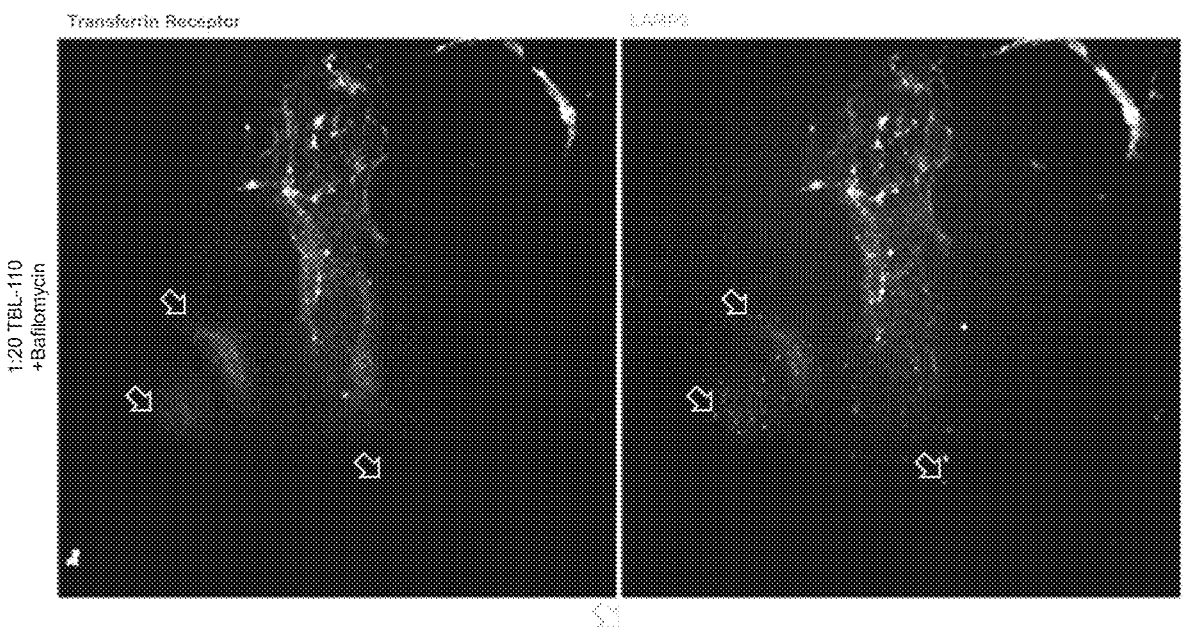
FIG. 4 contains images of TBL-100 at 24 hour of incubation. Despite similar staining patterns for Transferrin, Receptor and LAMP2, signal from each can be detected in unique locations. LAMP2 signal not colocalized with Transferrin Receptor.
Figure 5:
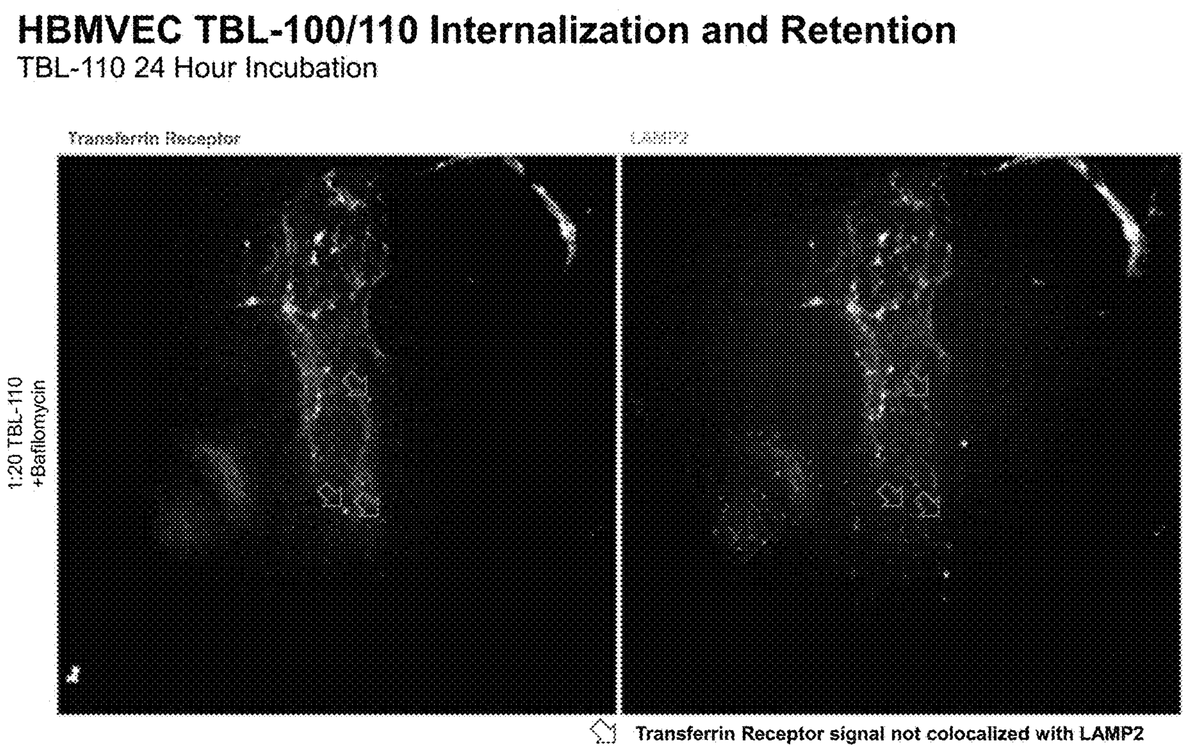
FIG. 5 contains images of TBL-110 at 24 hour of incubation. Despite similar staining patterns for Transferrin, Receptor and LAMP2, signal from each can be detected in unique locations. Transferrin Receptor signal not colocalized with LAMP2.
Figure 6:
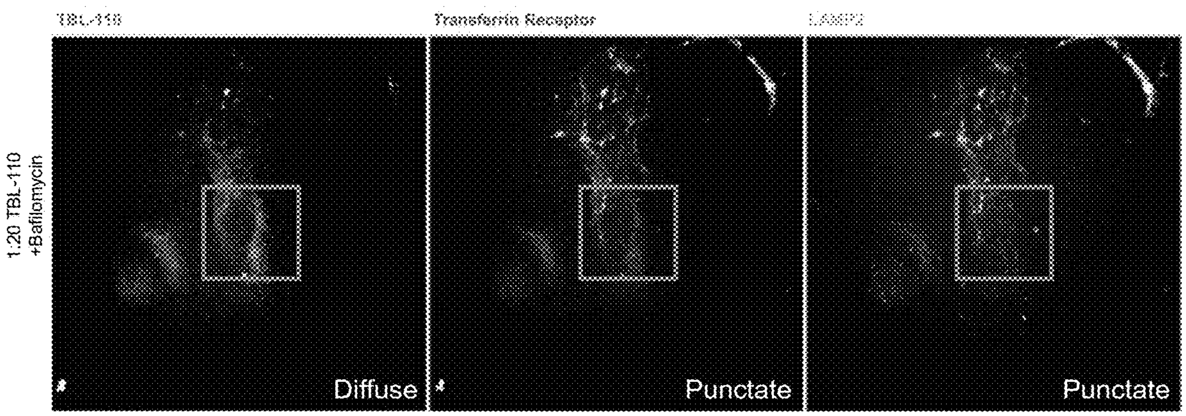
FIG. 6 contains images of TBL-110 at 24 hour of incubation. Pattern of TBL-110 signal appears to be more diffuse than the corresponding transferrin receptor and LAMP2 signal, which may suggest post-uptake release or internalization by an alternative mechanism.
Figure 7:
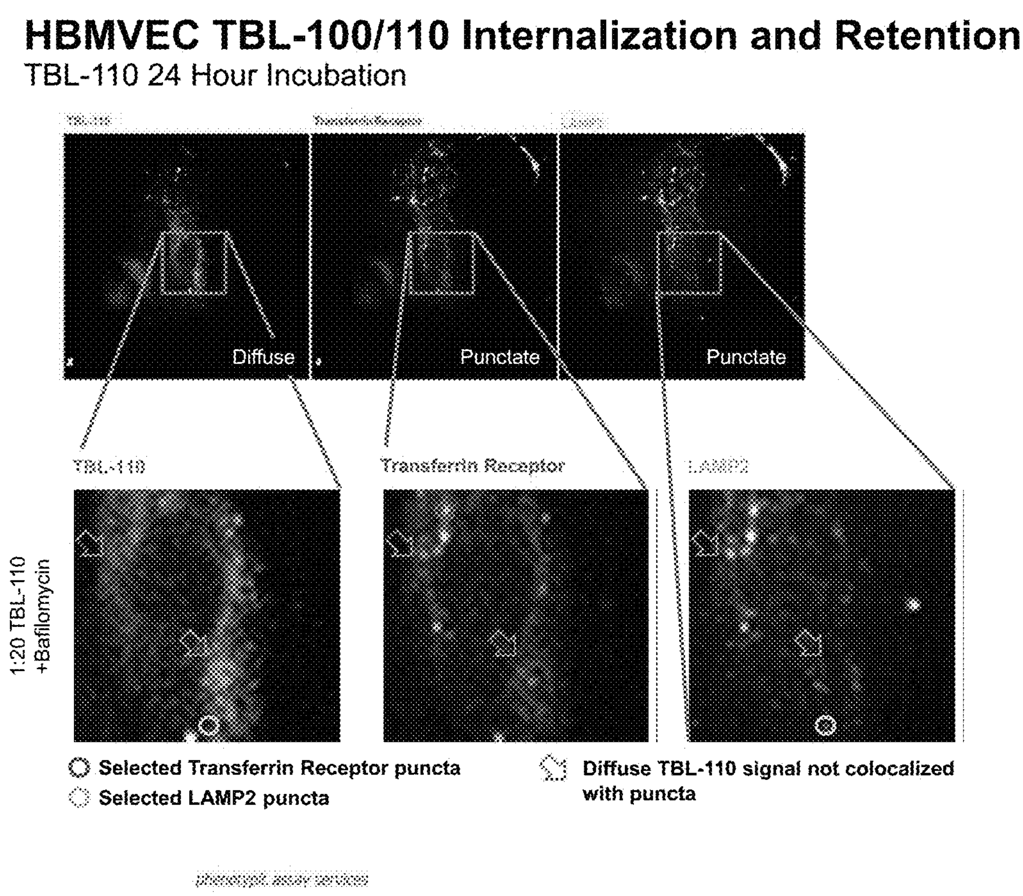
FIG. 7 contains images of TBL-110 at 24 hour of incubation. Pattern of TBL-110 signal appears to be more diffuse than the corresponding transferrin receptor and LAMP2 signal, which may suggest post-uptake release or internalization by an alternative mechanism i.e. outside of the endosomal-lysosomal system. Diffuse TBL-110 signal not colocalized with puncta.
Figure 8:
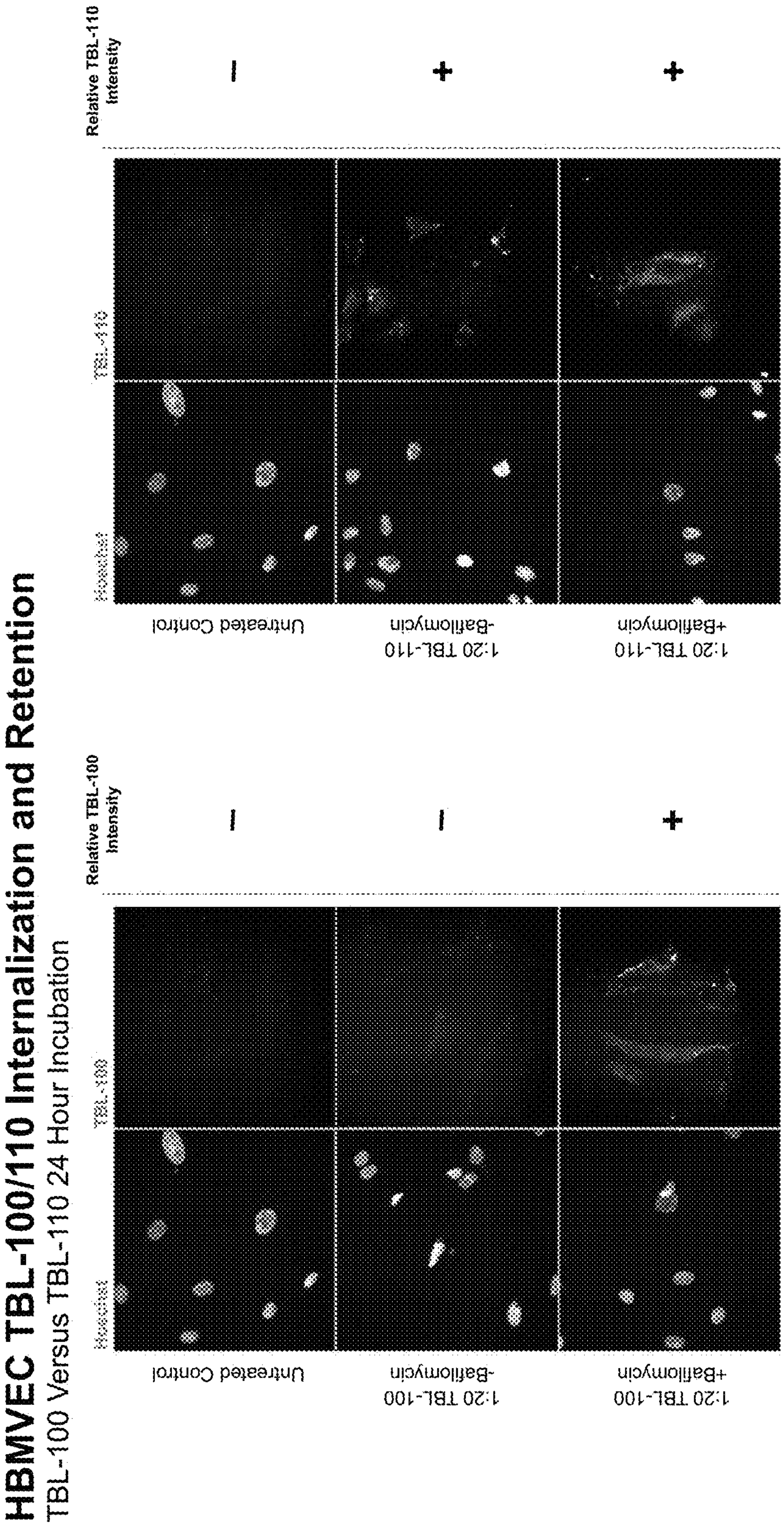
FIG. 8 contains images of TBL-100 Versus TBL-110 24 Hour Incubation.
Figure 9:
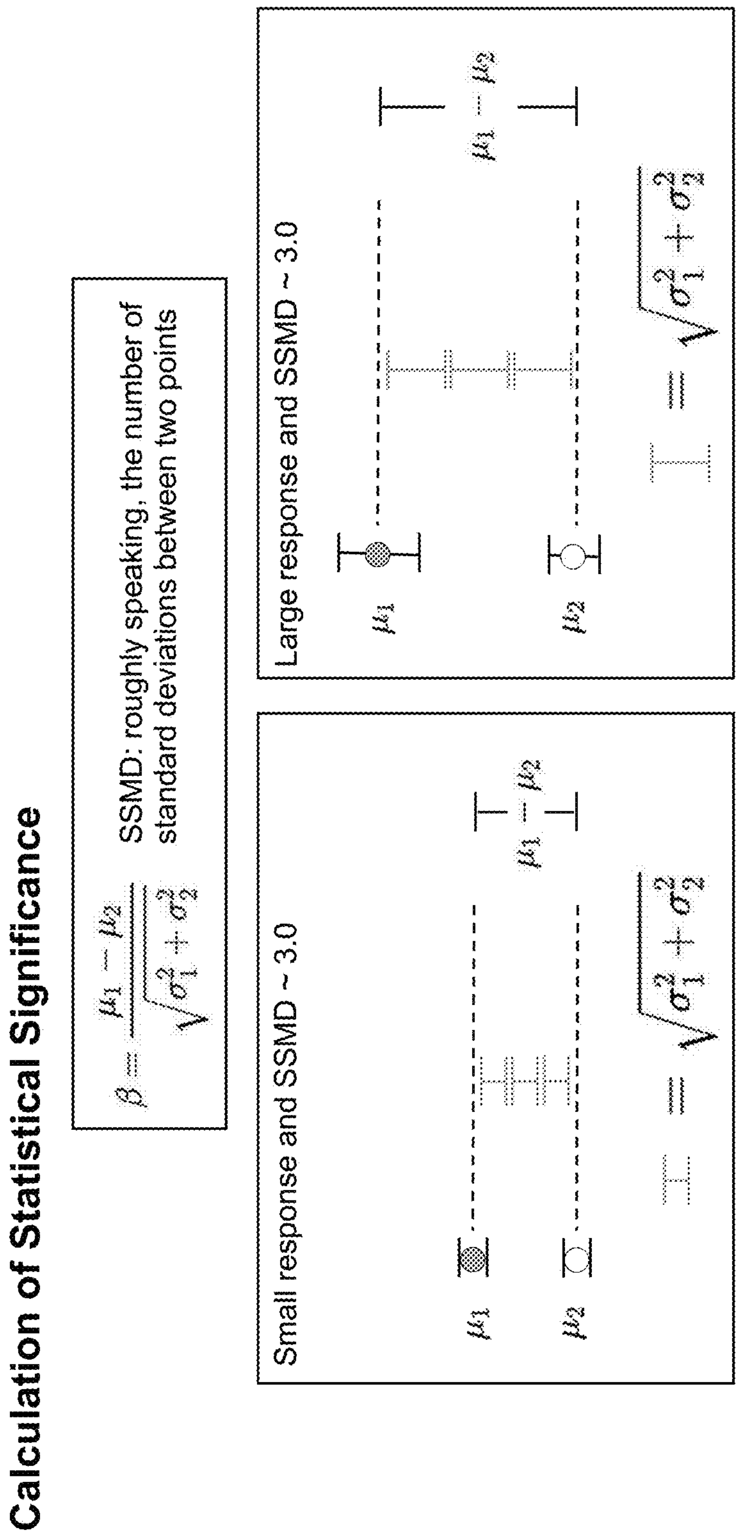
FIG. 9 shows calculation of statistical significance.
Figure 10:
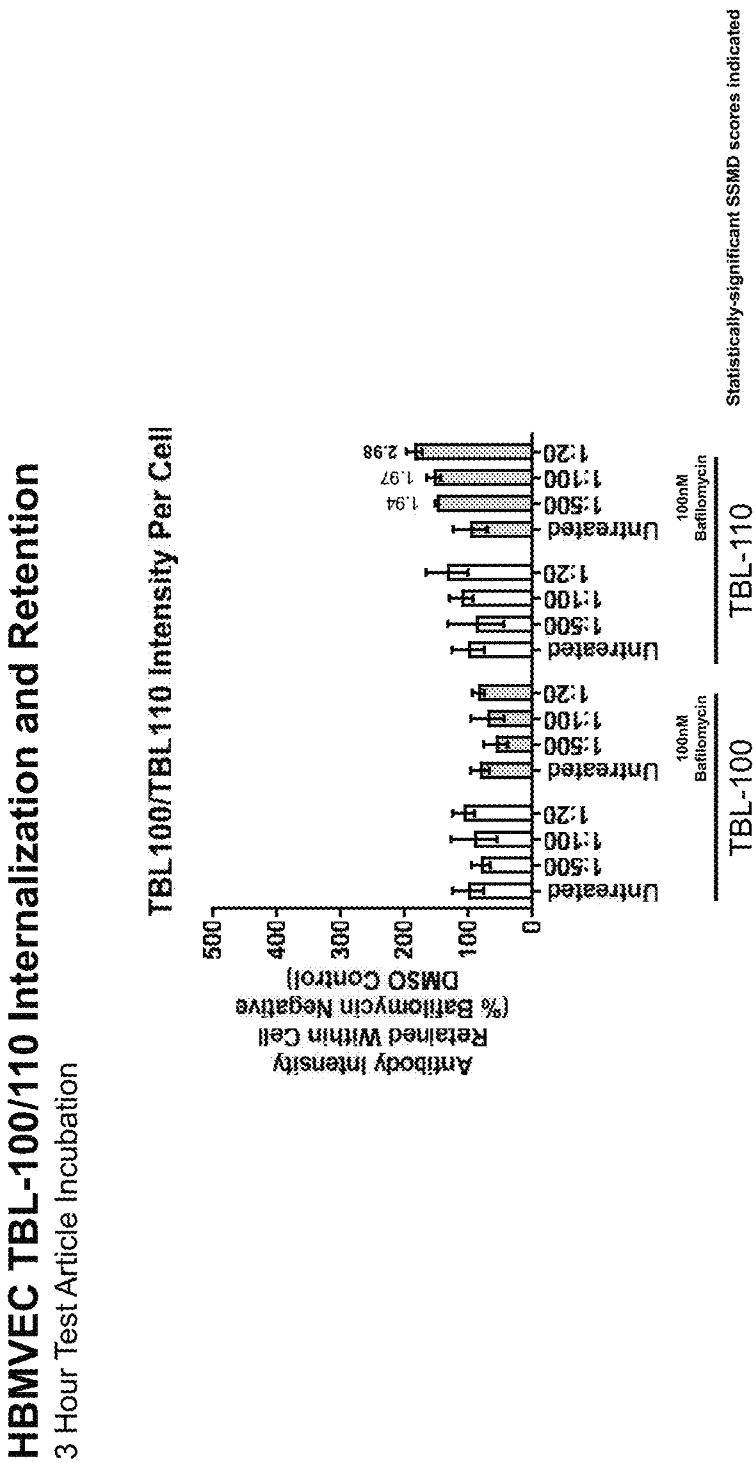
FIG. 10 shows antibody intensity retained within cell at 3 hour test article incubation.
Figure 11:
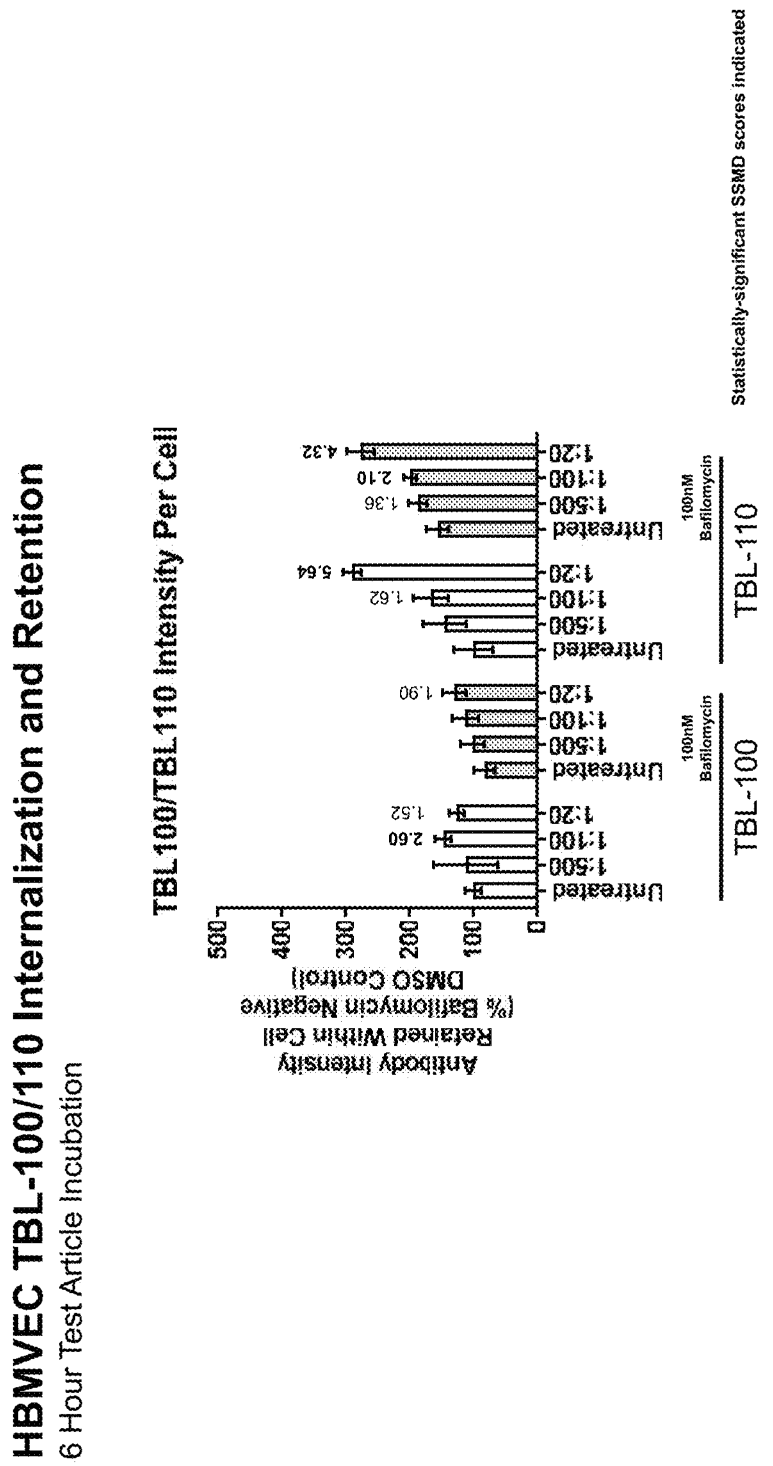
FIG. 11 shows antibody intensity retained within cell at 6 hour test article incubation.
Figure 12:
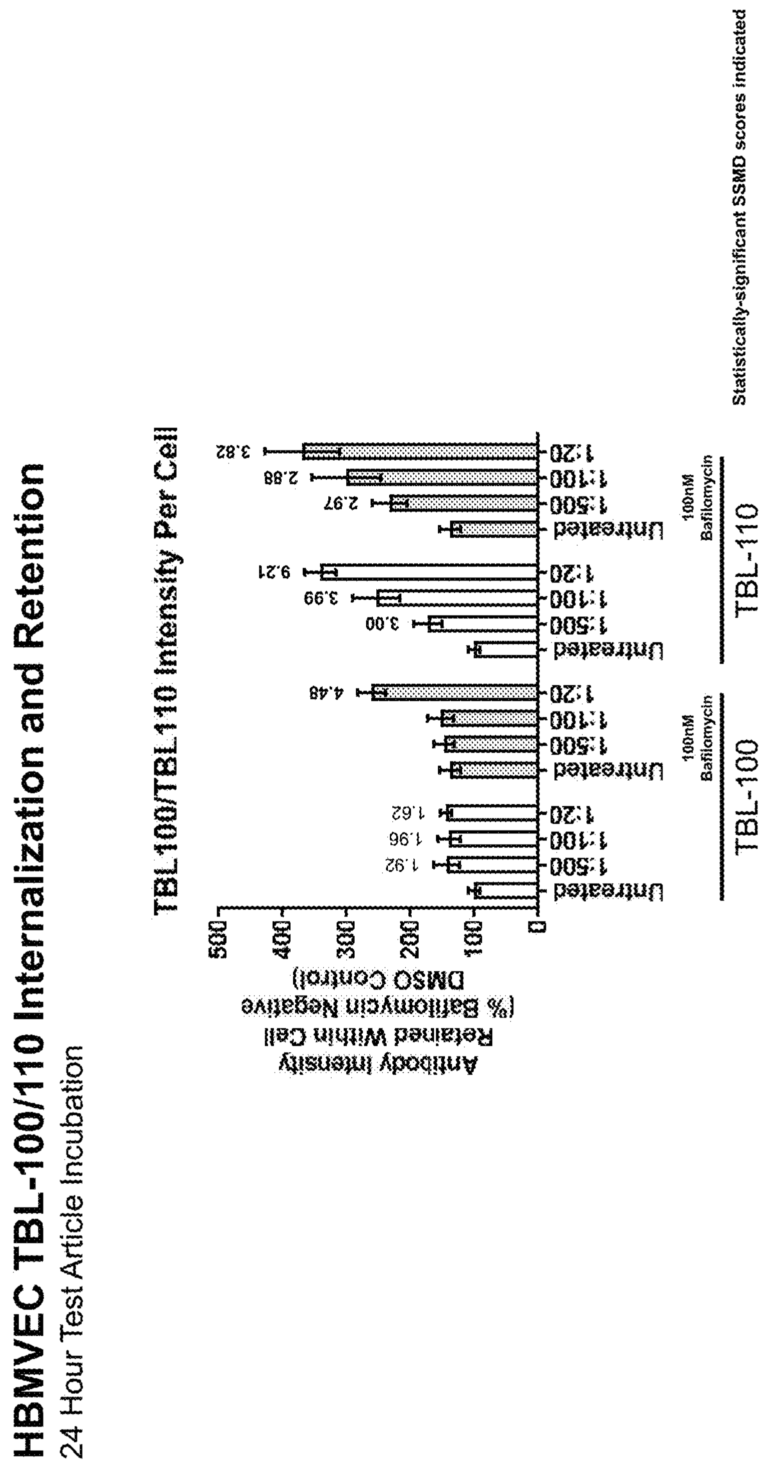
FIG. 12 shows antibody intensity retained within cell at 24 hour test article incubation.
Figure 13:
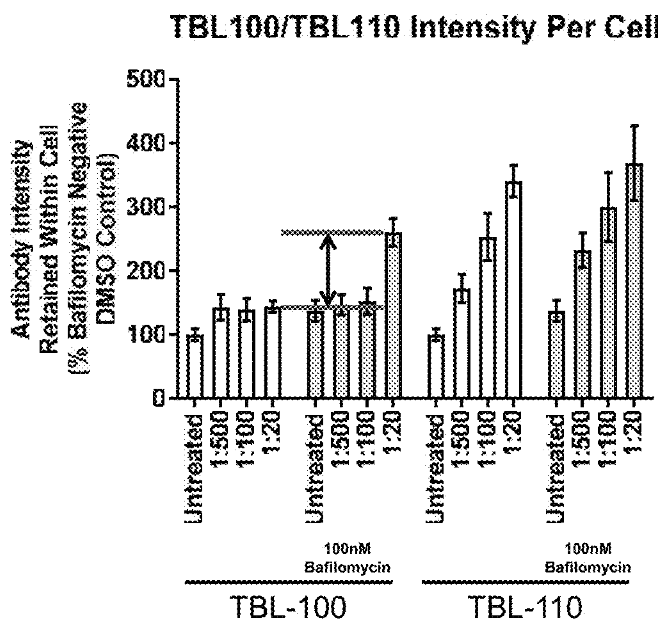
FIG. 13 shows antibody intensity retained within cell at 24 hour test article incubation. Increased retention of TBL-100 following Bafilomycin treatment (which disrupts lysosomal degradation) suggests that, when internalized, it enters and is cleared by the lysosome.
Figure 14:
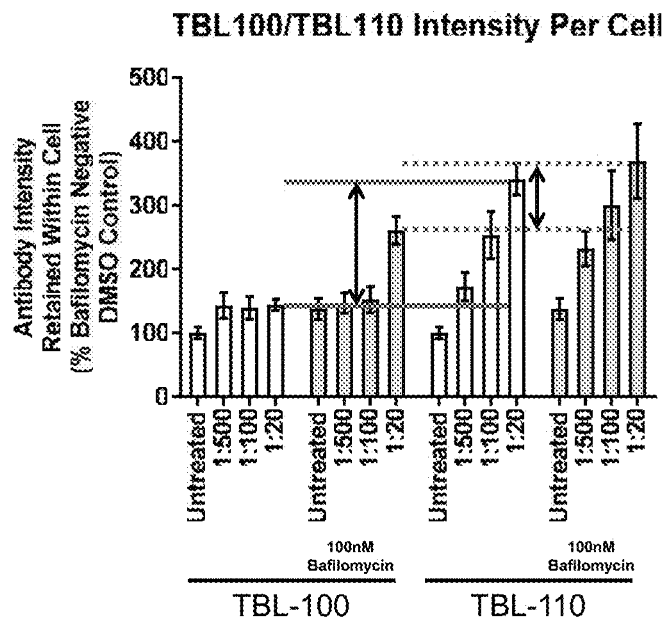
FIG. 14 shows antibody intensity retained within cell at 24 hour test article incubation. Higher levels of TBL-110 in both the presence ( . . . ) and absence ( ) of Bafilomycin treatment indicates that it is internalized and retained more readily than TBL-100.
Figure 15:
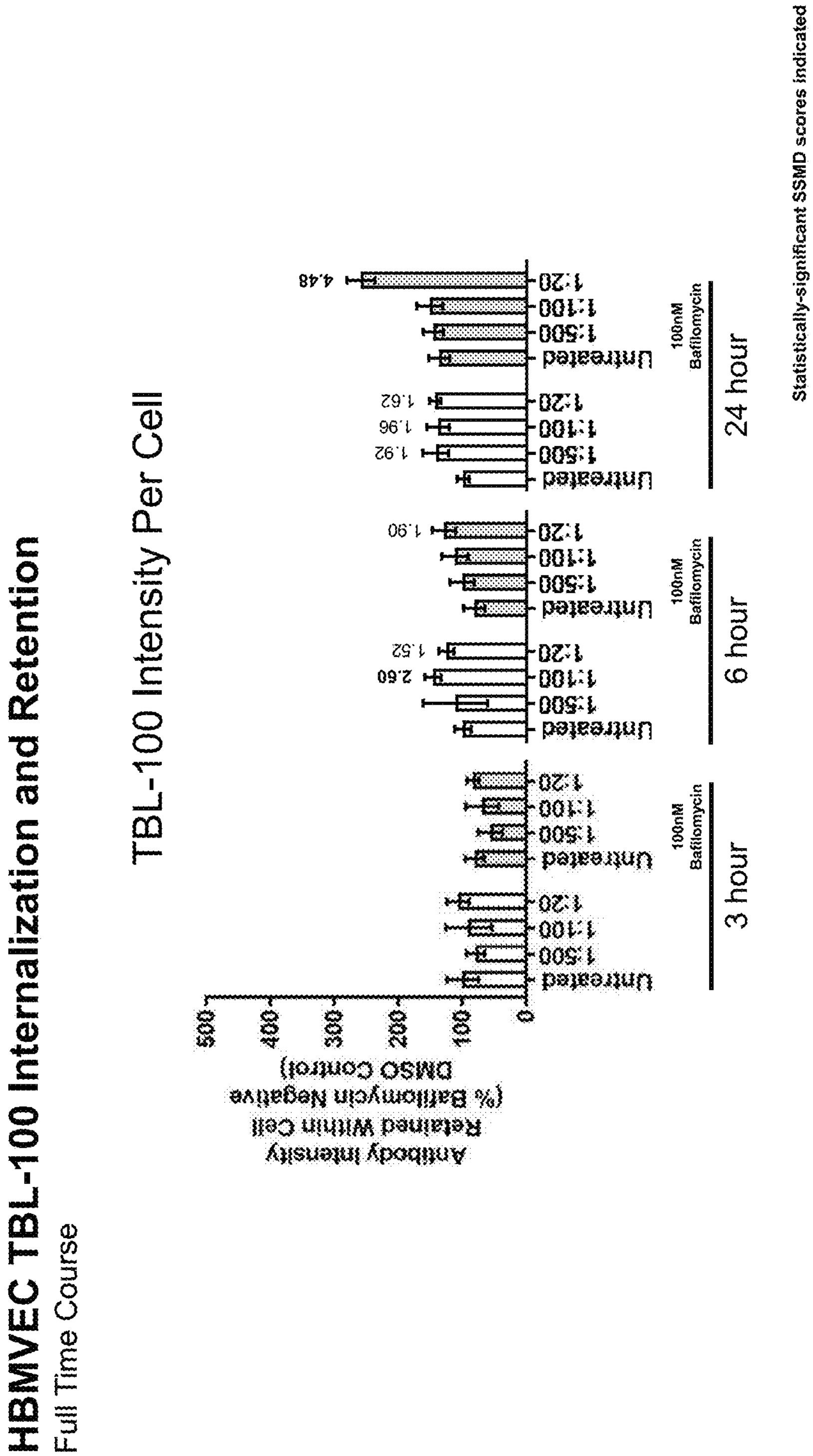
FIG. 15 shows TBL-100 intensity retained at 3 hour, 6 hour and 24 hour.
Figure 16:
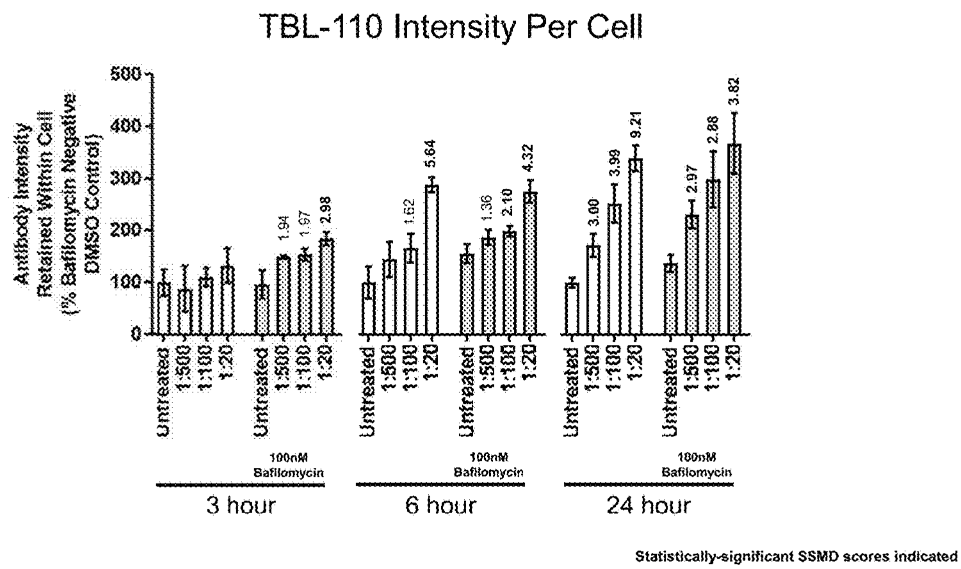
FIG. 16 shows TBL-110 intensity retained at 3 hour, 6 hour and 24 hour.
Figure 17:
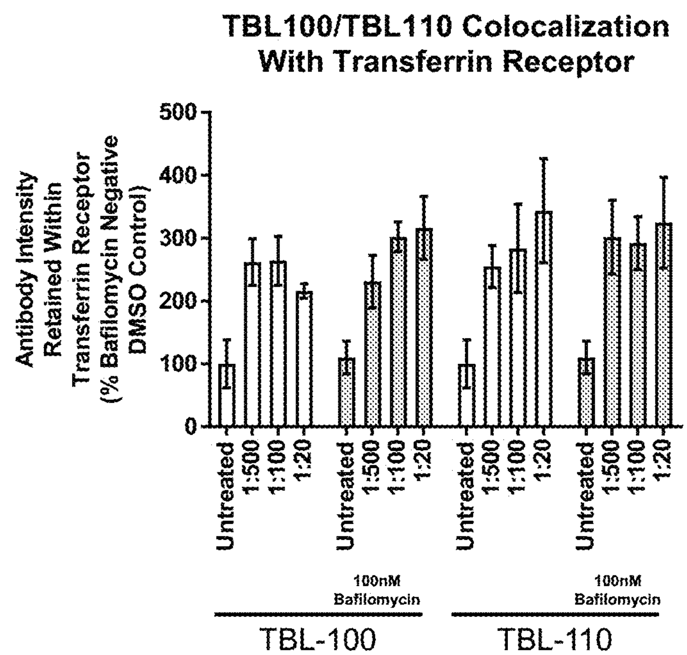
FIG. 17 shows TBL100/TBL110 colocalization with transferrin receptor at 24 hours. No significant differences in intensity of either TBL-100 or TBL-110 in masks drawn based on intensity of the transferrin receptor at 24 hours would suggest that neither test article preferentially colocalizes with the receptor.
Figure 18:
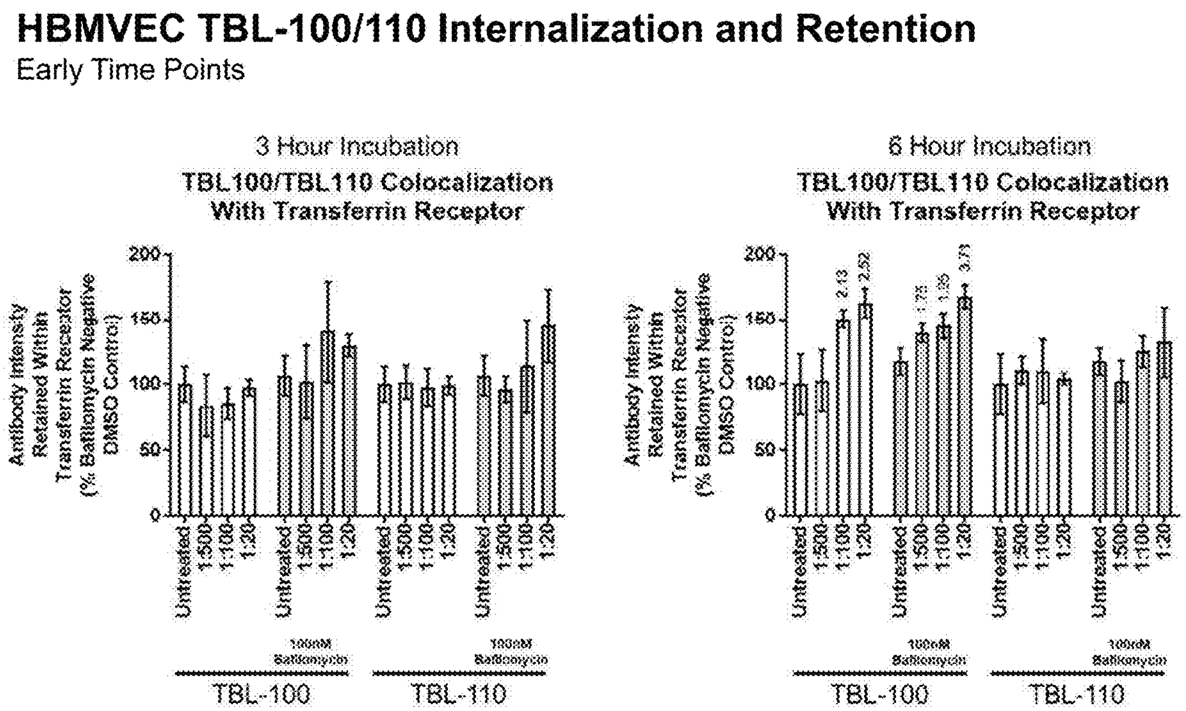
FIG. 18 shows TBL100/TBL110 colocalization with transferrin receptor at 3 hour incubation and 6 hour incubation. Pattern of significant increase in TBL-100 colocalization with the Transferrin Receptor at 6 hours suggests rapid transport into cell by this mechanism.
Figure 19:
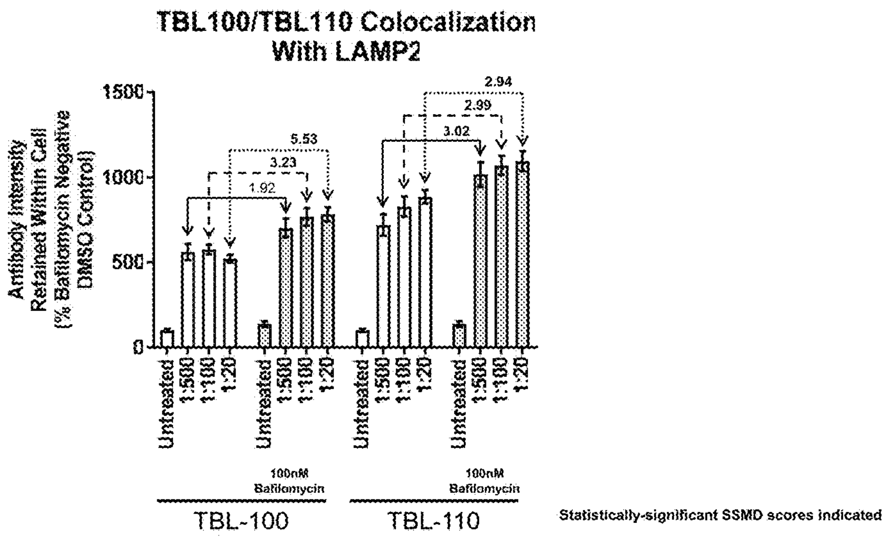
FIG. 19 shows TBL-100/TBL-110 colocoalization with LAMP2 at 24 hour test article incubation.
Figure 20:
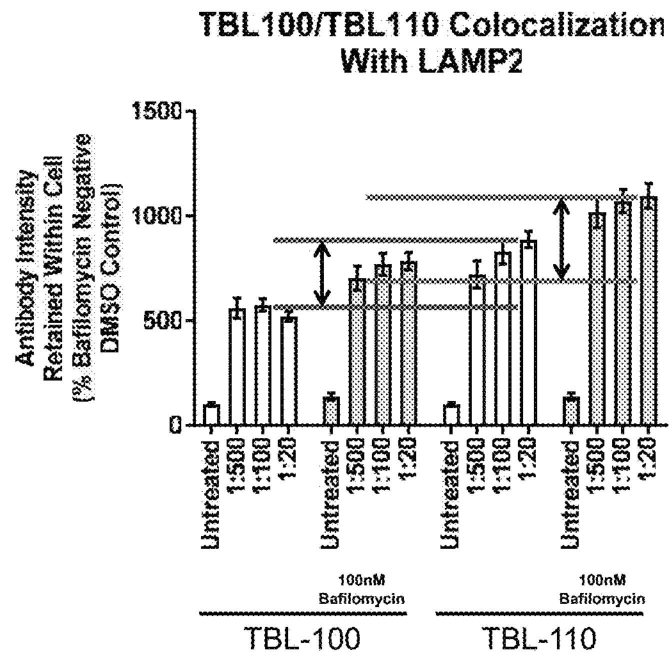
FIG. 20 shows TBL-100/TBL-110 colocoalization with LAMP2 at 24 hour test article incubation. Similar to the trends of TBL-100 and TBL-110 intensity quantified throughout the cell, higher levels of both test articles were colocalized with LAMP2 signal following Bafilomycin treatment. This indicates that when high levels of the test articles accumulate intracellularly, they are targeted to lysosomes.
Figure 21:
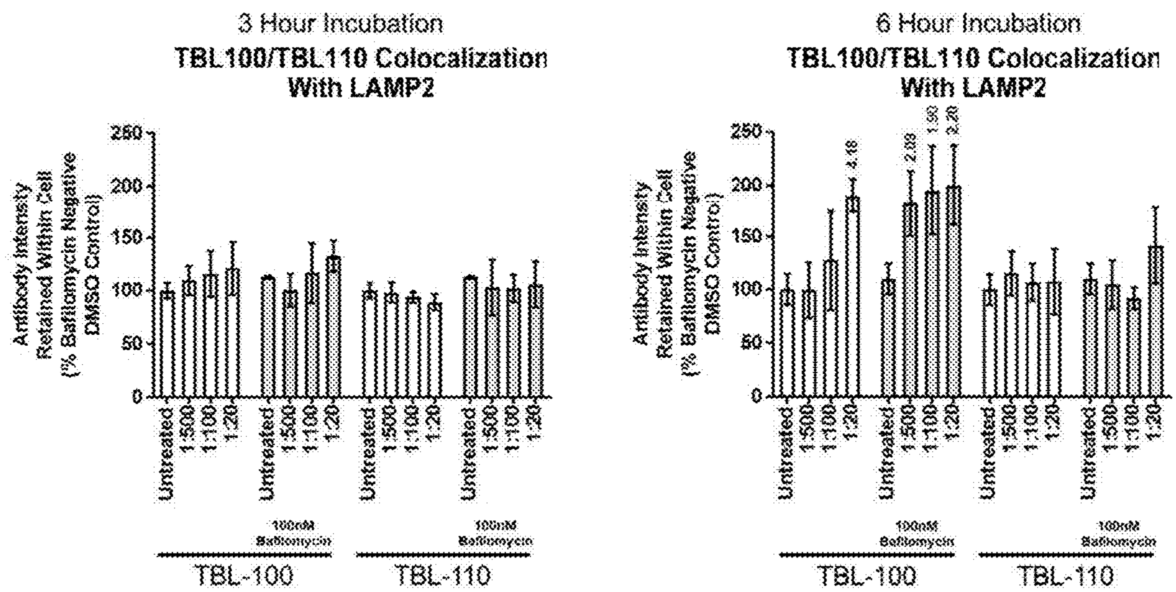
FIG. 21 shows TBL-100/TBL-110 colocoalization with LAMP2 at 3 and 6 hour test article incubation. Higher levels of colocalization of TBL-100 with LAMP2 at these early time points indicates rapid clearance of this test article once internalized. TBL-110 is not cleared by the lysosome as readily and therefore can accumulate.
Figure 22:
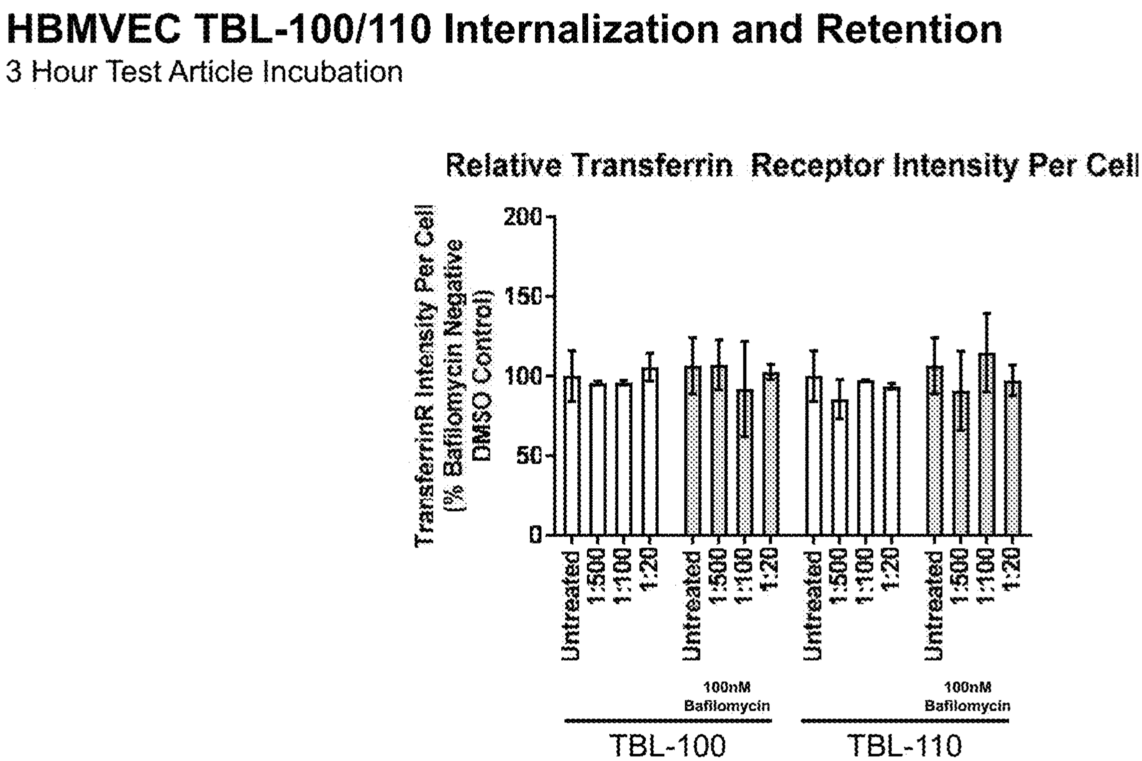
FIG. 22 shows relative transferrin receptor intensity per cell at 3 hour test incubation. No significant differences in transferrin receptor intensity per cell following any of the various combinations of test article and bafilomycin treatment.
Figure 23:
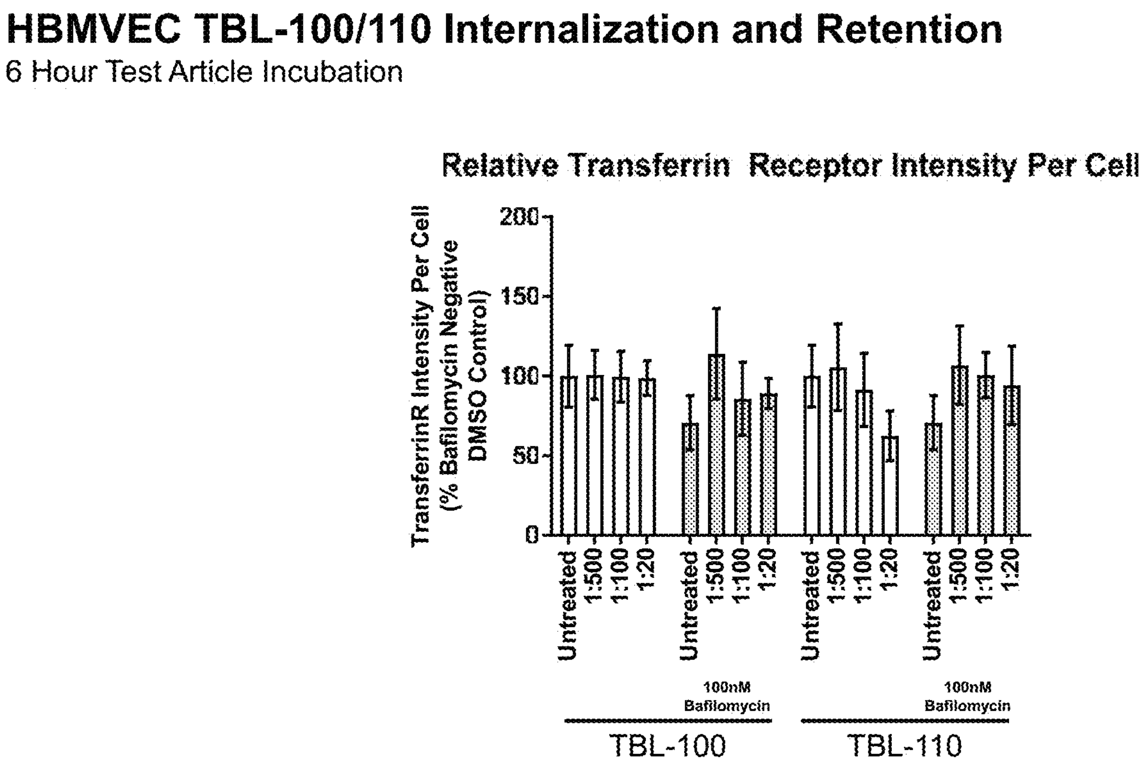
FIG. 23 shows relative transferrin receptor intensity per cell at 6 hour test incubation. No significant differences in transferrin receptor intensity per cell following any of the various combinations of test article and bafilomycin treatment.
Figure 24:
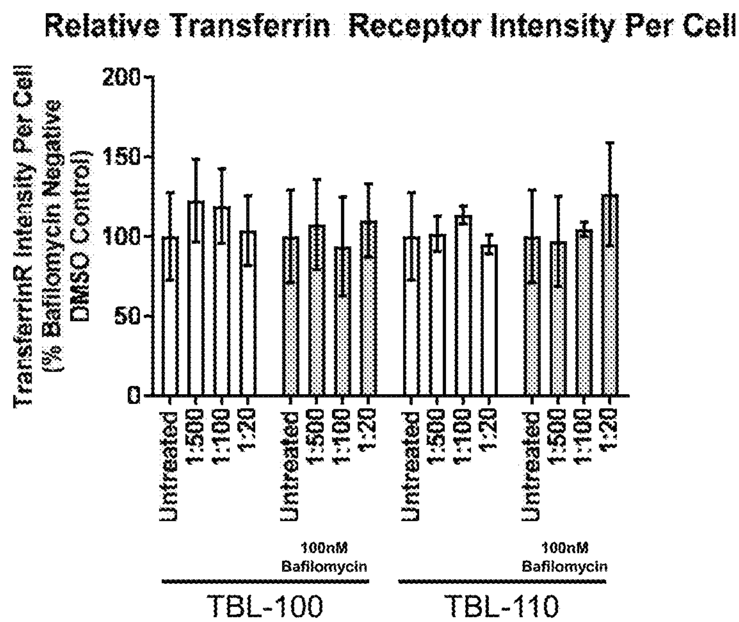
FIG. 24 shows relative transferrin receptor intensity per cell at 24 hour test incubation. No significant differences in transferrin receptor intensity per cell following any of the various combinations of test article and bafilomycin treatment.
Figure 25:
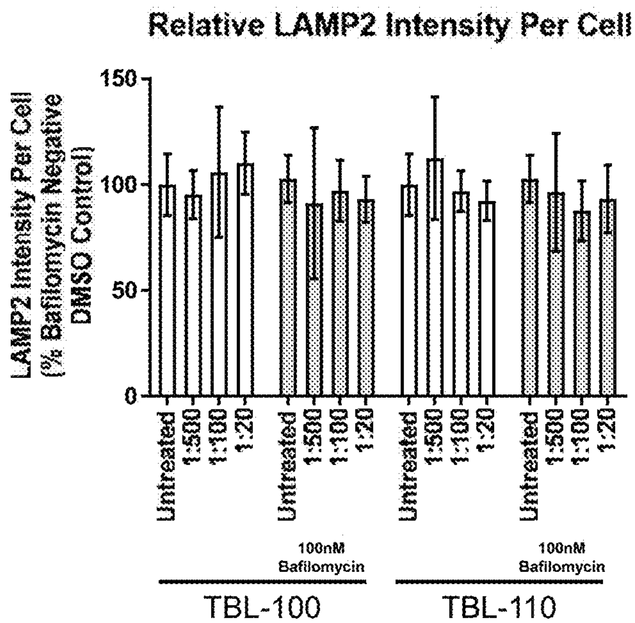
FIG. 25 shows relative LAMP2 intensity per cell at 3 hour test article incubation. No significant differences in LAMP2 intensity per cell following any of the various combinations of test article and bafilomycin treatment.
Figure 26:
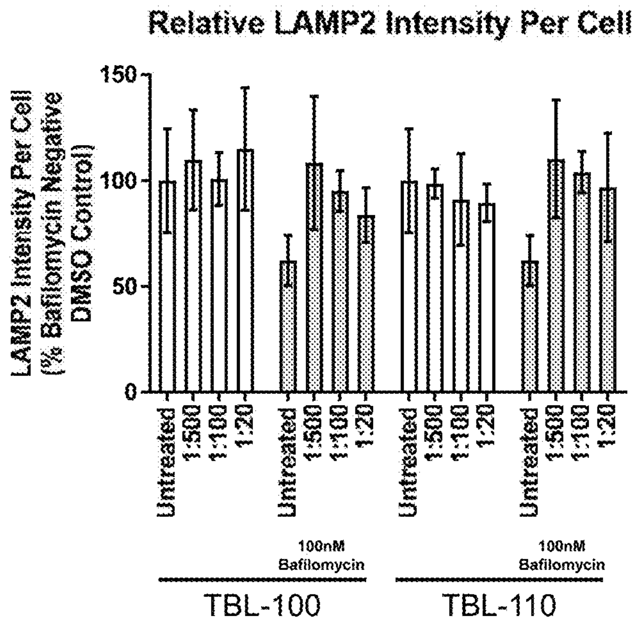
FIG. 26 shows relative LAMP2 intensity per cell at 6 hour test article incubation. No significant differences in LAMP2 intensity per cell following any of the various combinations of test article and bafilomycin treatment.
Figure 27:
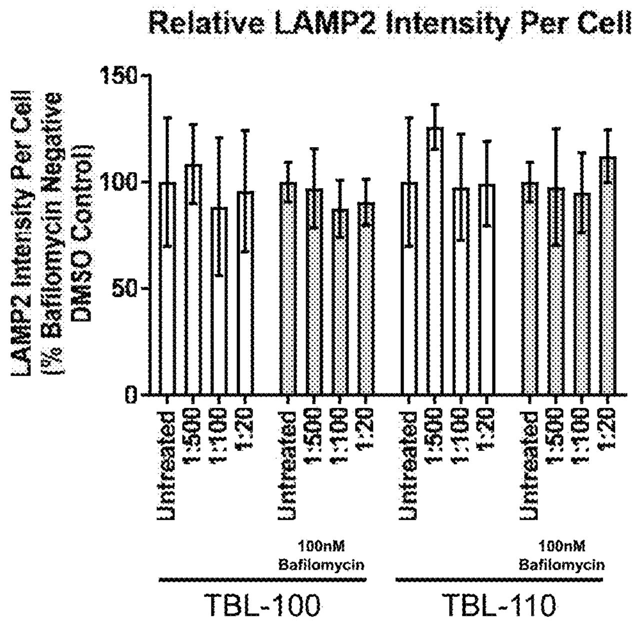
FIG. 27 shows relative LAMP2 intensity per cell at 24 hour test article incubation. No significant differences in LAMP2 intensity per cell following any of the various combinations of test article and bafilomycin treatment.
Figure 28:
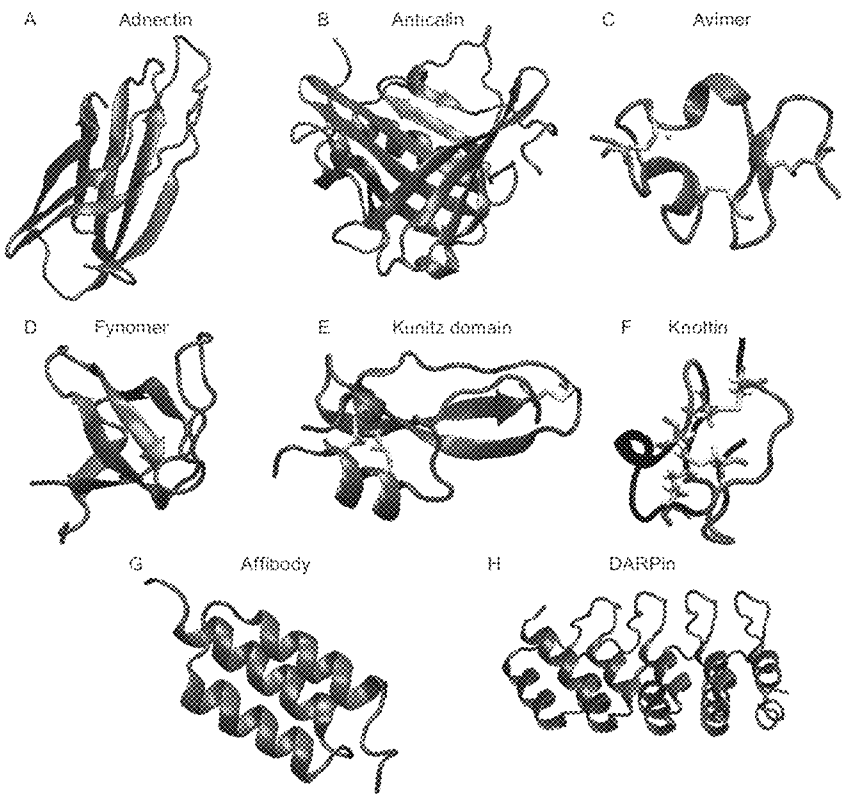
FIG. 28 depicts cartoon-structures of protein scaffolds, and was adopted from Simeone et al., Protein Cell 2018. 9(1):3-14.
Figure 29A:
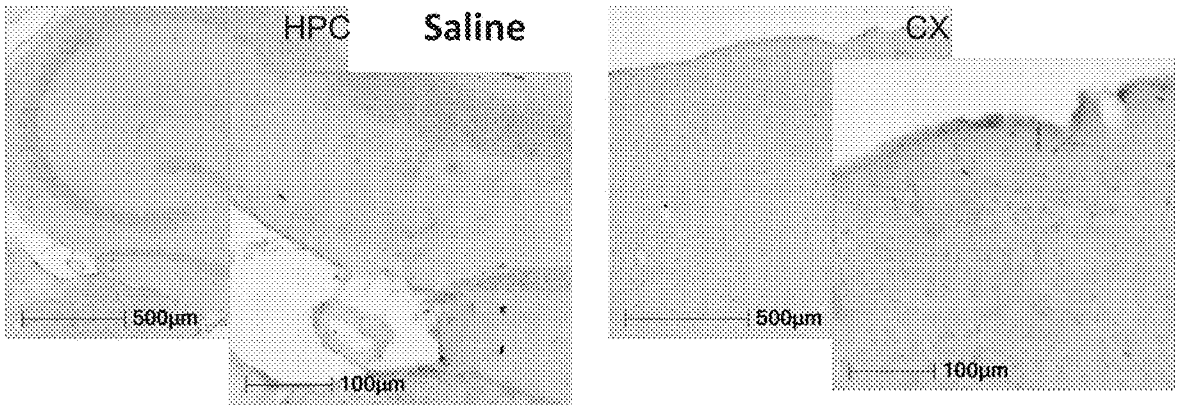
FIGS. 29A-29E depict immunohistochemical images made in Example 4.
Figure 29B:
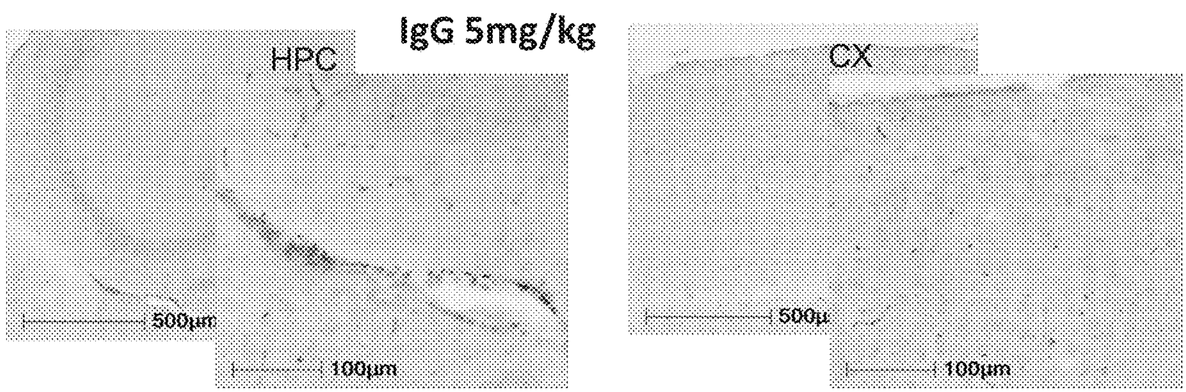
Figure 29C:
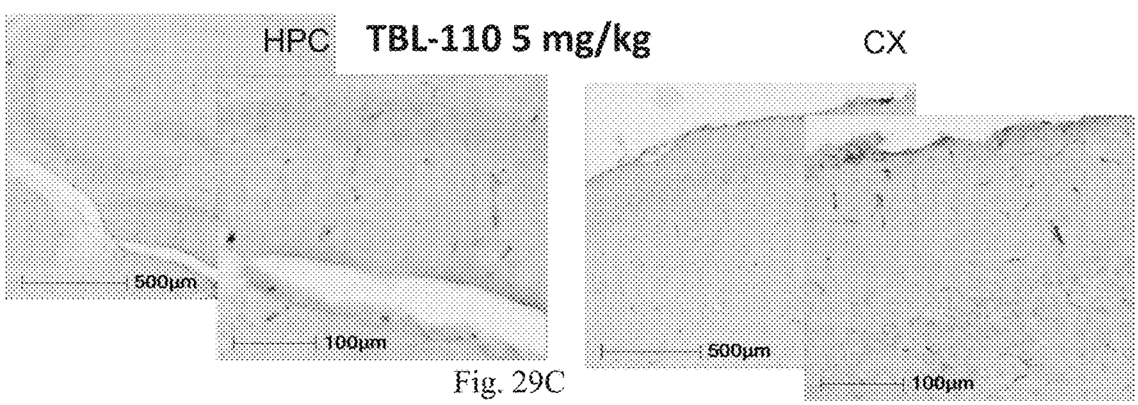
Figure 29D:
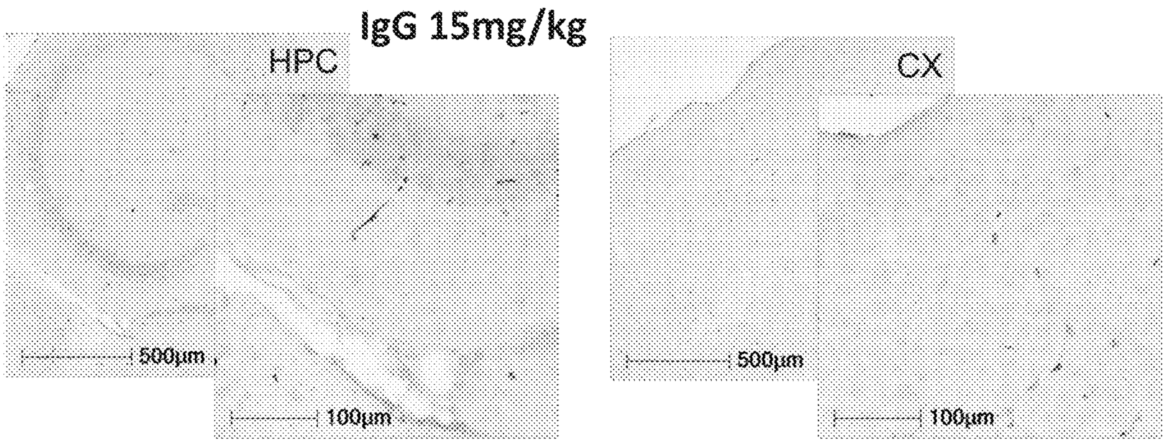
Figure 29E:
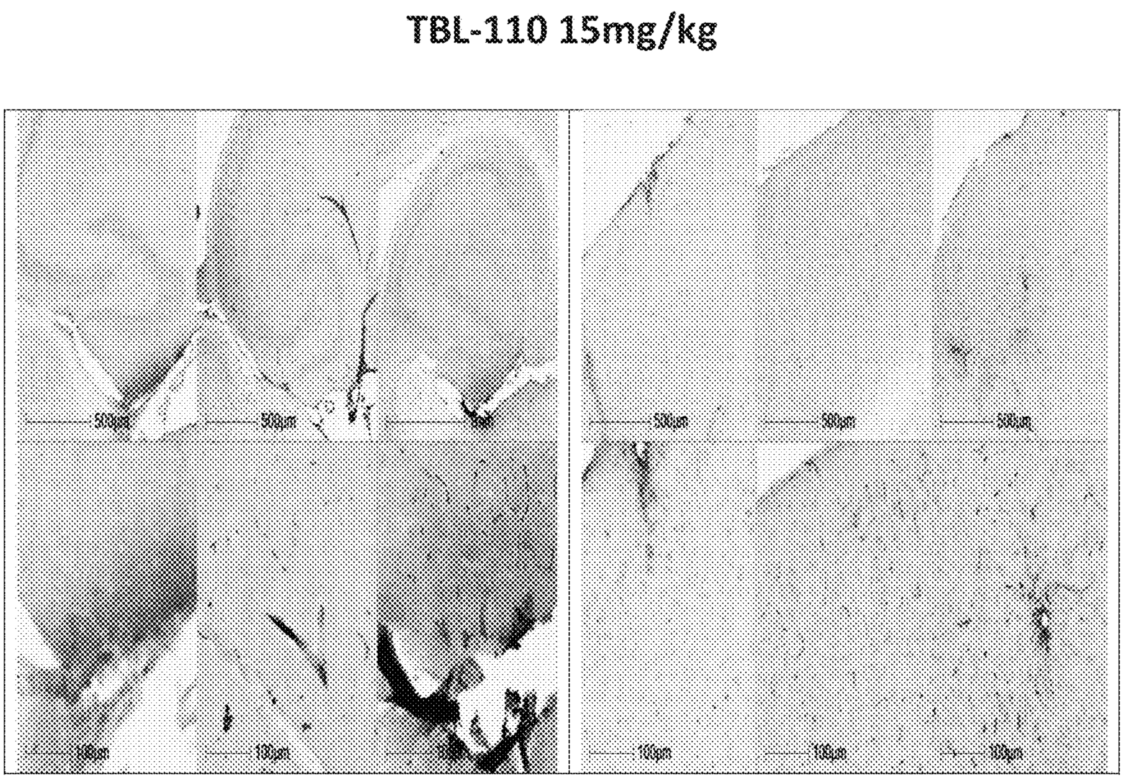
Figure 29D:
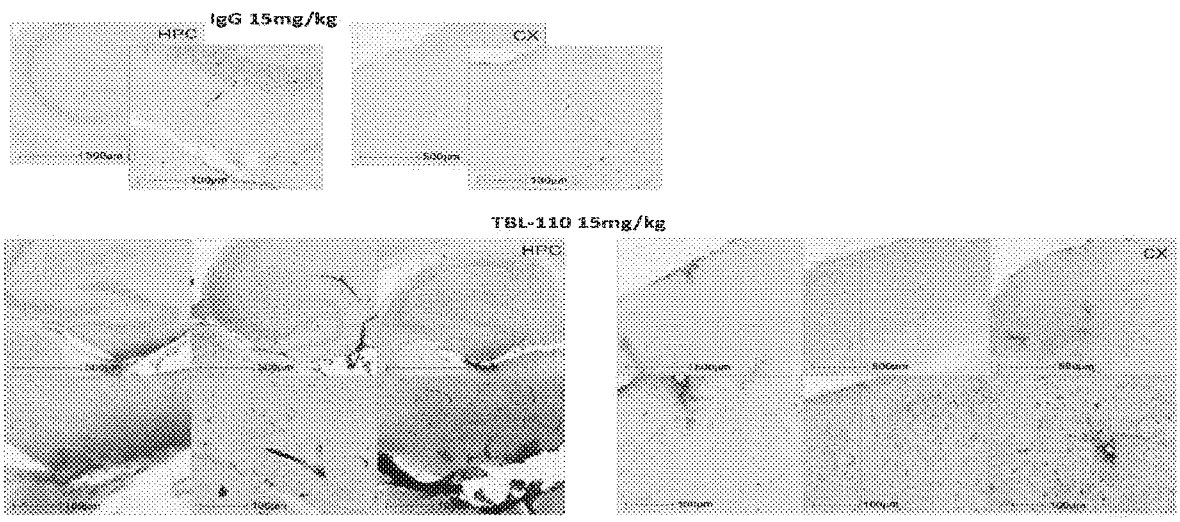

SDS-Page and Western blot analysis of the resulting construct in presented in FIGS. 1A and 1B, respectively. Lane M1: Protein Marker, TaKaRa, Cat. No. 3452. Lane $M_2$: Protein Marker, GenScript, Cat. No. M00521. Lane 1: Reducing condition. Lane 2: Non-reducing condition.

The following general procedures were used:

Plasmid Preparation:

1) Target DNA sequence was designed, optimized and synthesized;

2) The complete sequence was sub-cloned into pcDNA3.4vector;

3) Transfection grade plasmid was maxi-prepared for Expi293F cell expression.

Cell Culture and Transient Transfection:

1) Expi293FTMcells were grown in serum-free Expi293TMExpression Medium (Thermo Fisher Scientific).

2) The cells were maintained in Erlenmeyer Flasks (Corning Inc.) at 37° C. with 8% CO2 on an orbital shaker (VWR Scientific).

3) One day before transfection, the cells were seeded at an appropriate density in Corning Erlenmeyer Flasks.

4) On the day of transfection, DNA and ExpiFectamine™293 Reagent were mixed at an optimal ratio and then added into the flask with cells ready for transfection.

5) The recombinant plasmids encoding target antibody were transiently co-transfected into suspensionExpi293Fcell cultures. Approximately 16-18 hours post-transfection, ExpiFectamine™ 293 Transfection Enhancer 1 and ExpiFectamine™ 293 Transfection Enhancer 2 were added to each flask. The cell culture supernatants collected and ay 6 were used for purification.

Purification and Analysis:

1) Cell culture broth was centrifuged and followed by filtration.
2) Filtered cell culture supernatant was loaded onto an affinity purification column at an appropriate flowrate.
3) After washing and elution with appropriate buffers, the eluted fractions were pooled and buffer exchanged to the final formulation buffer.
4) The purified protein was analyzed by SDS-PAGE, Western blotanalysis to determine the molecular weight and purity.
5) The concentration was determined by A280 method.

Anti-tauC3 antibody's ability to prevent tauC3-induced changes in mitochondrial morphology as an index of neurotoxicity is tested using cultured neurons transfected with tauC3 plasmid or by exposing the cells to apoptotic insults to induce caspase 3 cleavage of FLT (SEQ ID NO:1).

Immunohistochemistry is used to identify antitauC3 antibody-tauC3 complexes and explore their subcellular localization in cultured neurons and brain slices by high resolution fluorescence microscopy.

Example 2

Internalization and retention of murine antiTauC3 antibody ("TBL-100") and fusion construct of Example 1 were compared.

Rate of internalization and retention of the fusion construct of Example 1 appeared to be greater than of the murine antiTauC3 antibody.

Co-localization of the fusion construct with lysosomal markers as well as increased retention of the test article following treatment with bafilomycin suggests that internalized murine anti-TauC3 antibody may be more efficiently cleared via lysosomal activity than the fusion construct of Example 1.

Project Methodology Summary

Cells

Human Brain Microvascular Endothelial Cells (HBMVEC) (iXCells) are plated at 1500 cells per well of a 384 well plate and cultured for 24 hours prior to treatment with each of murine antiTauC3 antibody and fusion construct of Example 1 ("test articles") in both the presence and absence of Bafilomycin.

Treatment

Murine Anti-TauC3 antibody and fusion construct test antibodies are tested in 3-point dose-response—1:500, 1:100, 1:20—for 3, 6 and 24 hour treatment exposures. Parallel wells on the same plate are also treated with either 0.1% DMSO or 100 nM Bafilomycin to measure effects of lysosomal activity following test article internalization. Following the appropriate time-course for each of the three time points, cells are fixed and permeabilized in a PFA solution and blocked overnight in goat block buffer.

Analysis

Automated quantitative analysis of neurite outgrowth as well as standard metrics associated with neuronal health using the Thermo CX7 HCS. Instrumentation and analysis suite. A minimum of 4 replicate wells per condition with 9 fields acquired per well using a 20× objective.

Project Methodology Detail.

1. Dissociate HBMVEC cells (IXCells) and count using Countess II cell counter.
2. Prepare mixture of 14 ml complete media and 1.05×106 cells.
3. Enough for 700 wells of low volume 384 well plate (20 ul/1500 cells per well).
4. Array cells into each of three plates (3, 6, 24 hour test article treatment).
5. Return plated cells to 37 degree incubator for 24 hours.
6. Following 24 hour pre-culture, prepare dilutions of TBL-100 and TBL-110 (1:500, 1:100, 1:20) in 8 ml of complete media.
   Excess volume enables liquid handling instrumentation to perform complete media change.
6. Divide each dilution into two equal volumes.
7. To one, add Bafilomycin stock to yield a final concentration of 100 nM.
8. Use Apricot liquid handling platform to carry out complete media change.
9. Return plates to incubator for 3, 6 and 24 hours.
10. At the conclusion of each time point incubation, fix for 20 minutes using 4% PFA solution in PBS, wash with PBS, and permeabilize cells.
11. Block overnight in goat block buffer.
12. To each well of all three plates, add the following mixture of primary antibodies is added:
    Transferrin Receptor antibody (1:400 rabbit primary) [Cell Signaling Technology—13208S]
    LAMP2 antibody (1:200 rat primary) [Abcam—ab13524]
13. Return plates to 4 degree fridge overnight
14. Wash plates 4× each with PBS using Apricot before adding the following mixture of secondary antibodies and labels for 1 hour at room temperature:
    Hoechst (1:1000 occupying 386 channel for detection of nuclei)
    Goat anti-mouse (1:1000 occupying 488 channel for detection of TBL100/110)
    Goat anti-rabbit (1:1000 occupying 560 channel for detection of Transferrin R)
    Goat anti-rat (1:1000 occupying 650 channel for detection of LAMP2)
15. Remove secondary antibody mixture using Apricot and fill wells with PBS containing antibiotic/antimycotic and sodium-azide
16. Seal plates and image using Thermo Scientific CellInsight CX7 instrument and a 20× objective Increased retention of TBL-100 (murine antiTauC3 antibody) following Bafilomycin treatment suggests that in untreated cells it is readily cleared by the lysosome.

Both test articles show higher levels of colocalization with the lysosomal marker LAMP2 than with Transferrin Receptor (TR) at later time points but TBL-100 (murine antiTauC3 antibody) more readily colocalizes with both at early time points suggesting rapid uptake by TR and subsequent clearance by the lysosome.

High levels of intracellular TBL-110 (fusion construct of Example 1), which is not colocalized with either LAMP2 or TR, suggests that this test article is released upon internalization or is taken up by an alternative mechanism.

Example 3

The findings of Example 2 were confirmed in Human, Monkey and Brain Microvascular Cells (HBMVEC).

Project Methodology Summary

Cells

Human, Monkey or Mouse Brain Microvascular Endothelial Cells (BMVEC) from Creative Bioarray were plated at 1500 cells per well of a 384 well plate and cultured for 24 hours prior to treatment with each of murine antiTauC3 antibody and fusion construct of Example 1 in both the presence and absence of 100 nM Bafilomycin.

Treatment

Murine antiTauC3 antibody (TBL-100) and fusion construct of Example 1 (TBL-110) (collectively "test articles") were tested in. 3-point dose-response—1:500, 1:100, 1:20—for 24 hour treatment exposures. Parallel wells on the same plate were also treated with either 0.1% DMSO or 100 nM Bafilomycin to measure effects of lysosomal activity following test article internalization. Following the appropriate time-course for each of the three time points, cells were fixed and permeabilized in a PFA solution and blocked in goat block buffer.

Analysis

Automated quantitative analysis of standard metrics was performed using the Thermo CX7 HCS instrumentation and analysis suite. A minimum of 8 replicate wells per condition with 16 fields acquired per well using a 40× objective.

Project Methodology Detail

1. Dissociate BMVEC cells and count using Countess II cell counter.
2. Array cells into plates for 24 hour test article treatment.
3. Return plated wells to 37 degree incubator for 24 hours.
4. Following 24 hour pre-culture, prepare dilutions of Murine antiTauC3 antibody and fusion construct of Example 1 (1:500, 1:100, 1:20) in 8 ml of complete media.
   Excess volume enables liquid handling instrumentation to perform complete media change
5. Divide each dilution into two equal volumes.
6. To one, add Bafflomycin stock to yield a final concentration of 100 nM.
7. Use Apricot liquid handling platform to carry out complete media change.
8. Return plates to incubator for 24 hours.
9. At the conclusion of each time point incubation, fix for 20 minutes using 4% PFA solution in PBS, wash with PBS, and permeabilize cells.
10. Block 1 hour at room temperature in goat block buffer.
11. To each well of all three plates, add the following mixture of primary antibodies is added:
    Transferrin Receptor antibody (1:200 rabbit primary) [Cell Signaling Technology—13208S]
    LAMP2 antibody (1:200 rat primary) [Abcam—ab13524]
12. Return plates to 4 degree fridge overnight.
13. Wash plates 5× each with PBS using Apricot before adding the following mixture of secondary antibodies and labels for 1 hour at room temperature:
    Hoechst (1:1000 occupying 386 channel for detection of nuclei)
    Goat anti-mouse (1:1000 occupying 488 channel for detection of Murine antiTauC3 antibody/fusion construct of Example 1)
    Goat anti-rabbit (1:1000 occupying 560 channel for detection of Transferrin R)
    Goat anti-rat (1:1000 occupying 650 channel for detection of LAMP2)
14. Remove secondary antibody mixture using Apricot and fill wells with PBS containing antibiotic/antimycotic and sodium-azide.
15. Seal plates and image using Thermo Scientific CellInsight CX7 instrument and a 40× objective.

Results Summary

1. Rate of internalization and retention of fusion construct of Example 1 (TBL-110) appears to be greater than of the murine antiTauC3 antibody (TBL-100) in Human, Monkey and Mouse BMVEC lines.
2. Increased retention of fusion construct of Example 1 compared to the murine antiTauC3 antibody was greatest in the absence of Bafilomycin (i.e. in the presence of Bafilomycin, and at the highest test concentrations, both the murine antiTauC3 antibody and fusion construct of Example 1 had similar high levels of retention).
3. The addition of Bafilomycin preferentially increased retention of the murine antiTauC3 antibody rather than fusion construct of Example 1 for Human and Monkey BMVEC, cell lines.
4. Transferrin-R and LAMP2 expression levels were not significantly affected by increasing doses of either test article.
5. Both murine antiTauC3 antibody and fusion construct of Example 1 showed partial colocalization with Transferrin Receptor as well as LAMP2.

Thus, the construct of Example 1 (TBL-110) shows cross species reactivity and works in human, monkey and mouse cell lines. This findings allow for, e.g., for preclinical pharmacokinetic (PK), pharmacodynamics (PD) and toxicology studies of the fusion constructs in animals and possible extrapolation of data generated in studies in animal models to humans.

Example 4

Figure 30:
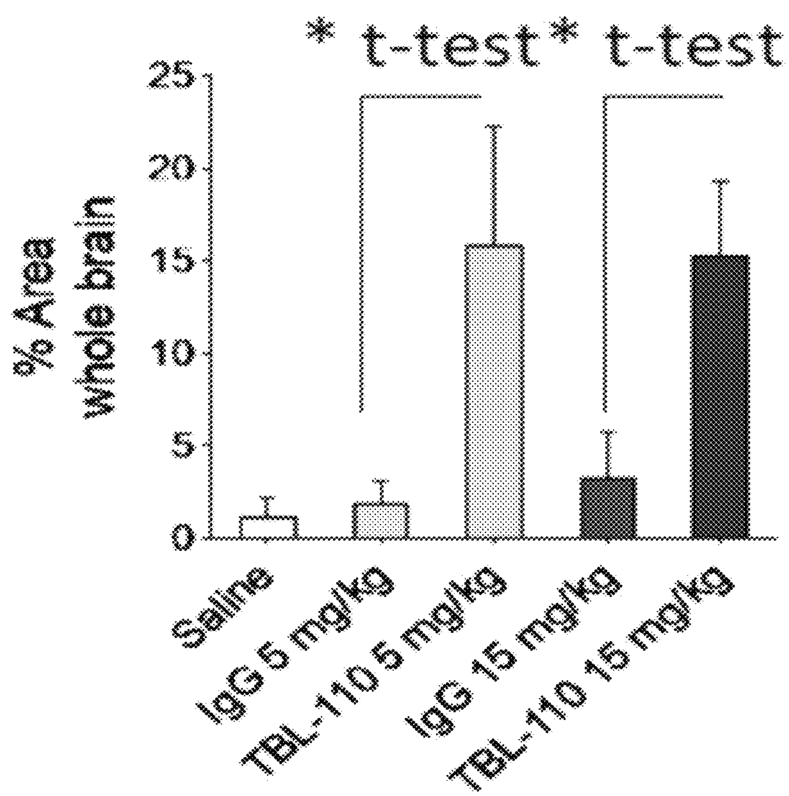
FIG. 30 is a quantitative representation of the immunohistochemical images analyzed for statistical significance Example 4.

A taut 3 overexpressing AAV mouse model was injected intraperitoneally (IP) weekly for 6 months with IgG1 or anti-TauC3 IgG1 (TBL-110) mAb fused to Tfr binding peptide at the C-terminus of the heavy chains. Brain sections were analyzed by immunohistochemistry to determine the relative brain uptake of two different concentrations of control IgG or TBL-100. Images of the antibody stained brain sections were quantitatively analyzed and compared for statistical significance. The images are replicated in FIGS. 29A-29E, and the results of the quantitative analysis brain analysis are provided in Table 1 and are depicted in FIG. 30. The results confirmed significant brain uptake of TBL-110, the fusion construct of Example 1, as compared to control IgG, and that the uptake was dose dependent with the highest uptake occurring at the higher dose. The results are

TABLE 1

| Tukey' s Multiple Comparison Test | Mean Difference | 95.00% Confidence Interval of Difference | Significance |
|---|---|---|---|
| Saline vs IgG 5 mg.kg | −0.736 | −13.91 to 12.43 | ns |
| Saline vs TBL-110 5 mg/kg | −14.67 | −28.64 to −0.70 | Yes (*) |
| Saline vs IgG 15 mg/kg | −2.10 | −14.30 to 10.09 | ns |
| Saline vs TBL-110 15 mg/kg | −14.06 | −28.03 to −0.08 | Yes (*) |
| IgG 5 mg/kg vs TBL-110 5 mg.kg | −13.94 | −27.91 to 0.03 | ns |
| IgG 5 mg/kg vs TBL110 15 mg/kg | −1.36 | −13.55 to 10.83 | ns |
| IgG 5 mg.kg vs TBL-110 15 mg/kg | −13.32 | −27.29 to 0.64 | ns |
| TBL-110 5 mg/kg vs IgG 15 mg/kg | 12.57 | 0.48 to 25.62 | ns |
| TBL-110 5 mg/kg vs TBL-110 15 mg/kg | 0.61 | 14.11 to 15.34 | ns |
| IgG 15 mg/kg vs TBL-110 15 mg/kg | −11.97 | −25.01 to 1.09 | ns |

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A fusion construct of Formula I:

M-L-C (Formula I), wherein M is selected from the group consisting of antibodies, pronectins, affibodies, affilins, anticalins, atrimers, avimers, DARPins, fynomers, bicyclic peptides, and non-antibody proteins, L is an optional linker, and C is a peptide comprising SEQ ID NO: 2, SEQ ID NO: 3, SEQ ID NO: 4, SEQ ID NO: 5, or SEQ ID NO: 28, wherein the non-antibody proteins are therapeutic proteins, and the antibodies comprise (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9); and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12).

2. The fusion construct of claim 1, wherein M is selected from the group consisting of antibodies, pronectins, affibodies, affilins, anticalins, atrimers, avimers, DARPins, fynomers, and bicyclic peptides.

3. A method of delivering peptides across blood-brain barrier (BBB) comprising placing the fusion construct of claim 1 in contact with the BBB.

4. The method of claim 3, wherein M is selected from the group consisting of antibodies.

5. The method of claim 3, wherein Mis an antibody, and the antibody has a binding affinity (KD) for TauC3 of from $1\times10^{-9}$ to $1\times10^{-12}$ and an off-rate ($K_d$) of $1\times10^{-3}$ or less, and a binding affinity (KD) for SEQ ID NO: 1 of from $1\times10^{-4}$ to $1\times10^{-8}$ M, or no detectable binding with SEQ ID NO:1.

6. The fusion construct of claim 1, wherein L is present.

7. A fusion construct of Formula I:

M-L-C (Formula I), wherein M is an antibody,

L is an optional linker, and

C is a peptide comprising SEQ ID NO: 2, SEQ ID NO: 3, SEQ ID NO: 4, SEQ ID NO: 5, or SEQ ID NO: 28, and the antibody comprises (a) a heavy chain variable region comprising CDR1 represented by sequence GFTFN- TYA (SEQ ID NO: 7), CDR2 represented by IRSKSNNYAT (SEQ ID NO: 8), and CDR3 represented by VGGGDF (SEQ ID NO: 9); and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12).

8. The fusion construct of claim 7, wherein SEQ ID NO: 2, SEQ ID NO: 3, SEQ ID NO: 4, SEQ ID NO: 5, or SEQ ID NO: 28 is fused to a heavy chain of the antibody, either monovalently or multivalently.

9. The fusion construct of claim 8, wherein the amino-terminus of the SEQ ID NO: 2, SEQ ID NO: 3, SEQ ID NO: 4, SEQ ID NO: 5, or SEQ ID NO: 28 is fused to the carboxyl-terminus of the heavy chain of the antibody, either monovalently or multivalently.

10. The fusion construct of claim 9, which reduces entrapment and degrades at a slower rate in the endothelial endosomal-lysosomal system than the corresponding antibody in isolation.

11. The fusion construct of claim 9, which has an enhanced blood-brain barrier permeability than the corresponding antibody in isolation.

12. The fusion construct of claim 9 which has a lower effective therapeutic dose than the corresponding antibody in isolation.

13. The fusion construct of claim 7, wherein the peptide SEQ ID NO: 2, SEQ ID NO: 3, SEQ ID NO: 4, SEQ ID NO: 5, or SEQ ID NO: 28 is fused to carboxyl-termini of heavy chains of the antibody, either monovalently or multivalently.

14. The fusion construct of claim 7, wherein the antibody has (i) a binding affinity (KD) for TauC3 from $1\times10^{-9}$ to $1\times10^{-12}$ M, (ii) an off-rate ($k_{off}$) from $1\times10^{-4}$ to $1\times10^{-2}$ $s^{-1}$, and (iii) a binding affinity (KD) for SEQ ID NO:1 from $1\times10^{-4}$ to $1\times10^{-8}$ M, or no detectable binding with SEQ ID NO:1.

15. The fusion construct of claim 14, wherein the antibody shows no detectable binding with SEQ ID NO:1.

16. A method of treating a tauopathy comprising administering to a patient an effective amount of the fusion construct of claim 7, wherein the tauopathy is selected from the group consisting of Pick's disease, progressive supranuclear palsy, corticobasal degeneration, frontotemporal lobar degeneration, frontotemporal dementia, Parkinson's disease, traumatic brain injury, Parkinson's disease, amyotrophic lateral sclerosis, and multiple sclerosis.

17. A fusion construct of Formula I:

M-L-C (Formula I), wherein M is an antibody,

L is a linker, and

C is a peptide comprising SEQ ID NO: 2, and the antibody comprises (a) a heavy chain variable region comprising CDR1 represented by sequence GFTFNTYA (SEQ ID NO: 7), CDR2 represented by IRSKSNNYAT (SEQ ID NO: 8), and CDR3 represented by VGGGDF (SEQ ID NO: 9); and (b) a light chain variable region comprising CDR1 represented by sequence QEISVY (SEQ ID NO: 10), CDR2 represented by sequence GAF (SEQ ID NO: 11), and CDR3 represented by sequence LQYVRYPWT (SEQ ID NO: 12).

* * * * *